(12) United States Patent
Greig et al.

(10) Patent No.: US 10,836,721 B2
(45) Date of Patent: Nov. 17, 2020

(54) THALIDOMIDE ANALOGS AND METHODS OF USE

(71) Applicants: The USA, as represented by the Secretary, Department of Health and Human Services, Bethesda, MD (US); University Court of the University of Aberdeen, Aberdeen (GB)

(72) Inventors: Nigel H. Greig, Phoenix, MD (US); Weiming Luo, Lutherville, MD (US); David Tweedie, Joppa, MD (US); Neil Vargesson, Aberdeen (GB); Shaunna Beedie, Aberdeen (GB); William Douglas Figg, Fairfax, VA (US)

(73) Assignees: The United States of America, as represented by the Secretary, Department of Health and Human Services, Bethesda, MD (US); University Court of the University of Aberdeen, Aberdeen (GB)

( * ) Notice: Subject to any disclaimer, the term of this patent is extended or adjusted under 35 U.S.C. 154(b) by 0 days.

(21) Appl. No.: 16/910,708

(22) Filed: Jun. 24, 2020

(65) Prior Publication Data
US 2020/0325102 A1 Oct. 15, 2020

Related U.S. Application Data

(63) Continuation of application No. 15/764,193, filed as application No. PCT/US2016/054430 on Sep. 29, 2016, now Pat. No. 10,730,835.

(60) Provisional application No. 62/235,105, filed on Sep. 30, 2015.

(51) Int. Cl.
| | |
|---|---|
| *C07D 209/44* | (2006.01) |
| *A61P 29/00* | (2006.01) |
| *A61P 35/00* | (2006.01) |
| *A61K 31/4035* | (2006.01) |
| *A61K 31/428* | (2006.01) |
| *A61K 31/431* | (2006.01) |
| *A61K 31/454* | (2006.01) |
| *A61K 31/4545* | (2006.01) |
| *A61K 31/536* | (2006.01) |
| *A61K 45/06* | (2006.01) |
| *C07D 209/48* | (2006.01) |
| *C07D 209/52* | (2006.01) |
| *C07D 401/04* | (2006.01) |
| *C07D 401/12* | (2006.01) |
| *C07D 401/14* | (2006.01) |
| *C07D 413/04* | (2006.01) |
| *C07D 417/04* | (2006.01) |
| *C07D 471/04* | (2006.01) |
| *C07D 499/80* | (2006.01) |
| *C07D 209/46* | (2006.01) |

(52) U.S. Cl.
CPC ........ *C07D 209/44* (2013.01); *A61K 31/4035* (2013.01); *A61K 31/428* (2013.01); *A61K 31/431* (2013.01); *A61K 31/454* (2013.01); *A61K 31/4545* (2013.01); *A61K 31/536* (2013.01); *A61K 45/06* (2013.01); *A61P 29/00* (2018.01); *A61P 35/00* (2018.01); *C07D 209/46* (2013.01); *C07D 209/48* (2013.01); *C07D 209/52* (2013.01); *C07D 401/04* (2013.01); *C07D 401/12* (2013.01); *C07D 401/14* (2013.01); *C07D 413/04* (2013.01); *C07D 417/04* (2013.01); *C07D 471/04* (2013.01); *C07D 499/80* (2013.01)

(58) Field of Classification Search
CPC .. C07D 209/44; C07D 209/46; C07D 209/48; C07D 209/52; C07D 401/04; C07D 401/12; C07D 401/14; C07D 413/04; C07D 417/04; C07D 471/04; C07D 499/80; A61P 29/00; A61P 35/00; A61K 31/4035; A61K 31/428; A61K 31/431; A61K 31/454; A61K 31/4545; A61K 31/536; A61K 45/06
USPC ........................................................ 514/193
See application file for complete search history.

(56) References Cited

U.S. PATENT DOCUMENTS

| 5,635,517 A | 6/1997 | Muller et al. |
|---|---|---|
| 6,429,212 B1 | 8/2002 | Hashimoto |
| 7,973,057 B2 | 7/2011 | Greig et al. |
| 8,158,653 B2 | 4/2012 | Muller et al. |
| 8,927,725 B2 | 1/2015 | Greig et al. |
| 2009/0298882 A1 | 12/2009 | Muller et al. |

FOREIGN PATENT DOCUMENTS

| WO | WO 94/20085 | 9/1994 |
|---|---|---|

OTHER PUBLICATIONS

Basaric et al., "Antiproliferative and Antiviral Activity of Three Libraries of Adamantane Derivatives", *Arch. Pharm. Chem. Life Sci.*, 347, pp. 334-340 (2014).
Burkhard, J., et al., "Synthesis and Stability of Oxetane Analogs of Thalidomide and Lenalidomide", *Organic Letters*, 2013, 15(17) pp. 4312-4315.
Capitosti, S., et al., "Thalidomide analogues demonstrate dual inhibition of both angiogenesis and prostate cancer", *Bioorganic & Medicinal Chemistry*, 2004, 12, pp. 327-336.
CAS RN 1349993-95-8, STN Entry Date: Dec. 7, 2011.
(Continued)

*Primary Examiner* — Kristin A Vajda
(74) *Attorney, Agent, or Firm* — Klarquist Sparkman, LLP

(57) ABSTRACT

Thalidomide analogs and methods of using the thalidomide analogs are disclosed. Some embodiments of the disclosed compounds exhibit anti-angiogenic and/or anti-inflammatory activity. Certain embodiments of the disclosed compounds are non-teratogenic.

20 Claims, 16 Drawing Sheets

(56) References Cited

OTHER PUBLICATIONS

CAS RN 1320353-00-1, STN Entry Date Aug. 21, 2011.
CAS RN 1019893-58-3, STN Entry Date May 7, 2008.
CAS RN 856828-57-4, STN Entry Date Jul. 25, 2005.
CAS RN 148680-13-1, STN Entry Date Jul. 14, 1993.
CAS RN 137171-51-8, STN Entry Date Nov. 8, 1991.
CAS RN 96529-37-2, STN Entry Date May 25, 1985.
CAS RN 67218-02-4, STN Entry Date Nov. 16, 1984.
CAS RN 36286-53-0, STN Entry Date Nov. 16, 1984.
CAS RN 34706-16-6, STN Entry Date Nov. 16, 1984.
CAS RN 20425-27-8, STN Entry Date Nov. 16, 1984.
CAS RN 5208-26-4, STN Entry Date Nov. 16, 1984.
Communication for EP 16 782 148.7, dated Apr. 14, 2020, 7 pp.
Greig et al., "New therapeutic strategies and drug candidates for neurodegenerative diseases—p53 and TNF-α inhibitors, and GLP-1 receptor agonists," *Annals New York Academy of Sciences* 2004, 1035:290-315.
Greig et al., "Thalidomide-based TNF-α inhibitors for neurodegenerative diseases," *Acta Neurobiol Exp* 64:1-9, 2004.
International Search Report and Written Opinion for PCT Patent Application No. PCT/US2016/054430, dated Feb. 3, 2017, 22 pp.
Luo et al., "Synthesis of aromatic substituted 6'-thiothalidomides," *Synthesis* 2008, 21:3415-3422.
Luo et al., "Design, synthesis and biological assessment of novel N-substituted 3-(phthalimidiny-2-yl)-2,6-dioxopiperidines and 3-substituted 2,6-dioxopiperidines for TNF-α inhibitory activity," *Bioorganic and Medicinal Chemistry* 2011, 19:3965-3972.

Nogueira, A.C., et al., "Thalidomide derivatives and the immune system 6. Effects of two derivatives with no obvious teratogenic potency on the pattern of integrins and other surface receptors on blood cells of marmosets", *Life Sciences*, 1996, 58(4), pp. 337-348.
Orzesko, A., et al., "Tumor necrosis factor-alpha production-regulating activity of phthalimide derivatives in genetically modified murine melanoma cells B78H1", *Il Farmaco*, 2003, 58, pp. 371-376.
Shibata, Y., et al., "N-Alkylphthalimides: Structural Requirement of Thalidomidal Action on 12-0-Tetradecanoylphorbol-13-Acetate-Induced Tumor Necrosis Factor α Production by Human Leukemia HL-60 Cells", *Chem. Pharm. Bull.*, 1995, 43(1) pp. 177-179.
Thornber, "Isosterism and molecular modification in drug design," *Chem. Soc. Rev.* 1979, 8:563-580.
Tsuji, M., et al., "Modulators of Tumor Necrosis Factor α Production Bearing Dicarba-closo-dodecaborane as a Hydrophobic Pharmacophore", *Biol. Pharm. Bull.*, 2000, 23(4) pp. 513-516.
Tweedie et al., "TNF-α synthesis inhibitors on the 3-phthalimidoglutaramide backbone as therapeutic candidates for neurodegenerative diseases," *7th International Conference on Alzheimer's and Parkinson's Disease* 2005, 77-86.
Tweedie et al., "A cellular model of inflammation for identifying TNF-α synthesis inhibitors," *Journal of Neuroscience Methods* 2009, 183:182-187.
Tweedie et al.., "Thalidomide analogues suppress lipopolysaccharide-induced synthesis of TNF-α and nitrite, an intermediate of nitric oxide, in a cellular model of inflammation," *The Open Biochemistry Journal* 2011, 5:37-44.
Van Derpoorten, K., et al., "Anti-HIV activity of N-1-adamtyl-4-aminophthalimide", *Biomed & Pharmacother*, 1997, 51, 464-468.

Scheme 1

FIG. 2 Scheme 2

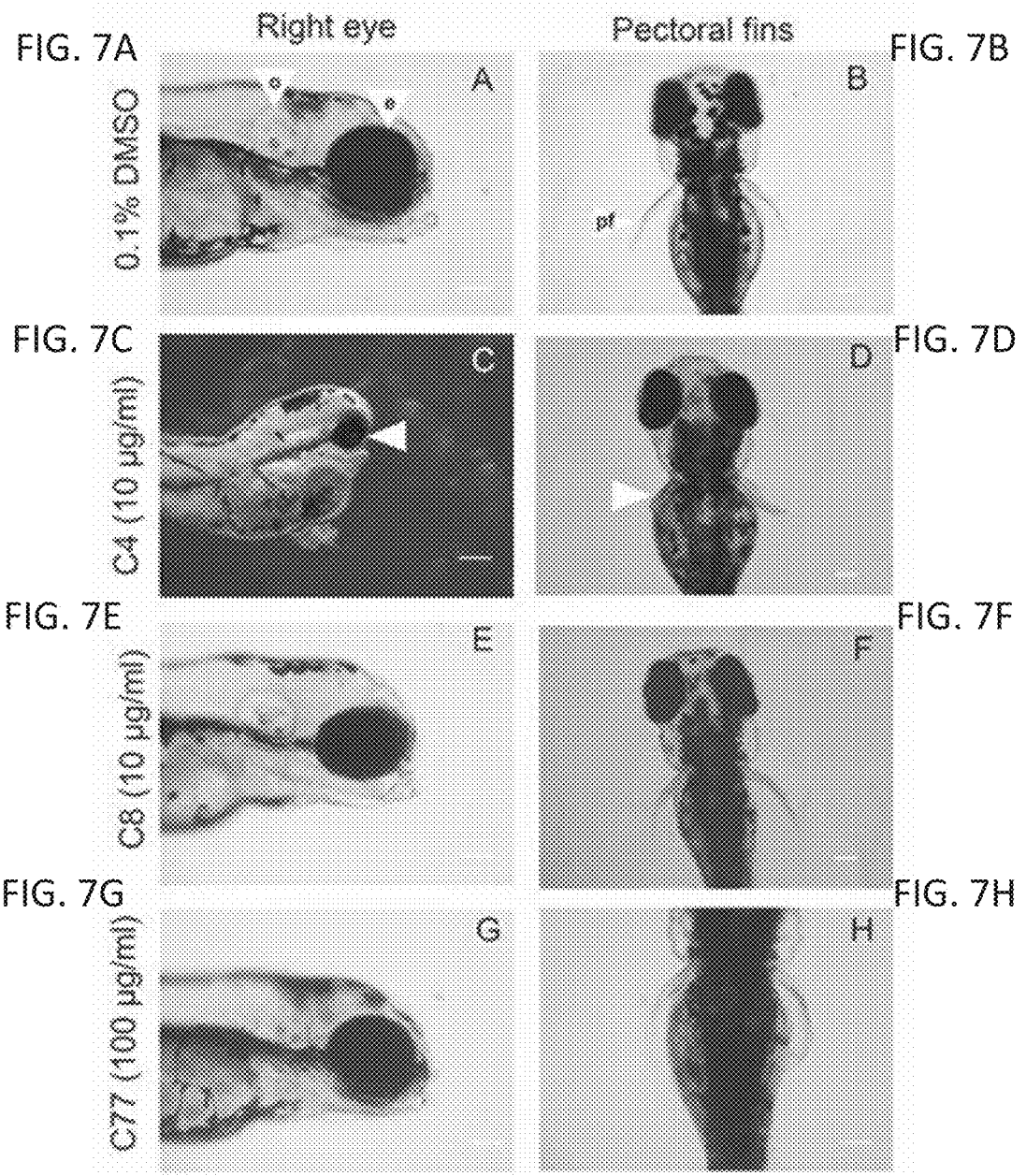

FIG. 7I  FIG. 7K  FIG. 7M
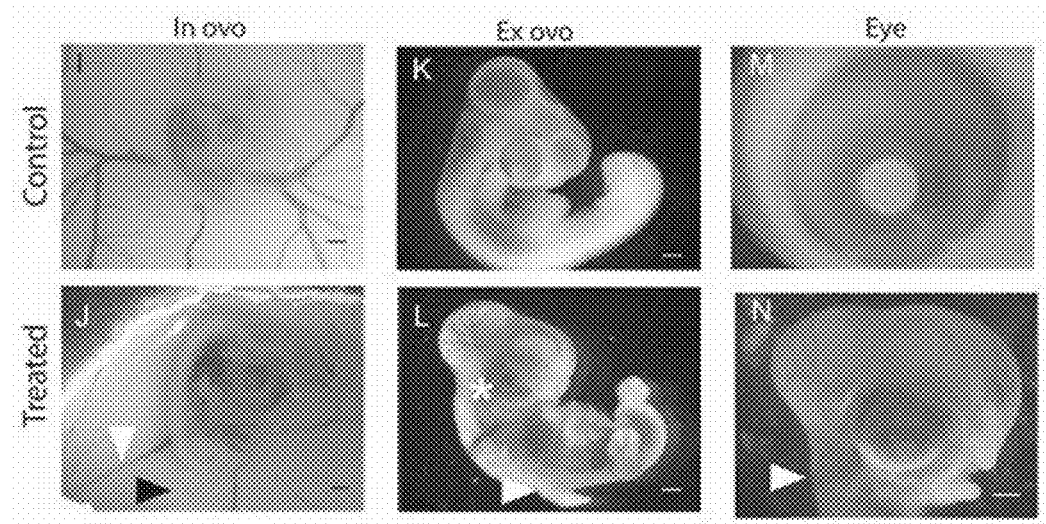
FIG. 7J  FIG. 7L  FIG. 7N
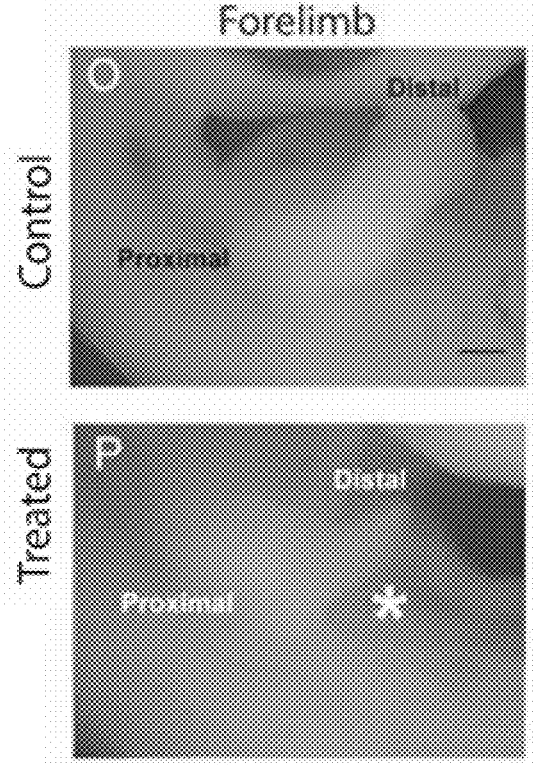
FIG. 7O
FIG. 7P

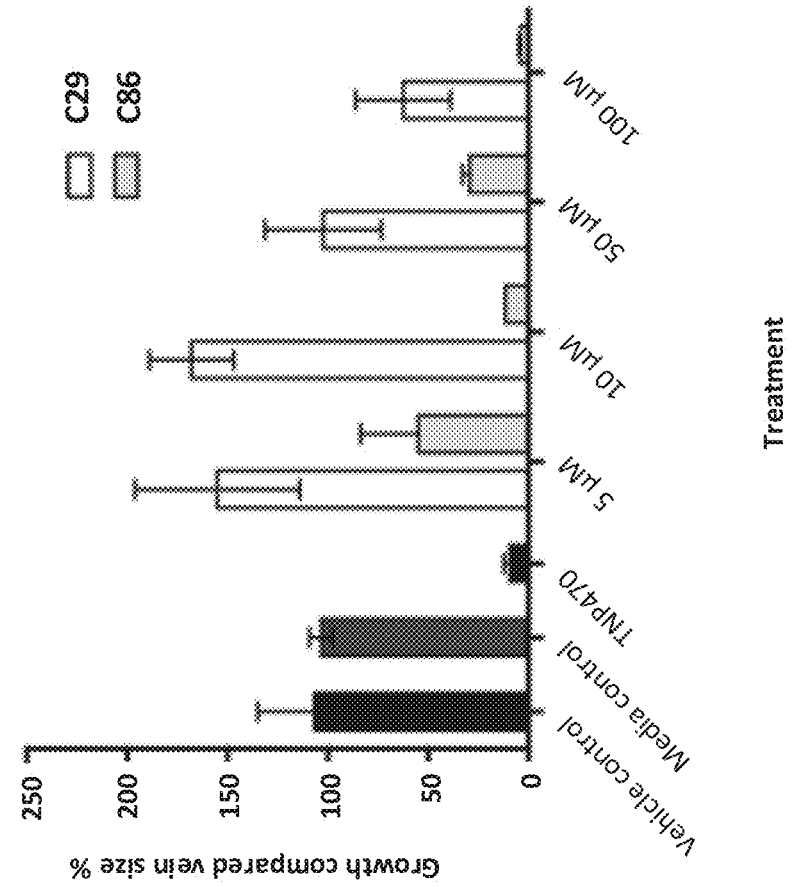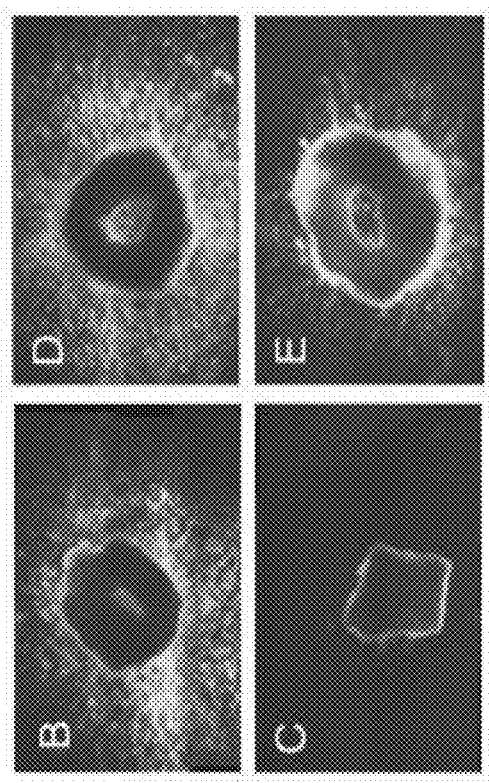

THALIDOMIDE ANALOGS AND METHODS OF USE

CROSS REFERENCE TO RELATED APPLICATIONS

This application is a continuation of U.S. application Ser. No. 15/764,193, filed Mar. 28, 2018, which is the U.S. National Stage of International Application No. PCT/US2016/054430, filed Sep. 29, 2016, which was published in English under PCT Article 21(2), which in turn claims the benefit of U.S. Provisional Application No. 62/235,105, filed Sep. 30, 2015, each of which is incorporated herein in its entirety.

FIELD

This disclosure concerns thalidomide analogs, particularly identification of non-teratogenic analogs, and methods of use.

BACKGROUND

Thalidomide (N-α-phthalimidoglutarimide) is an infamous drug known for its potent teratogenic side effects. Thalidomide was first synthesized in Germany in 1954 and was marketed from 1957 worldwide as a non-barbiturate, non-addictive, non-toxic sedative and anti-nausea medication. Thalidomide was withdrawn from the world market in 1961 due to the development of severe congenital abnormalities in babies born to mothers using it for morning sickness. Thalidomide caused thousands of cases of limb reduction anomalies, including phocomelia (absence of the long bones in the forelimb) or amelia (a complete absence of the forelimb) in the children of pregnant women in the 1950s and 1960s. Other phenotypic malformations were also commonly seen including eye, ear, heart, gastrointestinal and kidney defects. Analogs of thalidomide are also commonly teratogenic.

Subsequent use, and research into the underlying mechanisms of action of thalidomide, found it perpetuates inflammatory and immunomodulatory characteristics. The immunological and inflammatory basis for the clinical efficacy of thalidomide lies in thalidomide's ability to inhibit the synthesis of tumor necrosis factor alpha (TNF-α). TNF-α and family members play pivotal roles in a variety of physiological and pathological processes, which include cell proliferation and differentiation, apoptosis, the modulation of immune responses and induction of inflammation. Thalidomide has also been shown to alter the density of TNF-α induced adhesion molecules on leukocytes in order to prevent the binding of the pro-inflammatory cytokine, which may contribute to the anti-inflammatory properties of the drug.

Thalidomide has additionally been found to successfully inhibit the formation of new blood vessels, a process known as angiogenesis. This led to the hypothesis that a loss of normal blood vessel formation could have caused the damage seen in embryos following thalidomide exposure. Since then, thalidomide has been shown to inhibit new vessel formation in chicken embryos and also both the rat aortic ring assay, and in in vitro cultures of human umbilical vein endothelial cells by modulation of the actin cytoskeleton. Thalidomide has been shown to treat hereditary hemorrhagic telangiectasia in human patients by stabilizing leaky, malformed vessels and inhibiting their formation. Thalidomide analogs have also been demonstrated to be anti-angiogenic in chicken embryo assays and zebrafish embryos. Thalidomide's combined anti-angiogenic and anti-inflammatory properties likely lead to its anti-cancer effects and efficacy in the treatment of multiple myeloma as well as documented activity in other cancers.

A need exists for thalidomide analogs that exhibit clinical potential (e.g., anti-inflammatory and/or anti-angiogenic activity) without teratogenicity and/or that have more potency and/or fewer side effects than those of currently used thalidomide analogs.

SUMMARY

This disclosure concerns analogs of thalidomide, pharmaceutically acceptable salts thereof, and pharmaceutical compositions thereof. Methods of using the analogs are also disclosed.

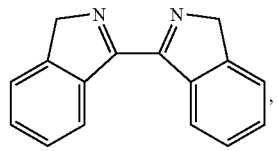 [SMILES: c1ccc2c(c1)CN=C2C1=NCc2ccccc21]

A thalidomide analog has a structure according to general formula I or where general formula I is

With respect to general formula I, $Y^1$ is a bond, —$CH_2$—, or —$CH(CH_3)$—. A is —$NH_3X$ where X is an anion with a −1 charge, or A is general formula II

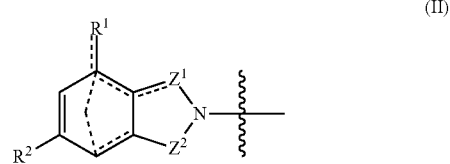

where bonds represented by "----" are optional bonds, and each bond represented by "=====" is a single or double bond as needed to satisfy valence requirements; $R^1$ is —H, —$NO_2$, —$NH_2$, —$OC(O)CH_3$, or —$NO_2H$; $R^2$ is —H, —$NH_2$, or —$N(H)CH(CH_3)_2$; $Z^1$ is $CH_2$, C=O, or CH; and $Z^2$ is $CH_2$, C=O, C=S, or

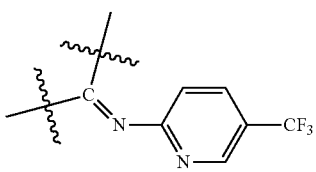 [SMILES: *C(*)=Nc1ccc(C(F)(F)F)cn1]

or

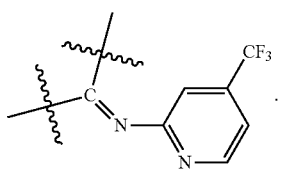 [SMILES: *C(*)=Nc1cc(C(F)(F)F)ccn1]

Ring B is:

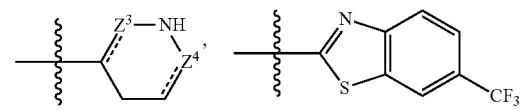

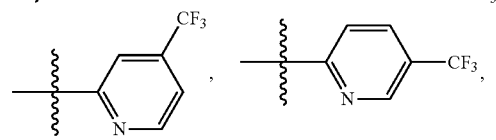

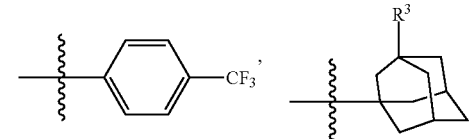

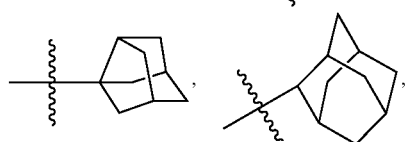

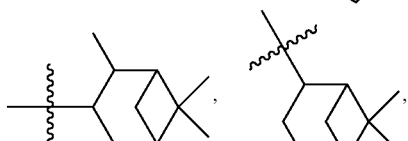

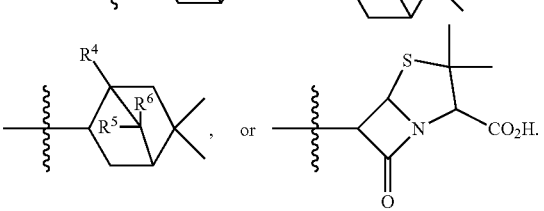

where each bond represented by "- - - -" is a single or double bond as needed to satisfy valence requirements; $Z^3$ is C=O, C=S or CH; $Z^4$ is C=O, C=S or CH, and at least one of $Z^3$ and $Z^4$ is C=O or C=S; $R^3$ is —H or —OH; $R^4$ is —H or —CH$_3$ and $R^5$ and $R^6$ are both —H or both —CH$_3$.

In one embodiment, the thalidomide analog is non-teratogenic in a zebrafish embryo assay and/or a chicken embryo assay at a concentration within a range of 10-200 μg/mL. In an independent embodiment, the thalidomide analog possesses anti-inflammatory properties, but does not possess anti-angiogenic properties. In another independent embodiment, the thalidomide analog possesses anti-angiogenic properties, but does not possess anti-inflammatory properties. In yet another independent embodiment, the thalidomide analog possesses anti-inflammatory and anti-angiogenic properties.

A pharmaceutical composition includes a thalidomide analog or pharmaceutically acceptable salt thereof as disclosed herein and at least one pharmaceutically acceptable carrier or excipient.

A method for inhibiting TNF-α activity, TNF-α synthesis, angiogenesis, inflammation, or a combination thereof, includes contacting a cell with an effective amount of a thalidomide analog as disclosed herein or a pharmaceutically acceptable salt thereof. In some embodiments, the thalidomide analog is non-teratogenic. In certain embodiments, the thalidomide analog is:

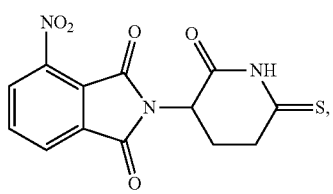

7

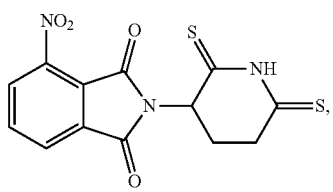

9

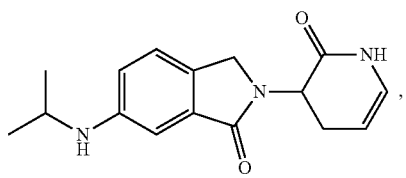

46

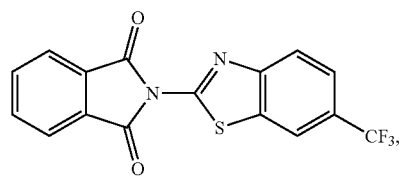

59

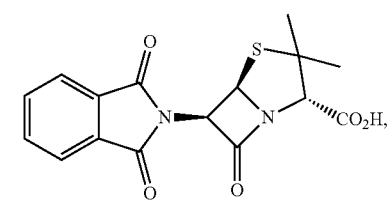

64

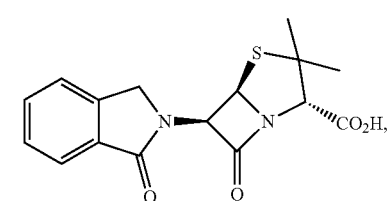

65

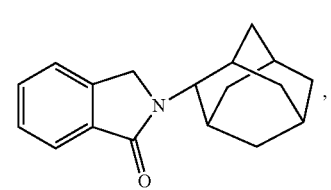

72

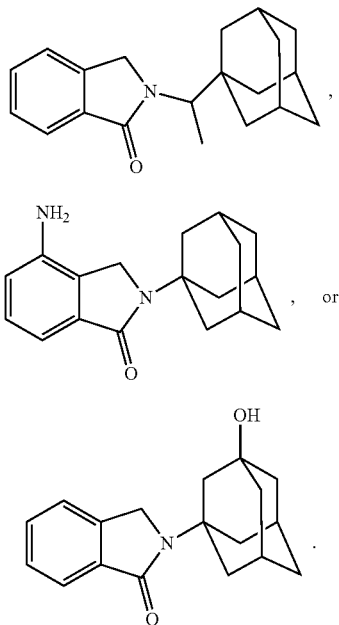

74

77

86

In certain embodiments, the thalidomide analog is compound 7, 9, 46, 59, 65, 74, or 86.

In any or all of the above embodiments, contacting the cell with an effective amount of the thalidomide analog may include administering to a subject a therapeutically effective amount of the thalidomide analog or pharmaceutically acceptable salt thereof or a therapeutically effective amount of a pharmaceutical composition comprising the thalidomide analog or pharmaceutically acceptable salt thereof. In some embodiments, the subject is administered a second therapeutic agent, such as an anti-cancer agent, an anti-angiogenic agent, or an anti-inflammatory agent.

A method for inhibiting inflammation in a subject includes administering to the subject a therapeutically effective amount of a thalidomide analog as disclosed herein, wherein the thalidomide analog is non-teratogenic and possesses anti-inflammatory properties. The thalidomide analog may be compound 7, 9, 46, 59, 64, 65, 72, 74, 77, or 86, as shown above. In certain embodiments, the thalidomide analog is compound 7, 9, 46, 59, 65, 74, or 86. In some embodiments, the non-teratogenic compound is administered orally, parenterally, rectally, nasally, buccally, vaginally, topically, optically, by inhalation spray, or via an implanted reservoir. In certain embodiments, the subject is administered a second therapeutic agent, such as an anti-inflammatory agent.

A method for treating an inflammatory disorder in a subject includes administering to the subject a therapeutically effective amount of a thalidomide analog as disclosed herein, wherein the thalidomide analog is non-teratogenic and possesses anti-inflammatory properties. In some embodiments, the non-teratogenic thalidomide analog is compound 7, 9, 46, 59, 64, 65, 72, 74, 77, or 86. In certain embodiments, the thalidomide analog is compound 7, 9, 46, 59, 65, 74, or 86. In any or all of the foregoing embodiments, the inflammatory disorder may be a neurodegenerative disorder. In any or all of the foregoing embodiments, the subject may be administered a second therapeutic agent, such as an anti-inflammatory agent.

A method for inhibiting TNF-α activity, TNF-α synthesis, or a combination thereof in a subject includes administering to the subject a therapeutically effective amount of a non-teratogenic thalidomide analog. In some embodiments, the non-teratogenic thalidomide analog is compound 7, 9, 46, 59, 64, 65, 72, 74, 77, or 86. In certain embodiments, the thalidomide analog is compound 7, 9, 46, 59, 65, 74, or 86.

The foregoing and other objects, features, and advantages of the invention will become more apparent from the following detailed description, which proceeds with reference to the accompanying figures.

BRIEF DESCRIPTION OF THE DRAWINGS

FIG. 5A is a control; FIG. 5B is an embryo exposed to compound 51 (200 μg/mL); FIG. 5C is an embryo exposed to compound 20 (10 μg/mL); FIG. 5D is an embryo exposed to compound 58 (10 μg/mL).

FIGS. 7A-7P are photomicrographs showing defects seen in zebrafish and chicken embryos following thalidomide analog exposure. Embryos with exposure to a vehicle control showed normal development of the eye (e) (FIG. 7A) otic vesicle (o) (FIG. 7A), and pectoral fins (pf) (FIG. 7B). An anti-angiogenic compound caused microophthalmia (FIG. 7C, white arrow) and malformation in fin development (FIG. 7D, white arrow). A compound with no effect in the assays had no effect on development (FIGS. 7E, 7F). An anti-inflammatory compound had no effect on eye (FIG. 7G) or fin (FIG. 7H) development. A chick embryo control in ovo had normal vasculature (FIG. 7I). Compound 23 caused constriction in vasculature (white arrow) and necrosis (black arrow) of the chorioallantoic membrane (FIG. 7J). FIG. 7K is a control embryo ex ovo. An embryo treated with compound 80 exhibited microophthalmia (asterisk), limb reduction (white arrow), and hemorrhaging throughout the body (FIG. 7L). FIG. 7M shows a normal eye. An embryo treated with compound 81 exhibited growth reduction and hemorrhaging throughout the head (white arrow) (FIG. 7N). FIG.

7O shows a control forelimb. An embryo treated with compound 11 had a limb reduction defect (asterisk, FIG. 7P, ex ovo).

Figure 8A:
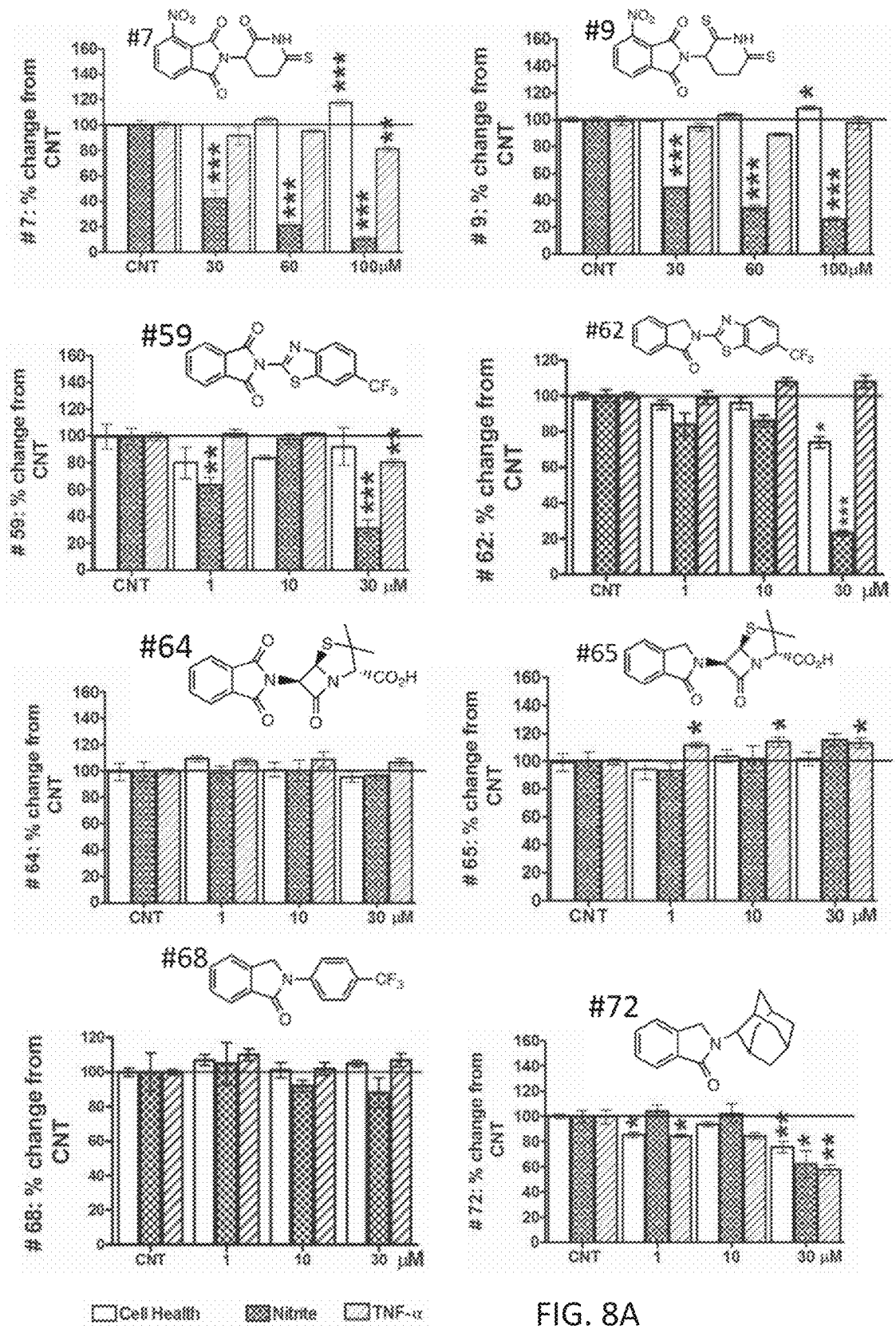
Figure 8B:
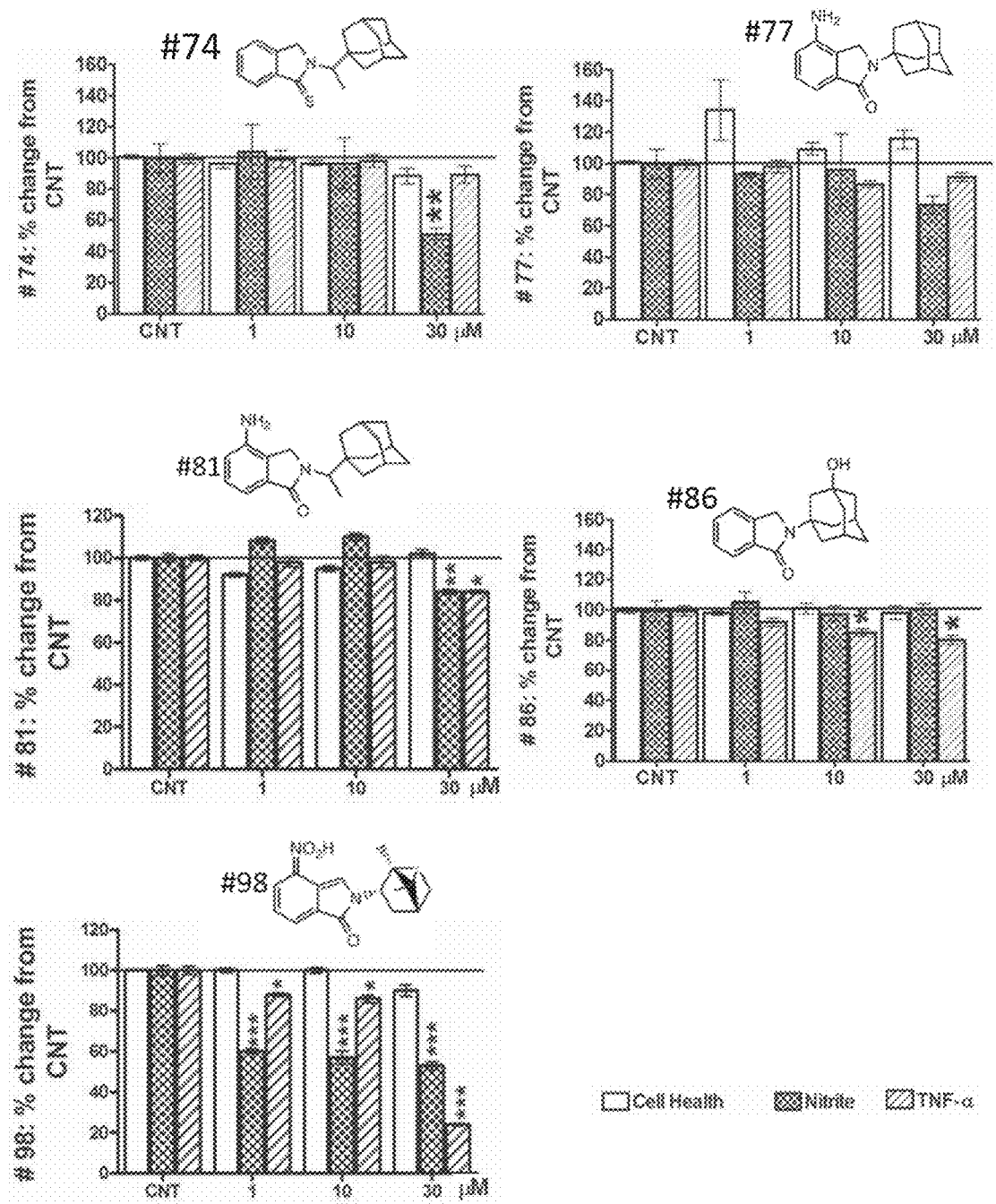

FIGS. 8A and 8B are bar graphs showing effects of thalidomide analogs on cell viability, nitrite levels, and TNF-α protein levels at concentrations ranging from 0-100 µM.

Figure 9:
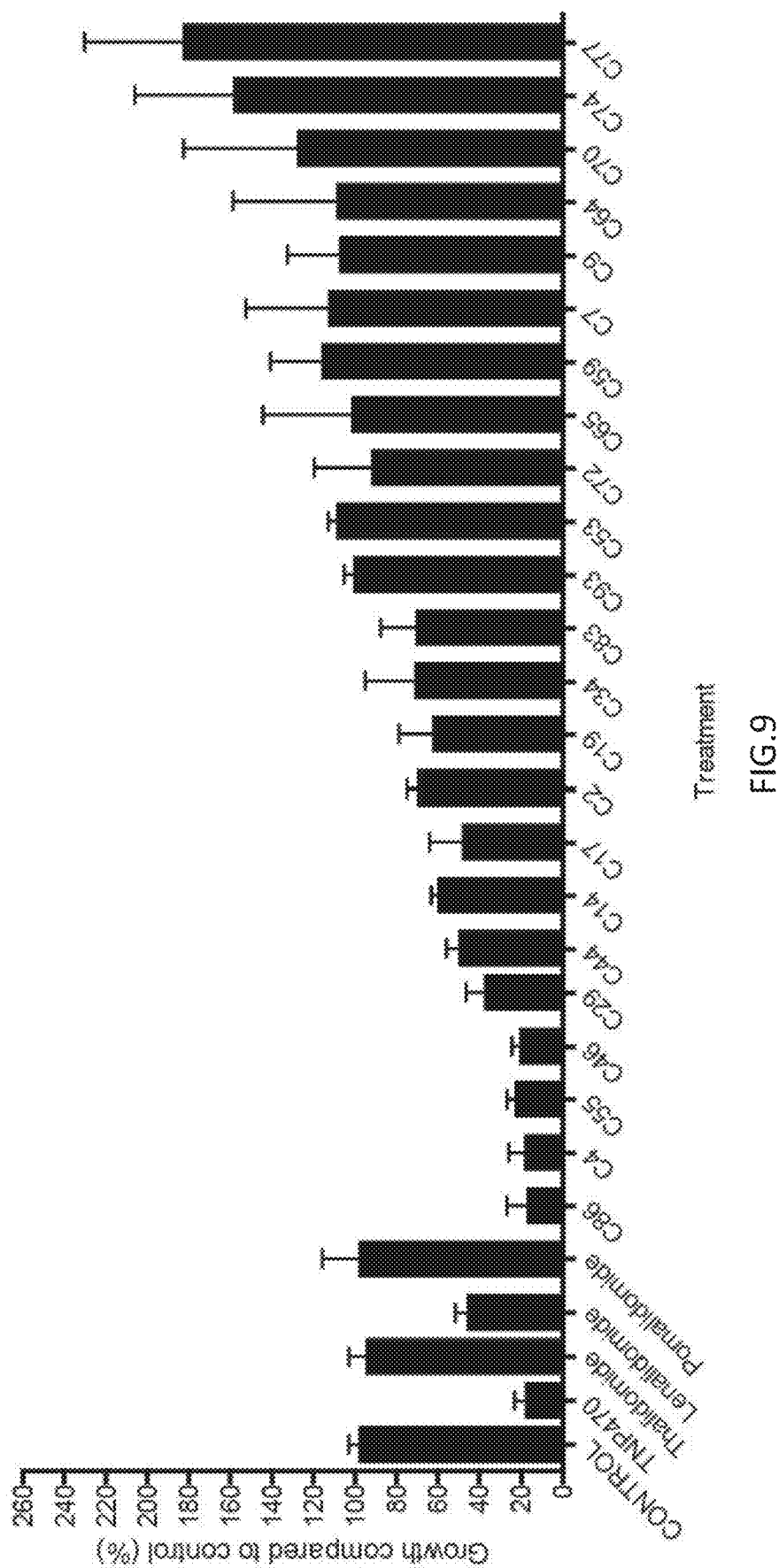

FIG. 9 is a graph showing microvessel outgrowth from rat aortic rings incubated with thalidomide compounds for five days. Error bar represents the standard error of the mean. Control n=11, TNP-470 n=7, thalidomide analogs n=3.

Figure 10A:
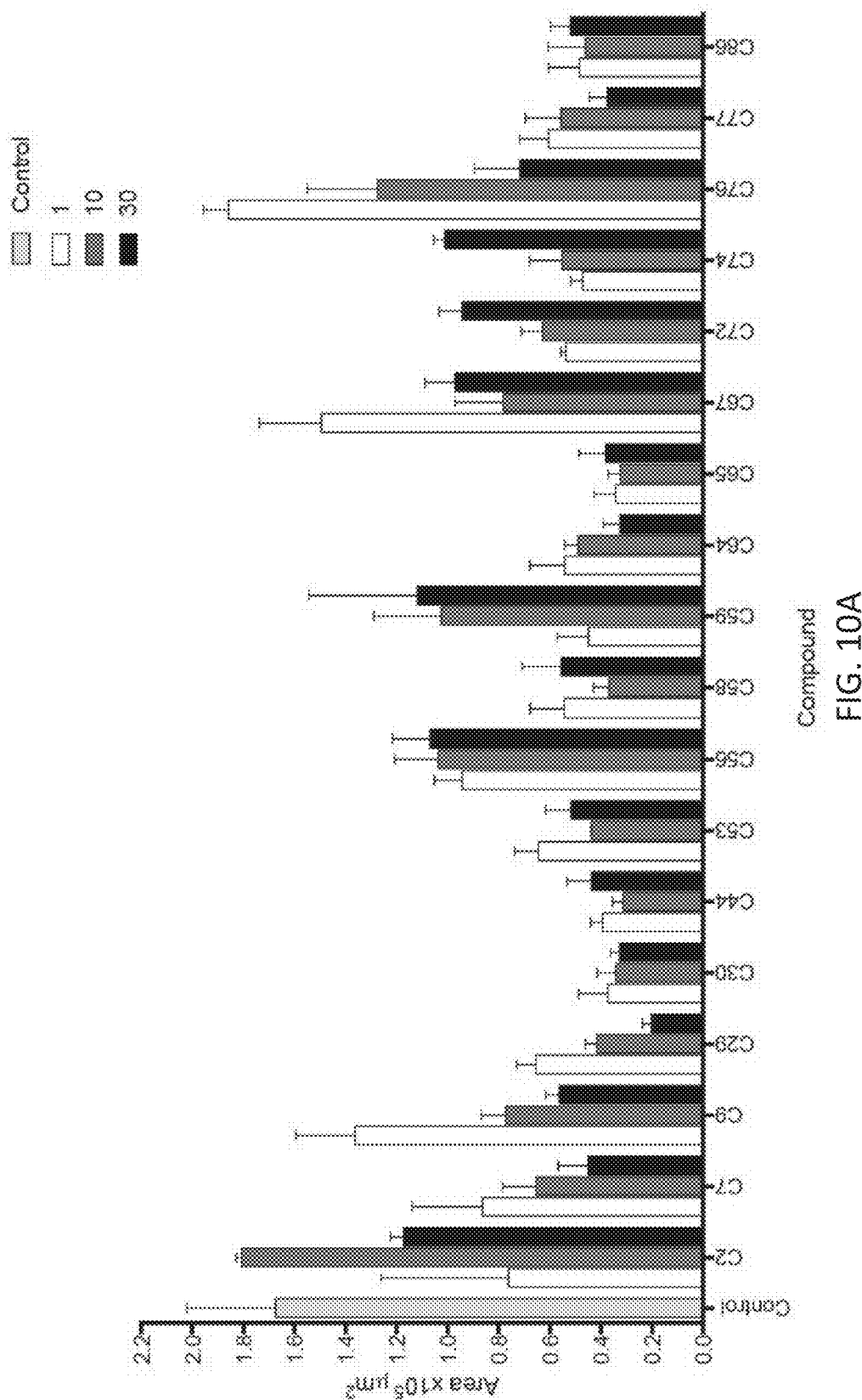
Figure 10B:
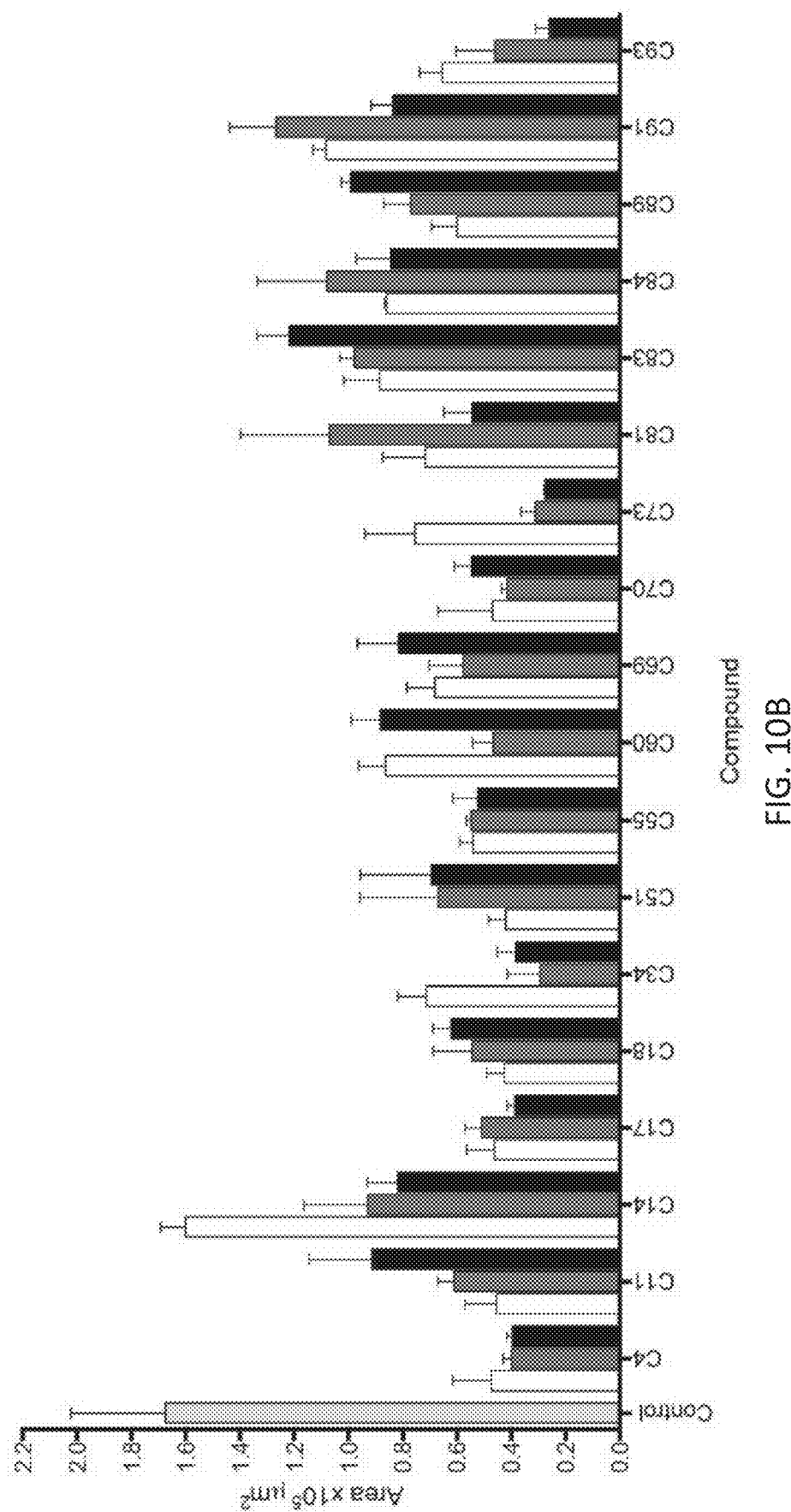

FIGS. 10A and 10B are graphs showing inhibition of lattice outgrowth in human umbilical vein endothelial cells (HUVEC) by thalidomide analogs at concentrations of 1 µM, 10 µM, and 30 µM. Error bar represents the standard error of the mean; n=3.

Figure 11:
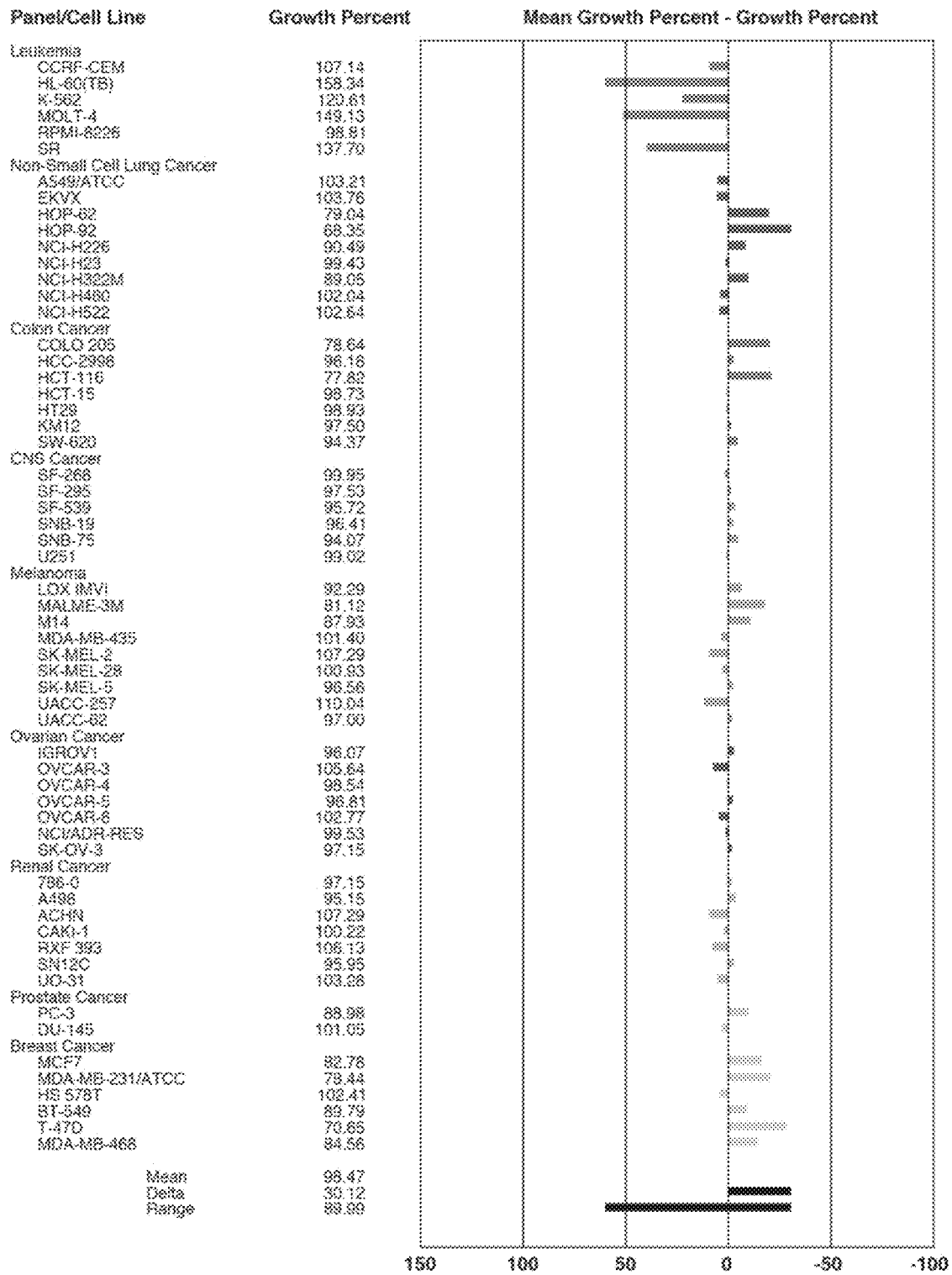

FIG. 11 is a one-dose mean graph showing the effect of compound 29 on cell growth and cytotoxicity in 59 cancer cell lines.

Figure 12:
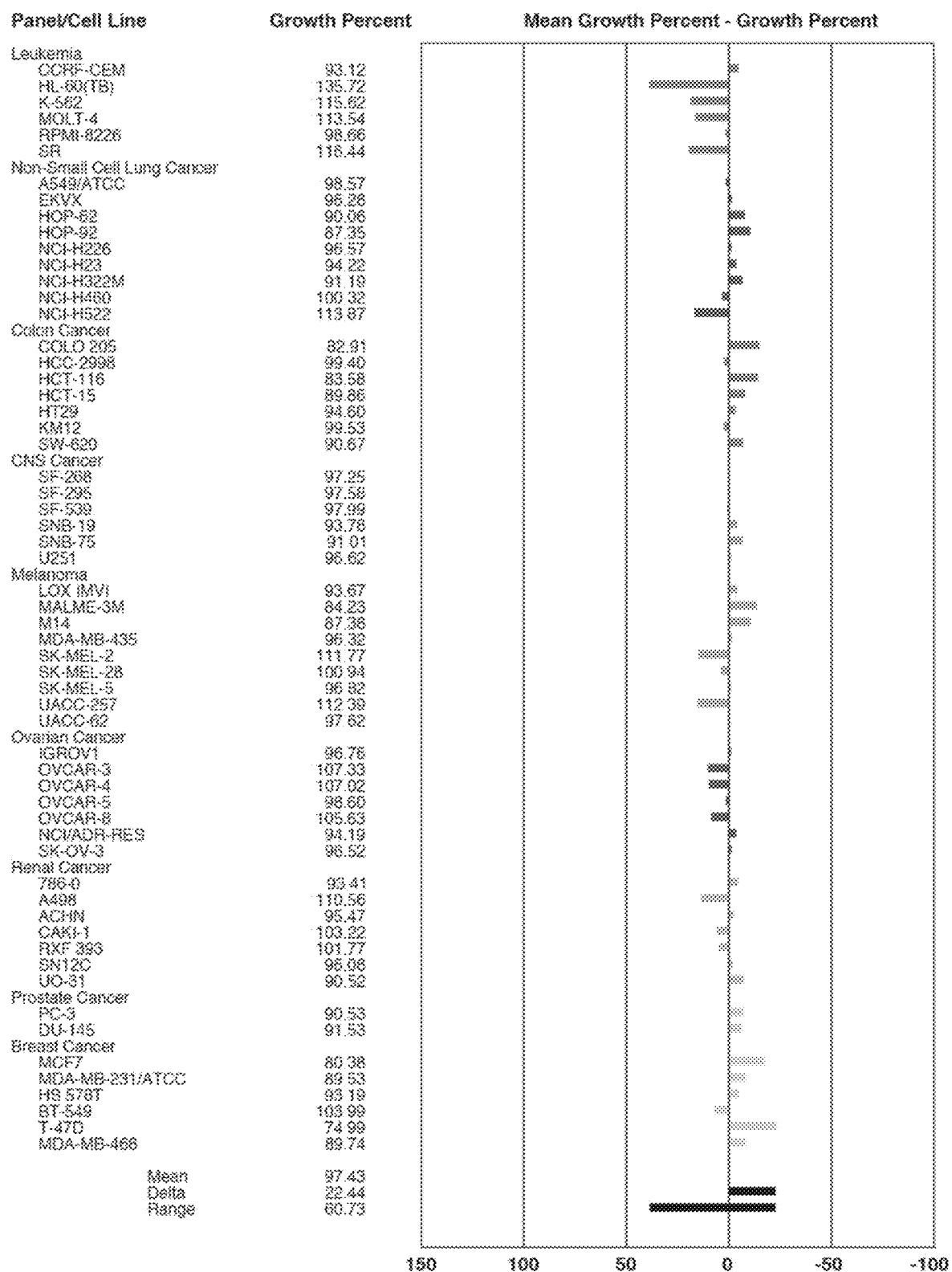

FIG. 12 is a one-dose mean graph showing the effect of compound 86 on cell growth and cytotoxicity in 59 cancer cell lines.

FIGS. 13A-13E show anti-angiogenic activity of compounds 29 and 86 in a human-relevant ex vivo model—the human saphenous vein assay of angiogenesis. FIG. 13A is a graph quantifying microvessel outgrowth in control, positive control, and thalidomide analog-treated human saphenous vein sections. Error bar represents the standard error of the mean. FIG. 13B is an image of outgrowth with no treatment; FIG. 13C shows outgrowth inhibition by TNP-470; FIG. 13D shows no inhibition by compound 29 at 10 µM concentration; FIG. 13E shows vastly reduced outgrowth by compound 86 at 10 µM concentration.

Figure 14:
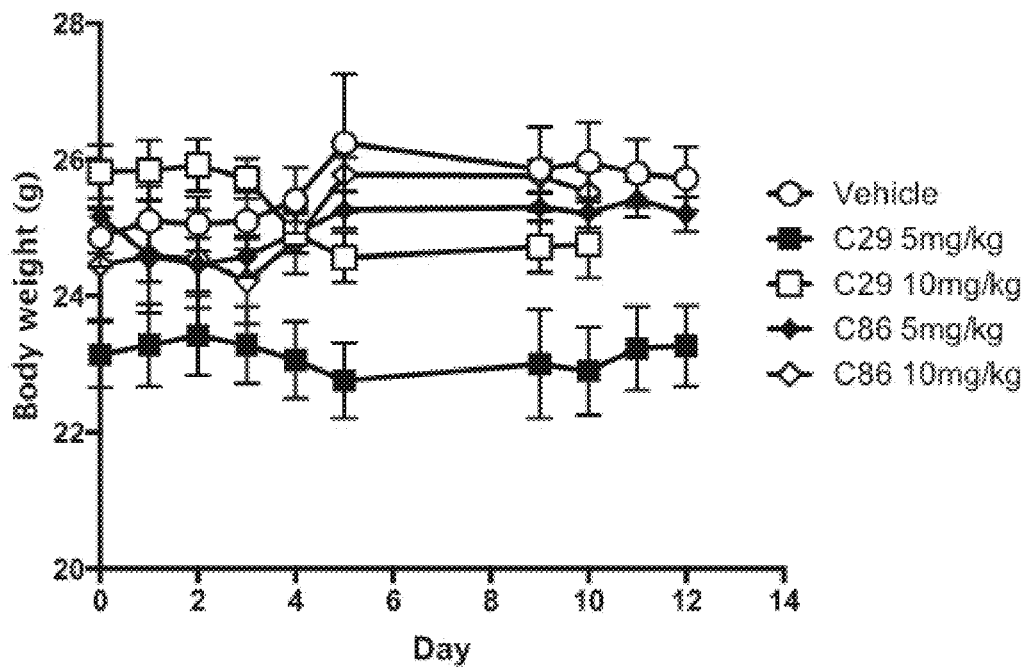

FIG. 14 is graph monitoring weight loss as a measurement of toxicity in mice receiving thalidomide analogs. Error bar represents the standard error of the mean (n=5 per treatment group).

Figure 15:
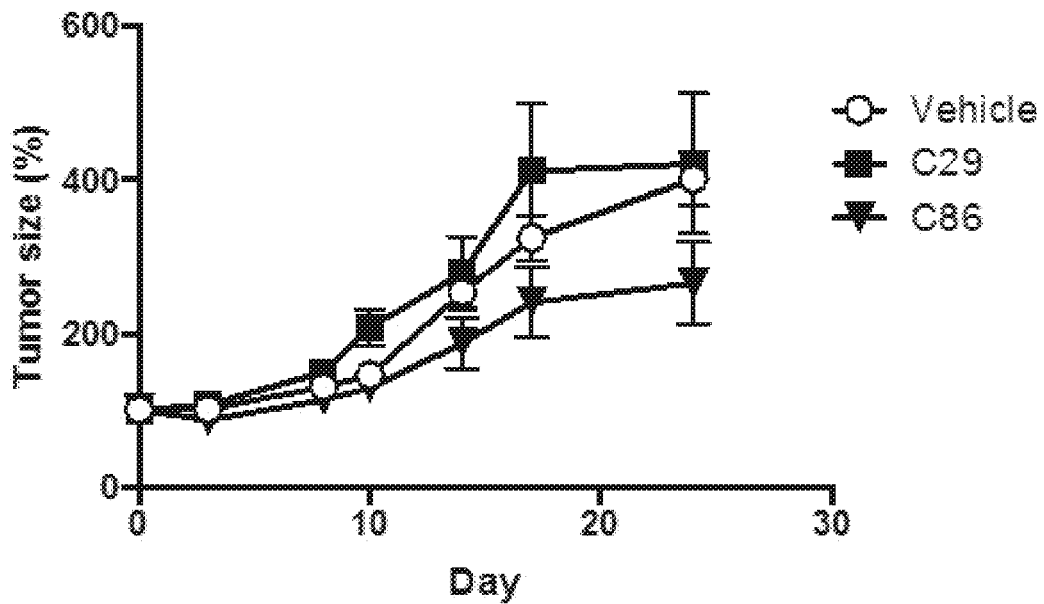

FIG. 15 is a graph monitoring changes in tumor size in mice receiving thalidomide analogs.

DETAILED DESCRIPTION

Embodiments of thalidomide analogs are disclosed, as well as methods of using the analogs. Thalidomide is a tricyclic derivative of glutamic acid having the chemical structure:

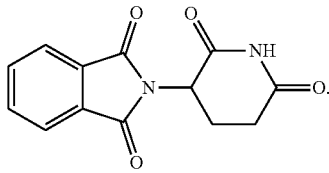 [SMILES: O=C1CCC(N2C(=O)c3ccccc3C2=O)C(=O)N1]

Certain embodiments of the disclosed compounds were unexpectedly found to be non-teratogenic.

I. Definitions

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Definitions of common terms in chemistry may be found in Richard J. Lewis, Sr. (ed.), Hawley's Condensed Chemical Dictionary, published by John Wiley & Sons, Inc., 1997 (ISBN 0-471-29205-2). Definitions of common terms in molecular biology may be found in Benjamin Lewin, Genes VII, published by Oxford University Press, 2000 (ISBN 019879276X); Kendrew et al. (eds.), The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar references.

In order to facilitate review of the various embodiments of the disclosure, the following explanations of specific terms are provided:

Angiogenesis: A physiological process through which new blood vessels form from pre-existing vessels.

An anti-cancer agent is an agent that is used to treat malignancies. Exemplary anti-cancer agents include, but are not limited to, abiraterone, actinomycin D, altretamine, amifostine, anastrozole, asparaginase, bexarotene, bicalutamide, bleomycin, buserelin, busulfan, carboplatin, carmustine, chlorambucil cisplatin, cladribine, clodronate, combretastatin A4, cyclophosphamide, cyproterone, cytarabine, dacarbazine, daunorubicin, degarelix, diethylstilbestrol, docetaxel, doxorubicin, duocarmycin DM, epirubicin, ethinyl estradiol, etoposide, exemestane, 5-fluorouracil, fludarabine, flutamide, folinic acid, fulvestrant, gemcitabine, goserelin, ibandronic acid, idarubicin, ifosfamide, irinotecan, lanreotide, lenalidomide, letrozole, leuprorelin, medroxyprogesterone, megestrol, melphalan, mesna, methotrexate, octreotide, pamidronate, pemetrexed, mitocmycin, mitotane, mitoxantrone, oxaliplatin, paclitaxel, pentastatin, pipbroman, plicamycin, procarbazine, raltitrexed, stilbestrol, streptozocin, tamoxifen, temozolomide, teniposide, topotecan, triptorelin, vinblastine, vincristine, vinorelbine, and zolendronic acid.

Effective amount or therapeutically effective amount: An amount sufficient to provide a beneficial, or therapeutic, effect to a subject or a given percentage of subjects.

Excipient: A physiologically inert substance that is used as an additive in a pharmaceutical composition. As used herein, an excipient may be incorporated within particles of a pharmaceutical composition, or it may be physically mixed with particles of a pharmaceutical composition. An excipient can be used, for example, to dilute an active agent and/or to modify properties of a pharmaceutical composition. Examples of excipients include but are not limited to polyvinylpyrrolidone (PVP), tocopheryl polyethylene glycol 1000 succinate (also known as vitamin E TPGS, or TPGS), dipalmitoyl phosphatidyl choline (DPPC), trehalose, sodium bicarbonate, glycine, sodium citrate, and lactose.

Inflammation: A protective response to harmful stimuli, often elicited by infection, irritation, injury or destruction of tissues. Inflammation can be provoked by physical, chemical, and/or biologic agents. Inflammation involves immune cells, blood vessels, and molecular mediators such as vasoactive amines, plasma endopeptidases, prostaglandins, neutrophil products, lymphocyte factors, and others. Some hormones are anti-inflammatory while others are proinflammatory. Signs of inflammation include pain, heat, redness, swelling, and/or loss of function.

Pharmaceutically acceptable carrier: The pharmaceutically acceptable carriers (vehicles) useful in this disclosure are conventional. Remington: The Science and Practice of Pharmacy, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more thalidomide analogs as disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutically acceptable salt: A biologically compatible salt of a disclosed compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. Pharmaceutically acceptable acid addition salts are those salts that retain the biological effectiveness of the free bases while formed by acid partners that are not biologically or otherwise undesirable, e.g., inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Pharmaceutically acceptable base addition salts include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19, which is incorporated herein by reference.)

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

Pharmaceutical composition: A composition that includes an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's Pharmaceutical Sciences, Mack Publishing Co., Easton, Pa. (19th Edition).

Stereoisomers: Isomers that differ in the arrangement of their atoms in space are termed "stereoisomers". Stereoisomers that are not mirror images of one another are termed "diastereomers" and those that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−) isomers respectively). A chiral compound can exist as either individual enantiomer or as a mixture thereof. A mixture containing equal proportions of the enantiomers is called a "racemic mixture." E/Z isomers are isomers that differ in the stereochemistry of a double bond. An E isomer (from entgegen, the German word for "opposite") has a trans-configuration at the double bond, in which the two groups of highest priority are on opposite sides of the double bond. A Z isomer (from zusammen, the German word for "together") has a cis-configuration at the double bond, in which the two groups of highest priority are on the same side of the double bond. When spatial orientation is not indicated in a chemical formula, the formula includes all possible spatial orientations.

Teratogenic: Able to disturb the growth and/or development of an embryo or fetus, e.g., able to cause physical defects. A teratogen or teratogenic agent is an agent that induces or increases incidence of abnormal prenatal development. Exemplary teratogens include certain viruses, drugs, or radiation that cause malformations or functional damage to an embryo or fetus. A non-teratogenic agent or compound does not have adverse effects on the growth and/or development of an embryo or fetus.

Treat(ing) or treatment: With respect to a disease or disorder, either term includes (1) preventing the disease or disorder, e.g., causing the clinical symptoms of the disease or disorder not to develop in an animal that may be exposed to or predisposed to the disease or disorder but does not yet experience or display symptoms of the disease or disorder, (2) inhibiting the disease or disorder, e.g., arresting the development of the disease or disorder or its clinical symptoms, and/or (3) relieving the disease or disorder, e.g., causing regression of the disease or disorder or its clinical symptoms.

II. Thalidomide Analogs and Pharmaceutical Compositions

This disclosure concerns thalidomide analogs. Some embodiments of the disclosed compounds exhibit anti-angiogenic properties and/or anti-inflammatory properties, and as such can be used to treat a wide variety of pathological conditions that are linked to angiogenesis and/or inflammation. Certain embodiments of the disclosed compounds modulate TNF-α activity, TNF-α synthesis, and/or angiogenesis. The compounds also may inhibit inducible nitric oxide synthase (iNOS) and proinflammatory cytokines such as IFN-γ, IL-2 and IL-17. Pharmaceutically acceptable salts, stereoisomers, and metabolites of all of the disclosed compounds also are contemplated. In some embodiments, the compounds are lenalidomide or pomalidomide derivatives in which carbonyl groups in corresponding non-sulfur-containing lenalidomide or pomalidomide derivatives are replaced by one or more thiocarbonyl groups.

Most embodiments of the disclosed compounds have a structure according to general formula I:

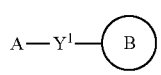

(I)

where $Y^1$ is a bond, —$CH_2$—, or —$CH(CH_3)$—. A is —$NH_3X$ where X is an anion with a −1 charge, or A is general formula II:

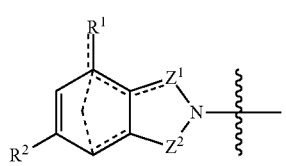

(II)

where bonds represented by "----" are optional bonds, and each bond represented by "=====" is a single or double bond as needed to satisfy valence requirements. $R^1$ is —H, —$NO_2$, —$NH_2$, —$OC(O)CH_3$, or —$NO_2H$; and $R^2$ is —H, —$NH_2$, or —$N(H)CH(CH_3)_2$. In some embodiments at least one of $R^1$ and $R^2$ is —H. $Z^1$ is $CH_2$, C=O, or CH; and $Z^2$ is $CH_2$, C=O, C=S,

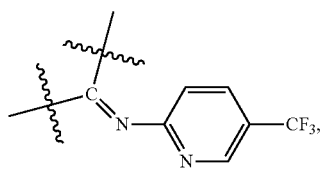 [SMILES: *C(*)=Nc1ccc(C(F)(F)F)cn1]

or

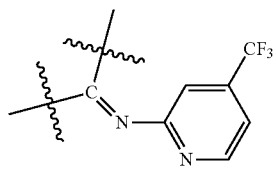

Ring B is:

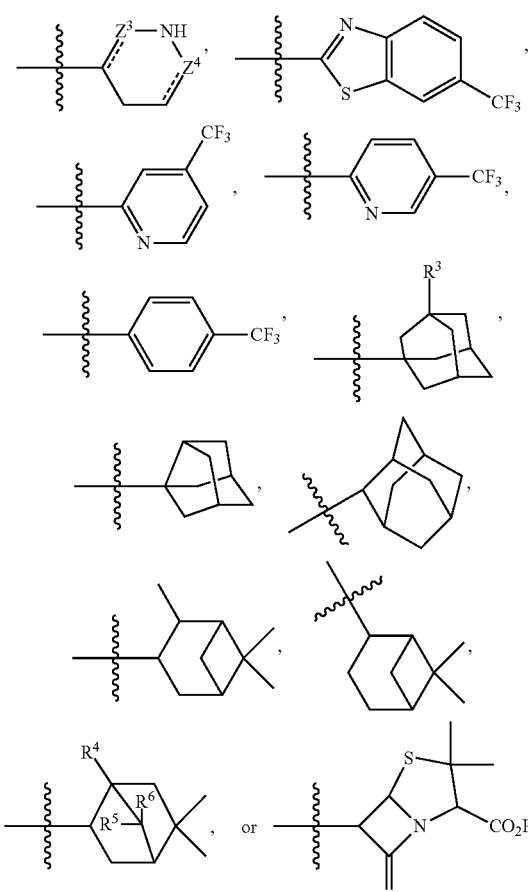

where each bond represented by " - - - " is a single or double bond as needed to satisfy valence requirements. $Z^3$ is C=O, C=S, or CH; $Z^4$ is C=O, C=S, or CH; and at least one of $Z^3$ and $Z^4$ is C=O or C=S. $R^3$ is —H or —OH, $R^4$ is —H or —$CH_3$, and $R^5$ and $R^6$ are both —H or both —$CH_3$.

In some embodiments, the following provisos apply.

When ring B is

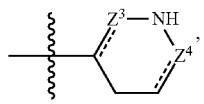

then: (i) $R^1$ is not —$NH_2$; (ii) if $R^1$ is —$NO_2$ and $Y^1$ is a bond, then at least one of $Z^1$ and $Z^2$ is C=O and one of $Z^3$ and $Z^4$ is other than C=O or C=S, or if both $Z^1$ and $Z^2$ are C=O, then $Z^3$ is C=O or C=S and $Z^4$ is C=S; (iii) if $R^2$ is —$NH_2$ and $Y^1$ is a bond, then one of $Z^1$ and $Z^2$ is other than C=O, and one of $Z^3$ and $Z^4$ is other than C=O or C=S; (iv) if $R^2$ is —$NO_2$ and $Y^1$ is a bond, then one of $Z^3$ and $Z^4$ is other than C=O or C=S; (v) if $R^2$ is N(H)CH($CH_3$)$_2$, $Y^1$ is a bond, $Z^1$ is $CH_2$ and $Z^2$ is C=O, then one of $Z^3$ and $Z^4$ is other than C=O; (vi) if A is —$NH_3X$, X is $CF_3CO_2^-$, and $Y^1$ is a bond, then at least one of $Z^3$ and $Z^4$ is other than C=O.

When ring B is

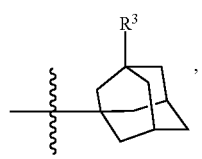

$R^1$ is —H, —$NH_2$ or —$NO_2$, $R^2$ and $R^3$ are —H, $Z^1$ is $CH_2$, and $Z^2$ is C=O, then $Y^1$ is not a bond.

When ring B is

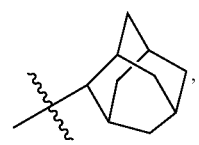 [SMILES: *C1C2CC3CC(C2)CC1C3]

$R^1$ and $R^2$ are H, $Z^1$ is $CH_2$ and $Z^2$ is C=O, then $Y^1$ is not a bond.

When ring B is

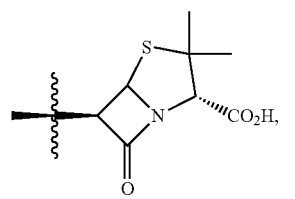 [SMILES: *[C@@H]1C(=O)N2C1SC(C)(C)[C@@H]2C(=O)O]

and $R^1$ and $R^2$ are H, then one of $Z^1$ and $Z^2$ is other than C=O.

In some embodiments, when ring B is

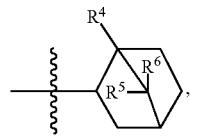

then A is

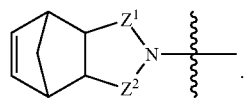

In certain embodiments, A is

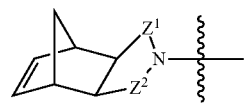

or

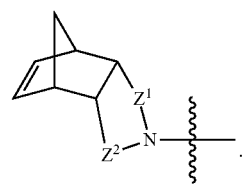

In some embodiments, when ring B is

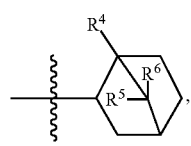

the stereochemistry is

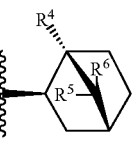

or

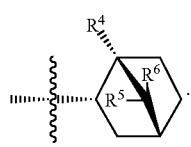

In some embodiments where $R^4$-$R^6$ are H, the stereochemistry is
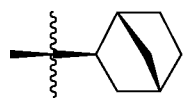 [SMILES: *[C@@H]1C[C@H]2CC[C@@H]1C2]
or
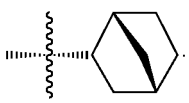
In some embodiments, when ring B is
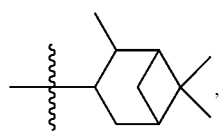
the stereochemistry is
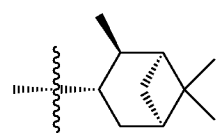 [SMILES: *[C@H]1C[C@H]2C[C@@H]([C@@H]1C)C2(C)C]
or
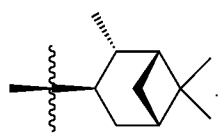 [SMILES: *[C@@H]1C[C@@H]2C[C@H]([C@H]1C)C2(C)C]
In some embodiments, when ring B is
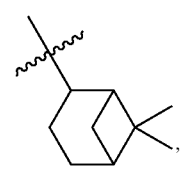 [SMILES: *C1CCC2CC1C2(C)C]
the stereochemistry is
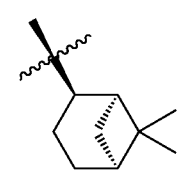 [SMILES: *[C@@H]1CC[C@H]2C[C@@H]1C2(C)C]
or
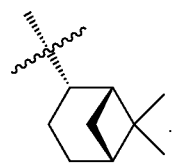 [SMILES: *[C@H]1CC[C@@H]2C[C@H]1C2(C)C]
In an independent embodiment, the disclosed analog is
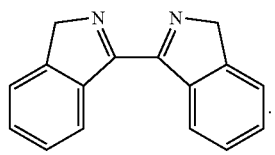 [SMILES: c1ccc2c(c1)CN=C2C1=NCc2ccccc21]
In some embodiments, A is
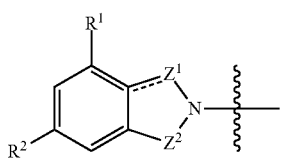
and ring B is:
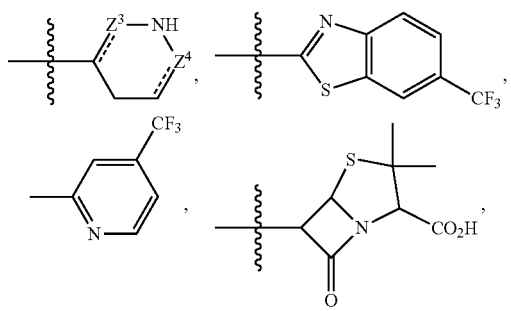
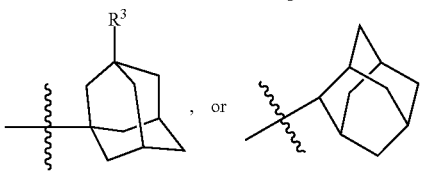
Exemplary compounds are shown in Groups I-VI:
Group I
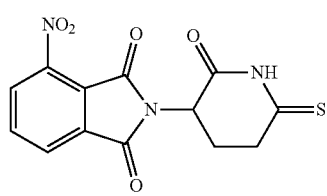

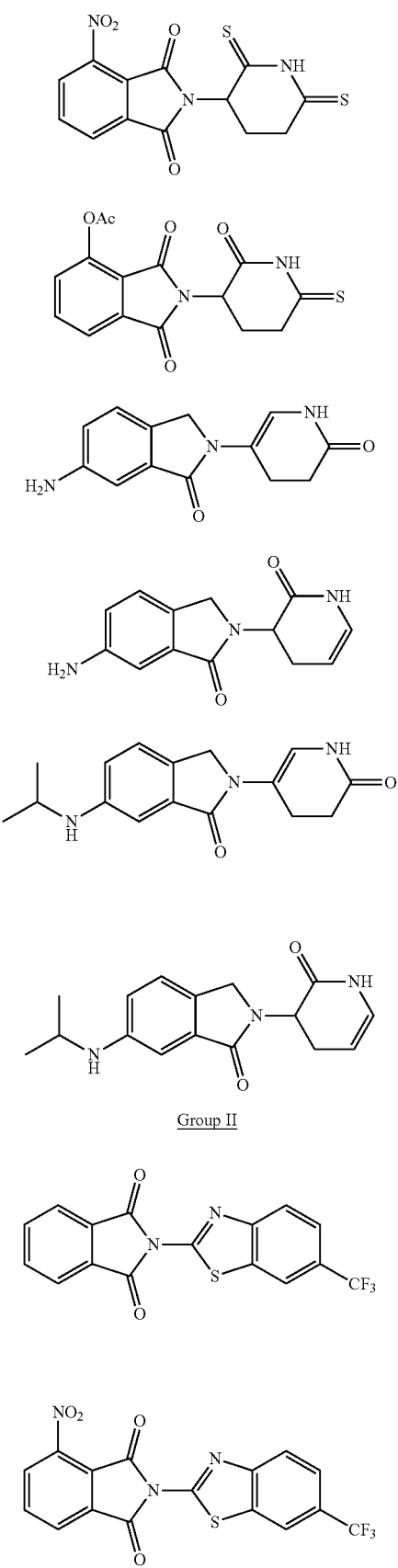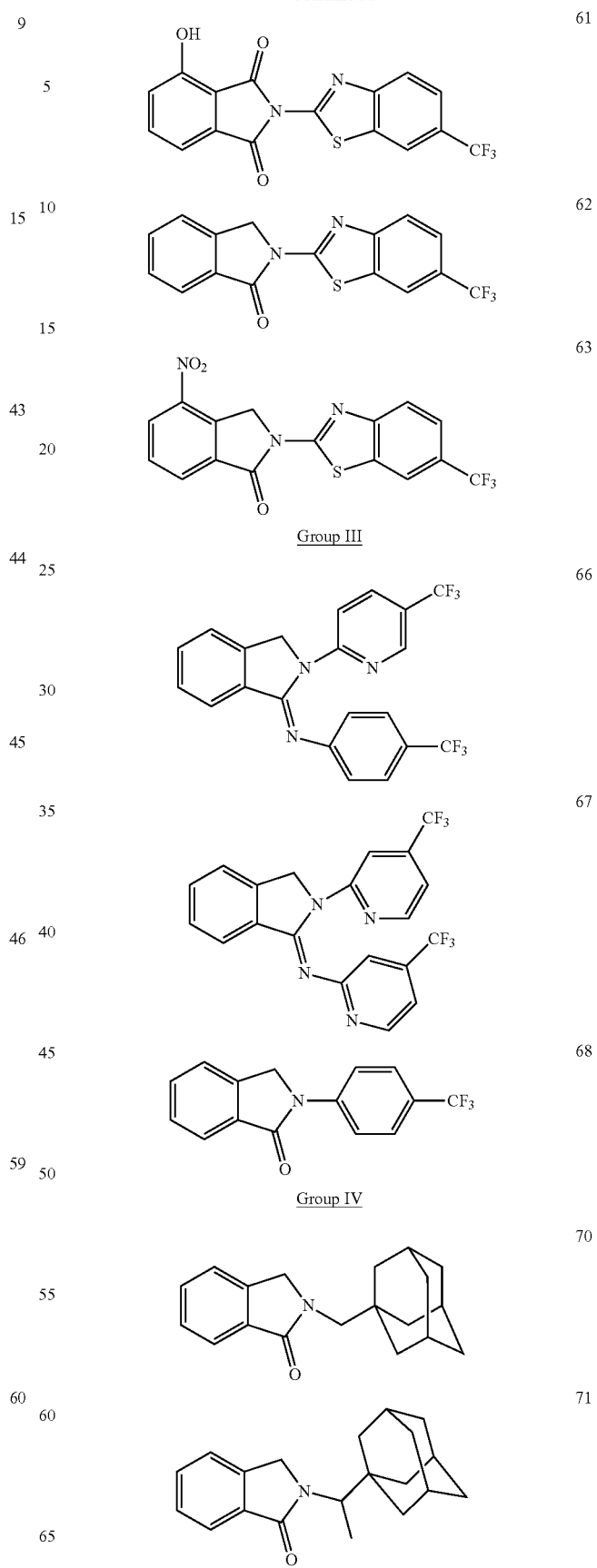

-continued
73
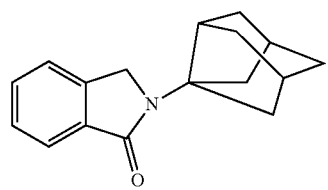
74
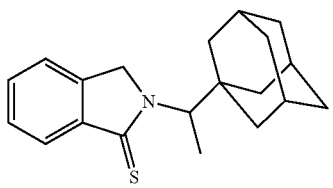
75
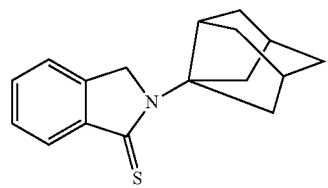
78
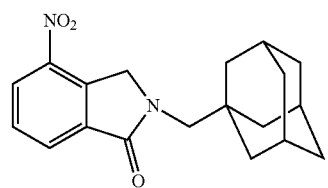
79
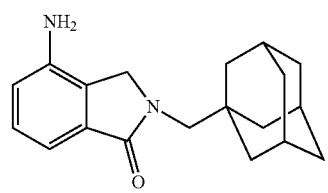
80
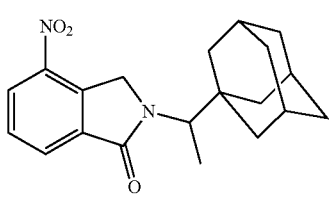
81
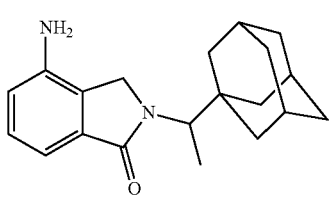
82
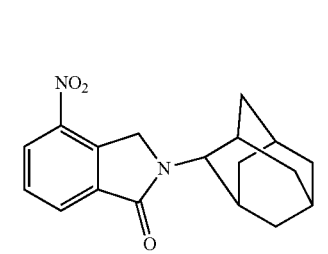
-continued
83
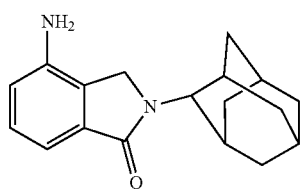
84
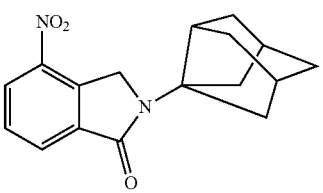
85
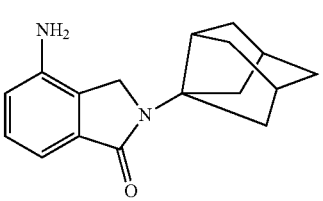
86
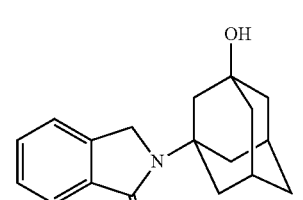
87
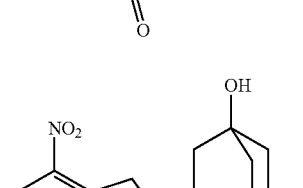
88
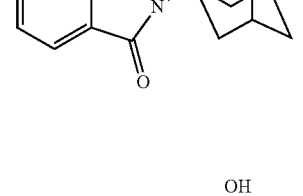
89
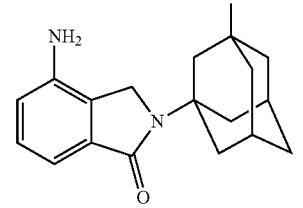

Group V
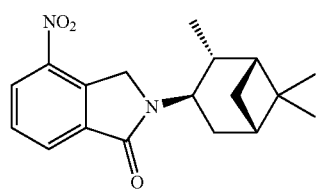 90
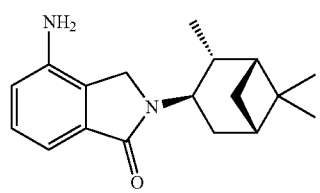 91
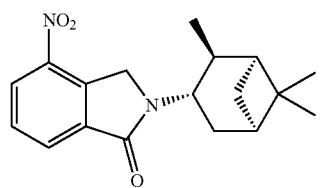 92
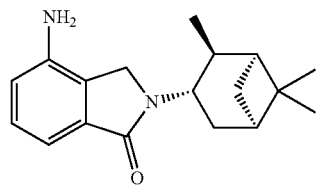 93
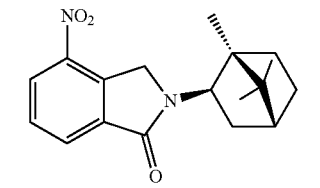 94
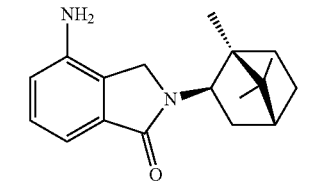 95
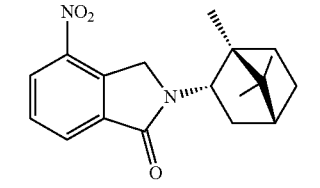 96
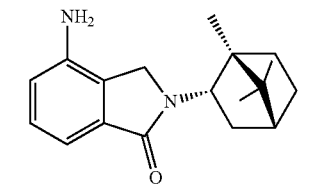 97
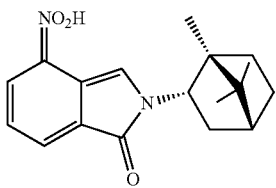 98
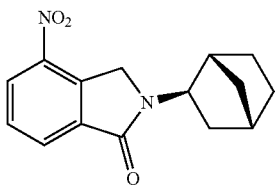 99
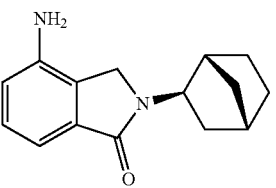 100
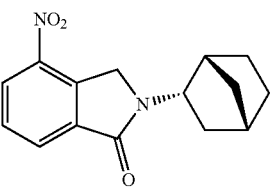 101
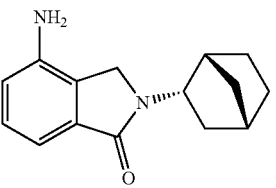 102
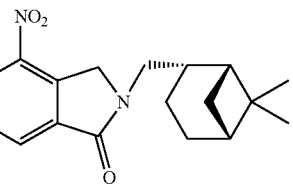 103
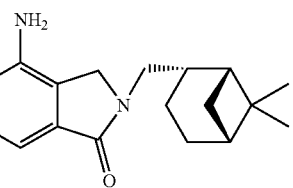 104
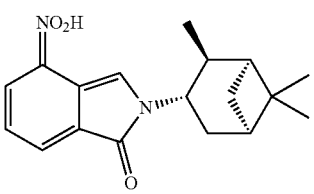 105

112 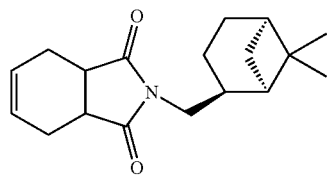

113 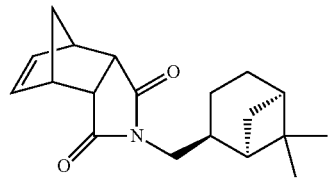

114 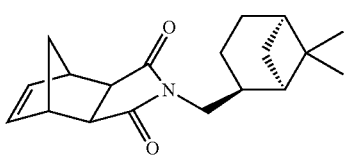

115 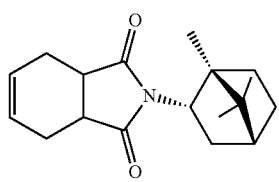

116 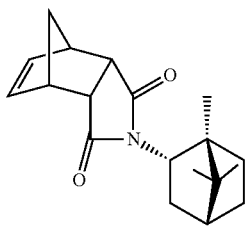

117 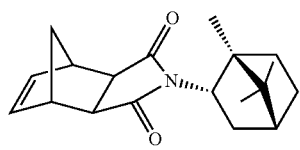

118 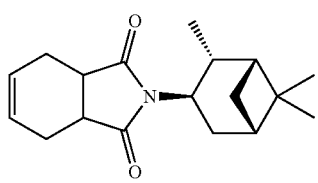

119 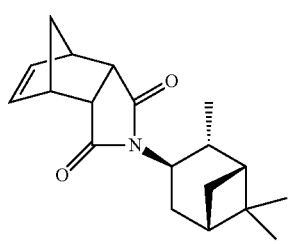

120 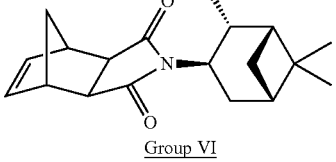

Group VI

65 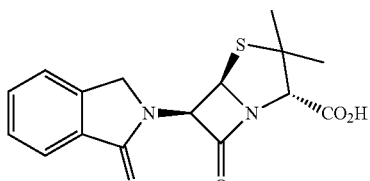

106 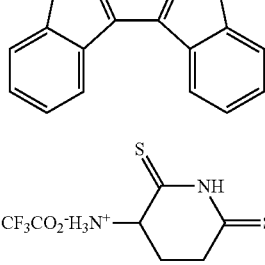

110 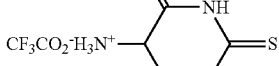

Some embodiments of the disclosed compounds possess anti-inflammatory and/or anti-angiogenic properties. It was unexpectedly discovered that certain of the disclosed compounds are non-teratogenic. In some embodiments, the thalidomide analog is non-teratogenic in a zebrafish embryo assay and/or a chicken embryo assay at a range of concentrations and developmental time points. In some examples, the thalidomide analog was non-teratogenic in the zebrafish embryo assay and/or chicken embryo assay at a concentration within a range of 10-200 μg/mL. It is understood that concentrations at which the thalidomide analog is non-teratogenic may vary in other animal models. In some embodiments, the thalidomide analog is non-teratogenic at a concentration of 0.001 mM to 10 mM, such as from 0.01-1 mM or from 0.02-0.5 mM. In certain embodiments, the thalidomide analog is non-teratogenic at a therapeutically effective dose. Advantageously, the thalidomide analog may be non-neurotoxic at a therapeutically effective dose. In one independent embodiment, the thalidomide analog possesses anti-inflammatory properties and is non-teratogenic. In another independent embodiment, the thalidomide analog possesses anti-inflammatory properties, does not possess anti-angiogenic properties, and is non-teratogenic. In yet another independent embodiment, the thalidomide analog possesses anti-inflammatory properties and is non-teratogenic and non-neurotoxic. Exemplary non-teratogenic compounds are shown in

TABLE 1

7 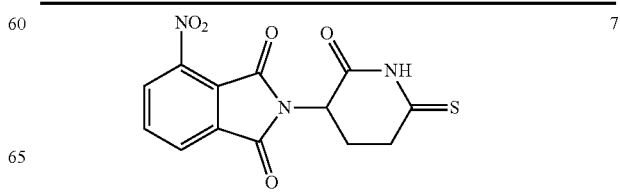

TABLE 1-continued

| | |
|---|---|
| 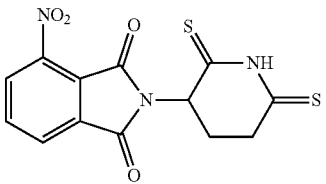 | 9 |
| 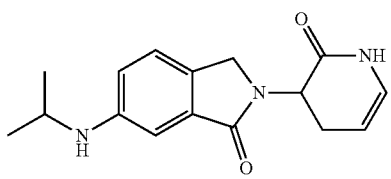 [SMILES: CC(C)Nc1ccc2c(c1)C(=O)N(C1CC=CNC1=O)C2] | 46 |
| 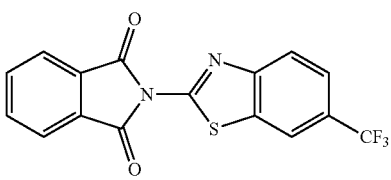 [SMILES: O=C1c2ccccc2C(=O)N1c1nc2ccc(C(F)(F)F)cc2s1] | 59 |
| 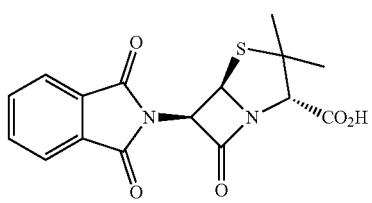 [SMILES: CC1(C)S[C@@H]2[C@H](N3C(=O)c4ccccc4C3=O)C(=O)N2[C@H]1C(=O)O] | 64 |
| 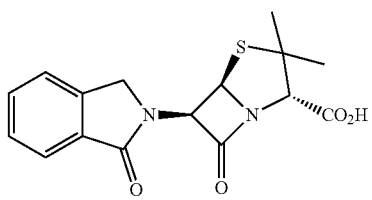 [SMILES: CC1(C)S[C@@H]2[C@H](N3Cc4ccccc4C3=O)C(=O)N2[C@H]1C(=O)O] | 65 |
| 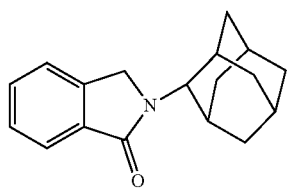 [SMILES: O=C1c2ccccc2CN1C1C2CC3CC(C2)CC1C3] | 72 |
| 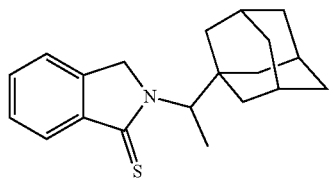 [SMILES: CC(N1Cc2ccccc2C1=S)C12CC3CC(CC(C3)C1)C2] | 74 |
| 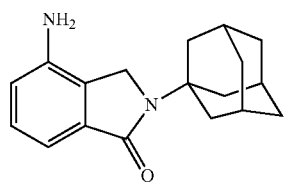 [SMILES: Nc1cccc2c1CN(C13CC4CC(CC(C4)C1)C3)C2=O] | 77 |
| 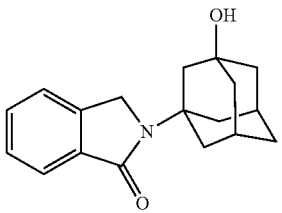 [SMILES: O=C1c2ccccc2CN1C12CC3CC(CC(O)(C3)C1)C2] | 86 |

In some embodiments, the non-teratogenic analog is compound 7, 9, 46, 59, 65, 74, or 86.

The disclosed compounds can be combined with pharmaceutically acceptable carriers, excipients, and optionally sustained-release matrices, such as biodegradable polymers, to form therapeutic compositions. Therefore, also disclosed are pharmaceutical compositions including one or more of any of the compounds disclosed above, a pharmaceutically acceptable carrier and/or excipient. The composition may comprise a unit dosage form of the composition, and may further comprise instructions for administering the composition to a subject to inhibit angiogenesis, for example, instructions for administering the composition to achieve an anti-tumor effect or to inhibit a pathological angiogenesis. Such pharmaceutical compositions may be used in methods for modulating angiogenesis, inflammation, TNF-α activity, and/or TNF-α synthesis in a subject by administering to the subject a therapeutically effective amount of the composition.

The disclosed pharmaceutical compositions can be in the form of tablets, capsules, powders, granules, lozenges, liquid or gel preparations, such as oral, topical, or sterile parenteral solutions or suspensions (e.g., eye or ear drops, throat or nasal sprays, etc.), transdermal patches, and other forms known in the art.

Pharmaceutical compositions can be administered systemically or locally in any manner appropriate to the treatment of a given condition, including orally, parenterally, rectally, nasally, buccally, vaginally, topically, optically, by inhalation spray, or via an implanted reservoir. The term "parenterally" as used herein includes, but is not limited to subcutaneous, intravenous, intramuscular, intrasternal, intrasynovial, intrathecal, intrahepatic, intralesional, and intracranial administration, for example, by injection or infusion. For treatment of the central nervous system, the pharmaceutical compositions may readily penetrate the blood-brain barrier when peripherally or intraventricularly administered.

Pharmaceutically acceptable carriers include, but are not limited to, ion exchangers, alumina, aluminum stearate, lecithin, serum proteins (such as human serum albumin), buffers (such as phosphates), glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Tablets and capsules for oral administration can be in a form suitable for unit dose presentation and can contain conventional pharmaceutically acceptable excipients. Examples of these include binding agents such as syrup, acacia, gelatin, sorbitol, tragacanth, and polyvinylpyrrolidone; fillers such as lactose, sugar, corn starch, calcium phosphate, sorbitol, or glycine; tableting lubricants, such as magnesium stearate, talc, polyethylene glycol, or silica; disintegrants, such as potato starch; and dispersing or wetting agents, such as sodium lauryl sulfate. Oral liquid preparations can be in the form of, for example, aqueous or oily suspensions, solutions, emulsions, syrups or elixirs, or can be presented as a dry product for reconstitution with water or other suitable vehicle before use.

The pharmaceutical compositions can also be administered parenterally in a sterile aqueous or oleaginous medium. The composition can be dissolved or suspended in a non-toxic parenterally-acceptable diluent or solvent, e.g., as a solution in 1,3-butanediol. Commonly used vehicles and solvents include water, physiological saline, Hank's solution, Ringer's solution, and sterile, fixed oils, including synthetic mono- or di-glycerides, etc. For topical application, the drug may be made up into a solution, suspension, cream, lotion, or ointment in a suitable aqueous or non-aqueous vehicle. Additives may also be included, for example, buffers such as sodium metabisulphite or disodium edetate; preservatives such as bactericidal and fungicidal agents, including phenyl mercuric acetate or nitrate, benzalkonium chloride or chlorhexidine, and thickening agents, such as hypromellose.

The compounds can be used in the form of pharmaceutically acceptable salts derived from inorganic or organic acids and bases, including, but not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include, but are not limited to, ammonium salts, alkali metal salts (such as sodium and potassium salts), alkaline earth metal salts (such as calcium and magnesium salts), salts with organic bases (such as dicyclohexylamine salts), N-methyl-D-glucamine, and salts with amino acids (such as arginine, lysine, etc.). Basic nitrogen-containing groups can be quaternized, for example, with such agents as C1-8 alkyl halides (such as methyl, ethyl, propyl, and butyl chlorides, bromides, and iodides), dialkyl sulfates (such as dimethyl, diethyl, dibutyl, and diamyl sulfates), long-chain halides (such as decyl, lauryl, myristyl, and stearyl chlorides, bromides, and iodides), aralkyl halides (such as benzyl and phenethyl bromides), etc. Water or oil-soluble or dispersible products are produced thereby.

III. Uses and Methods of Use

The compounds disclosed herein, and pharmaceutically acceptable salts thereof, may be used for inhibiting TNF-α activity, TNF-α synthesis, angiogenesis, inflammation, or a combination thereof. In one embodiment, a cell is contacted with an effective amount of a thalidomide analog as disclosed herein, to inhibit TNF-α activity, TNF-α synthesis, angiogenesis, inflammation, or a combination thereof. The cell may be contacted in vitro, in vivo, or ex vivo. In one embodiment, the cell is contacted with a thalidomide analog in Groups I-VI. In another embodiment, the cell is contacted with a thalidomide analog in Table 1. In an independent embodiment, the cell is contacted with compound 7, 9, 46, 59, 65, 74, or 86. In any of the foregoing embodiments, contacting the cell with an effective amount of the thalidomide analog may comprise administering to a subject a therapeutically effective amount of the thalidomide analog or pharmaceutically acceptable salt thereof or a therapeutically effective amount of a pharmaceutical composition comprising the thalidomide analog or pharmaceutically acceptable salt thereof. Administration may be performed by any suitable route, including orally, parenterally, rectally, nasally, buccally, vaginally, topically, optically, by inhalation spray, or via an implanted reservoir.

In one embodiment, a subject is administered a therapeutically effective amount of a thalidomide analog according to general formula I, a pharmaceutically acceptable salt thereof, or a pharmaceutical composition comprising the compound. In another embodiment, a subject is administered a therapeutically effective amount of a thalidomide analog in Groups I-VI, a pharmaceutically acceptable salt thereof, or a pharmaceutical composition comprising the compound. In yet another embodiment, a subject is administered a therapeutically effective amount of a thalidomide analog in Table 1, a pharmaceutically acceptable salt thereof, or a pharmaceutical composition thereof. In certain embodiments, the thalidomide analog is compound 7, 9, 46, 59, 65, 74, or 86. In any of the foregoing embodiments, the subject may have a disorder mediated by TNF-α, angiogenesis and/or inflammation. Advantageously, the thalidomide analog in any of the foregoing embodiments may be non-teratogenic. The thalidomide analog also may be non-neurotoxic. In particular, the thalidomide analog may be non-teratogenic at a therapeutically effective dose, such as a therapeutically effective anti-inflammatory dose, a therapeutically effective anti-angiogenic dose, or both. In some embodiments, the thalidomide analog possesses anti-inflammatory properties. In certain embodiments, the thalidomide analog does not possess anti-angiogenic properties. The compound is administered to the subject by any suitable route, including orally, parenterally, rectally, nasally, buccally, vaginally, topically, optically, by inhalation spray, or via an implanted reservoir.

Some embodiments of the thalidomide analogs may be used for treating inflammatory disorders and/or autoimmune disorders. In certain embodiments, a non-teratogenic thalidomide analog as disclosed herein is administered to a subject to inhibit inflammation and/or treat a disorder mediated by inflammation. The non-teratogenic thalidomide analog may possess anti-inflammatory properties while not possessing anti-angiogenic properties. Exemplary inflammatory and/or autoimmune disorders that may be ameliorated with embodiments of the disclosed thalidomide analogs include, but are not limited to, rheumatoid arthritis, immune arthritis, degenerative arthritis, celiac disease, glomerulonephritis, lupus nephritis, prostatitis, inflammatory bowel disease (e.g., Crohn's disease), pelvic inflammatory disease, graft-versus-host disease, interstitial cystitis, autoimmune thyroiditis, Graves' disease; autoimmune pancreatitis, Sjogren's syndrome, myocarditis, autoimmune hepatitis, primary biliary cirrhosis, autoimmune angioedema, bullous pemphigoid, discoid lupus erythematosus, erythema nodosum leprosum, sarcoidosis, pemphigus vulgaris psoriasis, POEMS syndrome, polymyositis, human immune deficiency virus/acquired immune deficiency syndrome, vasculitis, and sarcopenia. Subject to neurotoxicity considerations (e.g., whether the analog is well tolerated by nervous tissue), certain embodiments of the thalidomide analogs disclosed herein may be used to reduce neuroinflammation as a treatment strategy for neurodegenerative disorders. Advantageously, a thalidomide analog used to reduce neuroinflammation may be non-neurotoxic at a therapeutically effective dose. Examples of neurodegenerative and/or neuroinflammatory disorders that may be ameliorated with embodiments of the disclosed thalidomide analogs include, but are not limited to, neurodegeneration resulting from head trauma (e.g., traumatic brain injury), spinal cord injuries, stroke, Alzheimer's disease, Parkinson's disease, ALS (amyotrophic lateral sclerosis), HIV (human immunodeficiency virus) dementia, Huntington's disease, multiple sclerosis, cerebral amyloid angiopathy, tauopathies, peripheral neuropathies, macular degeneration, hearing loss, cochlear injury, epilepsy, a non-epileptic seizure disorder (e.g., due to head injury, dementia, prenatal brain injury, meningitis, lupus, encephalitis, among others), and major depressive disorder (also known as clinical depression, unipolar depression). Embodiments of the disclosed thalidomide analogs may be used to reduce chronic systemic and CNS inflammation and/or as immunomodulatory agents. In some embodiments, the thalidomide analog is used to delay the onset of and/or progression of sarcopenia. Embodiments of the disclosed thalidomide analogs are small molecular weight lipophilic compounds with physicochemical properties to pass through the blood-brain barrier.

Evidence from clinical and preclinical studies indicates that basal inflammatory status increases as a function of normal aging, and progressive development of a mild pro-inflammatory state closely associates with the major degenerative diseases of the elderly (Holmes et al., *Neurology* 73:768-74, 2009; Heneka et al., *Lancet Neurol* 14:388-405, 2015). Hallmarks of aging include increased oxidative stress generated by reactive nitrogen and oxygen species, lipid peroxidation, and mitochondrial and DNA damage, particularly within the brain. Microarray studies indicate an overall rise in inflammatory and pro-oxidant genes with a decline in growth, anti-inflammatory and anti-oxidant genes in the brain as well as other key organs of older versus adult rodents (Cribbs et al., *J Neuroinflammation* 9:179, 2012). In line with this, levels of brain pro-inflammatory cytokines have been found elevated with age in rodents and humans, and several regulatory molecules and anti-inflammatory cytokines were reduced (Deleidi et al., *Front Neurosci* 9:172, 2015). As a source of these pro- and anti-inflammatory molecules, microglia (representing some 15% of cells in brain) are thereby implicated as the major culprit of this neuroinflammation. Correcting the overproduction of pro-inflammatory cytokines generated by microglia provides a strategy to mitigate a broad number of neurodegenerative and systemic disorders in which an inflammatory component drives the disease process. Tumor necrosis factor-α (TNF-α) is one of the primary pro-inflammatory cytokines synthesized and released by microglial cells within the brain and by peripheral blood mononuclear cells PBMCs)/macrophages systemically. Once TNF-α is released, it may initiate a self-propagating cycle of unchecked inflammation (Frankola et al., *CNS Neurol Disord Drug Targets* 10:391-403, 2011). Pharmacological intervention to interrupt this cycle may be of significant benefit in the setting of inflammation-mediated diseases. Reactive nitrogen and oxygen species are both regulators and effectors of inflammation—by generation of nitric oxide (as followed by evaluating nitrite levels: its stable end product) and superoxide/peroxynitrite levels, and their levels can likewise by pharmacologically modulated/reduced by targeting TNF-α, e.g., by administration of a thalidomide analog as disclosed herein.

Proinflammatory TNF-α released by microglia in brain and PBMCs systemically can, if not appropriately time-dependently regulated, initiate a self-propagating cycle of unchecked inflammation and has been implicated in the pathogenesis of a wide number of chronic (AD, Parkinson's disease, ALS) and acute (stroke, traumatic brain injury (TBI)) neurodegenerative disorders as well as autoimmune conditions (Clark & Vissel, *J Neuroinflammation*. 13:236, 2016; Clark & Vissel, *Neural Plast.* 2015:358263, 2015; Chatzantoni & Mouzaki, *Curr Top Med Chem.* 6:1707-14, 2006). Across these disorders, TNF-α levels are found consistently elevated in biological fluids of animal models (Frankola et al., *CNS Neurol Disord Drug Targets* 10:391-403, 2011). In AD, for example, by as much as 25-fold (Tarkowski E, et al. J Clin Immunol 19:223-30, 1999). TNF-α by interacting via NF-κB not only induces the production of other proinflammatory cytokines/chemokines but feeds back to increase its own generation. Studies in subjects with mild cognitive impairment that progress to develop AD suggest that increased CSF TNF-α levels are an early event, and their rise correlates with disease progression (Tarkowski et al., *J Neurol Neurosurg Psychiatry* 74:1200-5, 2003). Paralleling this, elevated expression of TNF-α transcripts are reported within the entorhinal cortex of transgenic mouse models of AD at 2 months, prior to any appearance of amyloid and tau pathology (Janelsins et al., *J Neuroinflamm* 2:23, 2005), and this increase associates with the onset of cognitive deficits in these mice (Billings et al., Neuron 45:675-88, 2005) and later neuronal loss. Likewise, in both stroke and TBI, elevations in TNF-α are evident early in biological fluids and precede neuronal apoptosis (Yoon et al., *J Neurosci Res.* 91:671-80, 2013; Chiu C C, *J Neurosci Methods.* 2016).

A method for inhibiting TNF-α activity and/or TNF-α synthesis in a subject using the disclosed thalidomide analogs is provided. The method includes administering a therapeutically effective amount of a disclosed thalidomide analog to a subject to achieve a TNF-α inhibitory effect. The disclosed thalidomide analogs having TNF-α inhibitory effects are useful for treating many inflammatory, infectious, immunological, and malignant diseases. These include but are not limited to septic shock, sepsis, endotoxic shock, hemodynamic shock and sepsis syndrome, post ischemic reperfusion injury, malaria, mycobacterial infection, meningitis, psoriasis and other dermal diseases, congestive heart failure, fibrotic disease, cachexia, graft rejection, cancer, tumor growth, undesirable angiogenesis, autoimmune disease, opportunistic infections in AIDS, rheumatoid arthritis, rheumatoid spondylitis, osteoarthritis, other arthritic conditions, inflammatory bowel disease, Crohn's disease, ulcerative colitis, multiple sclerosis, systemic lupus erythematosus, ENL in leprosy, radiation damage, and hyperoxic alveolar injury.

Still further, a method for modulating angiogenesis in a subject is provided. The method includes administering to the subject a therapeutically effective amount of one or more of any of the disclosed thalidomide analogs. Desirably, the thalidomide analog possesses anti-angiogenic properties. In some embodiments, where an anti-angiogenic thalidomide analog is utilized, the therapeutically effective amount of the compound can be administered to a subject with a tumor to achieve an anti-tumor effect, such as inhibition of tumorigenesis or tumor metastasis. In other embodiments, the therapeutically effective amount of the thalidomide analog is administered to a subject with a pathological angiogenesis. In still other embodiments, the therapeutically effective amount of the thalidomide analog is administered to a subject with an angiogenesis-mediated retinopathy, such as a non-cancerous retinopathy.

As angiogenesis inhibitors, some embodiments of the disclosed thalidomide analogs are useful in the treatment of both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such thalidomide analogs may also be useful in treating solid tumors arising from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, these thalidomide analogs may be useful in the prevention of metastases from the tumors described above either when used alone or in combination with radiotherapy and/or other chemotherapeutic agents. The thalidomide analogs are also useful in treating multiple myeloma.

Embodiments of the disclosed thalidomide analogs with anti-angiogenic properties can also be used to treat a pathological (i.e. abnormal, harmful or undesired) angiogenesis, for example, various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye; skin diseases such as psoriasis; blood vessel diseases such as hemangiomas, and capillary proliferation within atherosclerotic plaques; Osler-Webber Syndrome; myocardial angiogenesis; plaque neovascularization; telangiectasia; hemophiliac joints; angiofibroma; and wound granulation. Other uses include the treatment of diseases characterized by excessive or abnormal stimulation of endothelial cells, including but not limited to intestinal adhesions, Crohn's disease, atherosclerosis, scleroderma, and hypertrophic scars, such as keloids. The disclosed thalidomide analogs are also useful in the treatment of diseases that have angiogenesis as a pathologic consequence such as cat scratch disease (Rochele minalia quintosa) and ulcers (*Helicobacter pylori*). The disclosed thalidomide analogs are also useful to reduce bleeding by administration prior to surgery, especially for the treatment of resectable tumors.

In certain embodiments, the thalidomide analogs disclosed herein may exhibit no toxicity or tolerable toxicity at dosages of up to 25 mg/daily, such as up to 50 mg/daily or even up to 75 mg/daily. The therapeutically effective amount or amount depends, for example, on the condition treated, nature of the formulation, nature of the condition, embodiment of the claimed pharmaceutical compositions, mode of administration, and condition and weight of the patient. Dosage levels are typically sufficient to achieve a tissue concentration at the site of action that is at least the same as a concentration that has been shown to be active in vitro, in vivo, or in tissue culture. For example, a dosage of about 0.1 µg/kg body weight/day to about 1000 mg/kg body weight/ day, for example, a dosage of about 1 µg/kg body weight/day to about 1000 µg/kg body weight/day, such as a dosage of about 5 µg/kg body weight/day to about 500 µg/kg body weight/day can be useful for treatment of a particular condition. Advantageously, certain embodiments of the disclosed thalidomide analogs are non-teratogenic at therapeutically effective amounts.

The disclosed thalidomide analogs can be used in combination with other compositions and procedures for the treatment of diseases. In some embodiments, the disclosed thalidomide analogs are used in combination with a second therapeutic agent, such as an anti-cancer agent, an anti-angiogenic agent, or an anti-inflammatory agent. For example, a tumor can be treated conventionally with surgery, radiation or chemotherapy in combination with an anti-angiogenic compound/concentration and then, optionally the compound/concentration can be further administered to the subject to extend the dormancy of micrometastases and to stabilize and inhibit the growth of any residual primary tumor. Alternatively, an angiogenic compound or angiogenic concentration of a compound can be used in combination with other angiogenesis stimulating agents. For example, thermal energy (in the form of resistive heating, laser energy or both) to create thermally treated stimulation zones or pockets (optionally interconnected, at least initially, by small channels) in the tissue for the introduction of blood born growth and healing factors, along with stimulated capillary growth surrounding the thermally treated zones. Such stimulation zones allow increased blood flow to previously ischemic and/or nonfunctional tissue (such as cardiac tissue) with a concomitant increased supply of oxygen and nutrients ultimately resulting in a revitalization of the treated sections the tissue when used in combination with the angiogenic compositions/concentrations. In other embodiments, disclosed thalidomide analogs exhibiting TNF-α inhibitory activity can be combined with other TNF-α inhibitory agents, for example, steroids such as dexamethasone and prednisolone. When used for treatment of a cancer, the thalidomide analogs can be used in combination with chemotherapeutic agents and/or radiation and/or surgery.

Examples of other chemotherapeutic agents that can be used in combination with the disclosed thalidomide analogs include alkylating agents, antimetabolites, natural products, kinase inhibitors, hormones and their antagonists, and miscellaneous other agents. Examples of alkylating agents include nitrogen mustards (such as mechlorethamine, cyclophosphamide, melphalan, uracil mustard or chlorambucil), alkyl sulfonates (such as busulfan), and nitrosoureas (such as carmustine, lomustine, semustine, streptozocin, or dacarbazine). Examples of antimetabolites include folic acid analogs (such as methotrexate), pyrimidine analogs (such as 5-FU or cytarabine), and purine analogs, such as mercaptopurine or thioguanine. Examples of natural products include *vinca* alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Examples of kinase inhibitors include small molecule inhibitors (such as Iressa, Tarceva, PKI-166, CI-1033, CGP-5923A, EKB-569, TAK165, GE-572016, CI-1033, SU5416, ZD4190, PTK787/ZK222584, CGP41251, CEP-5214, ZD6474, BIBF1000, VGA1102, SU6668, SU11248, CGP-57148, tricyclic quinoxalines, SU4984, SU5406, Gleevec, NSC680410, PD166326, PD1173952, CT53518, GTP14564, PKC412, PP1, PD116285, CGP77675, CGP76030, CEP-701, and CEP2583), ligand modulators (such as Bevacizumanb, MV833, Soluble Flt-1 and Flk-1, VEGF Trap, GFB 116, NM3, VEGF 121-diptheria toxin conjugate and Interfereon-α), and monoclonal antibodies against receptors (such as Cetuximab, ABX-EGF, Y10, MDX-447, h-R3, EMD 72000, herceptin, MDX-H210, pertuzumab, IMC-1C11, and MF1). Examples of hormones and antagonists include adrenocorticosteroids (such as prednisone), progestins (such as hydroxyprogesterone caproate, medroxyprogesterone acdtate, and magestrol acetate), estrogens (such as diethylstilbestrol and ethinyl estradiol), antiestrogens (such as tamoxifen), and androgens (such as testerone proprionate and fluoxymesterone). Examples of miscellaneous agents include platinum coordination complexes (such as cis-diamine-dichloroplatinum II, which is also known as cisplatin), substituted ureas (such as hydroxyurea), methyl hydrazine derivatives (such as procarbazine), vaccines (such as APC8024), AP22408, B43-genistein conjugate, paclitaxel, AG538, and adrenocrotical suppressants (such as mitotane and aminoglutethimide). In addition, the disclosed thalidomide analogs can be combined with gene therapy approaches, such as those targeting VEGF/VEGFR (including antisense oligonucleotide therapy, Adenovirus-based Flt-1 gene therapy, Retrovirus-base Flk-1 gene therapy, Retrovirus-based VHL gene therapy, and angiozyme) and IGF-1R (including INX-4437). Examples of the most commonly used chemotherapy drugs that can be used in combination with the disclosed tricyclic compounds agent include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol, Velban, Vincristine, VP-16, Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

The disclosed thalidomide analogs also can be combined with radiotherapy employing radioisotopes (such as $^{32}$P, $^{90}$Y, $^{125}$I, $^{131}$I, and $^{177}$Lu), particle beams (such as proton, neutron and electron beams) and electromagnetic radiation (such as gamma rays, x-rays and photodynamic therapy using photosensitizers and visible or ultraviolet rays).

In some embodiments, the second therapeutic agent is an anti-inflammatory agent. Exemplary anti-inflammatory agents include non-steroidal anti-inflammatory drugs (NSAIDs) such as ibuprofen, ketoprofen, piroxicam, naproxen, sulindac, aspirin, choline subsalicylate, diflunisal, fenoprofen, indomethacin, meclofenamate, salsalate, tolmetin, ketorolac, flurbiprofen, and magnesium salicylate.

IV. Kits

Kits are also a feature of this disclosure. Embodiments of the kits include at least one thalidomide analog as disclosed herein. In some embodiments, the kits also include at least one solution in which the thalidomide analog may be dissolved or suspended. In one embodiment, the solution is suitable for directly dissolving or suspending the thalidomide analog. In an independent embodiment, the solution is provided as a concentrated solution, which is subsequently diluted prior to use. The solution may be a pharmaceutically acceptable carrier. The kits also may include one or more containers, such as a disposable test tube or cuvette. In certain embodiments, the thalidomide analog is premeasured into one or more containers (e.g., test tubes, cuvettes, or ampules). The kits may further include instructions for using the thalidomide analog.

V. Examples

Thalidomide analogs disclosed herein have not yet undergone regulatory review for use in humans
Materials and Methods:
Zebrafish Embryology:
The use of zebrafish embryo (*Danio rerio*) bioassays as a preclinical model in the classification of novel compounds has increased in recent years due to several factors including; low cost, ease of maintenance, speed of embryonic development, transparency of the embryos and genetic conservation between zebrafish and humans (Howe et al., Nature 2013; 496:498; Therapontos et al., *PNAS* 2009, 106:8573; Mahony et al., *PNAS* 2013, 110:12703; Beedie et al., *Oncotarget* 2016, 7(22):33237; Beedie et al., *Mol. Cancer Ther.* 2015, 14(10):2228). Two established zebrafish reporter lines were used—the fli1:EGFP line, where the fli1 promoter drives expression of enhanced green fluorescent protein within the developing vasculature (Lawson et al., 2002), and the Tg(mpo::EGFP) line (also known as mpo: GFP), which expresses green fluorescent protein via the neutrophil specific myeloperoxidase promoter (Renshaw et al., *Blood* 2006, 108:3976). The use of these zebrafish transgenic reporter lines allows for the identification of potential anti-angiogenic and anti-inflammatory compounds respectively, and both have been used previously to successfully classify the action of thalidomide analogs (Therapontos et al., 2009; Mahony et al., 2013; Beedie et al., *Oncotarget* 2016, 7(22):33237; Beedie et al., *Mol. Cancer Ther.* 2015, 14(10):2228). Zebrafish embryos were treated with analogs as previously described (Mahony et al., 2013). Briefly, fli1:EGFP embryos were collected and embryos were allowed to develop for 24 hours. Embryos were dechorionated manually and exposed to test compounds or vehicle control for a further 24 hours, imaged and analyzed for intersegmental vessel (ISV) growth. At 24 hours post fertilisation (hpf) the ISVs were ideal to study to visualize and analyze the actions of compounds on angiogenesis. At this time point ISVs were rapidly forming beneath the developing head, over the body and had yet to form in the tail (Lawson and Weinstein, *Developmental Biology* 2002, 248:307; Therapontos and Vargesson, *Developmental Dynamics* 2010, 239:2761). Additionally, these sprouts would go on to form the bilateral dorsal longitudinal anastomotic vessels. By treating before this fusion and formation occurs, the effect of each compound on the individual vessels as well as overall patterning structural integrity (Isogai et al., *Development* 2003, 130:5281) could be determined. Tg(mpo::EGFP) were tail fin clipped as previously detailed (Renshaw et al., 2006; Mahony et al., 2013; Beedie et al., *Oncotarget* 2016, 7(22):33237; Beedie et al., *Mol. Cancer Ther.* 2015, 14(10):2228) and incubated with test compounds or vehicle control at 72 hours post fertilization. Fish were imaged at 24 hours and the number of migratory neutrophils present at the wound site were counted. Compounds inducing an at least 50% reduction of neutrophils to the wound site were considered to have anti-inflammatory properties in this system. All larvae were assessed for viability and morphological integrity.
Chicken Embryology:
Fertilized white leghorn chicken embryos were incubated at 38° C. and staged according to Hamburger and Hamilton (HH) stages of development (1951). Embryos were tested at HH stage 17-18 (day 2.5). Following membrane removal, test compounds or vehicle control solutions were applied globally over the embryo. The eggs were sealed and the development of the embryos was monitored up to HH stage 30 (E9).

Thalidomide Analogs:

Compounds were dissolved in DMSO, and stored between 10-200 mg/mL, and used at a final working DMSO concentration of 0.1%. The chemical structures of lead compounds of interest were confirmed by chemical characterization (purity >99.5%) and are shown in Tables 2-5. The concentrations used to attain the data presented are given in Table 6; all compounds were screened across a range of concentrations from 1-200 µg/mL.

Imaging and Analysis:

Imaging was performed using a Nikon MZ1500 fluorescent stereomicroscope with a Nikon DS-5 digital camera, and analyzed using Adobe Photoshop and Image J. Analysis was conducted using Prism 6.0 (GraphPad Software, La Jolla, Calif.) and statistical significance was assessed using two-tailed Student's t tests or ANOVA analyses.

Example 1

Compound Synthesis

Figure 1:
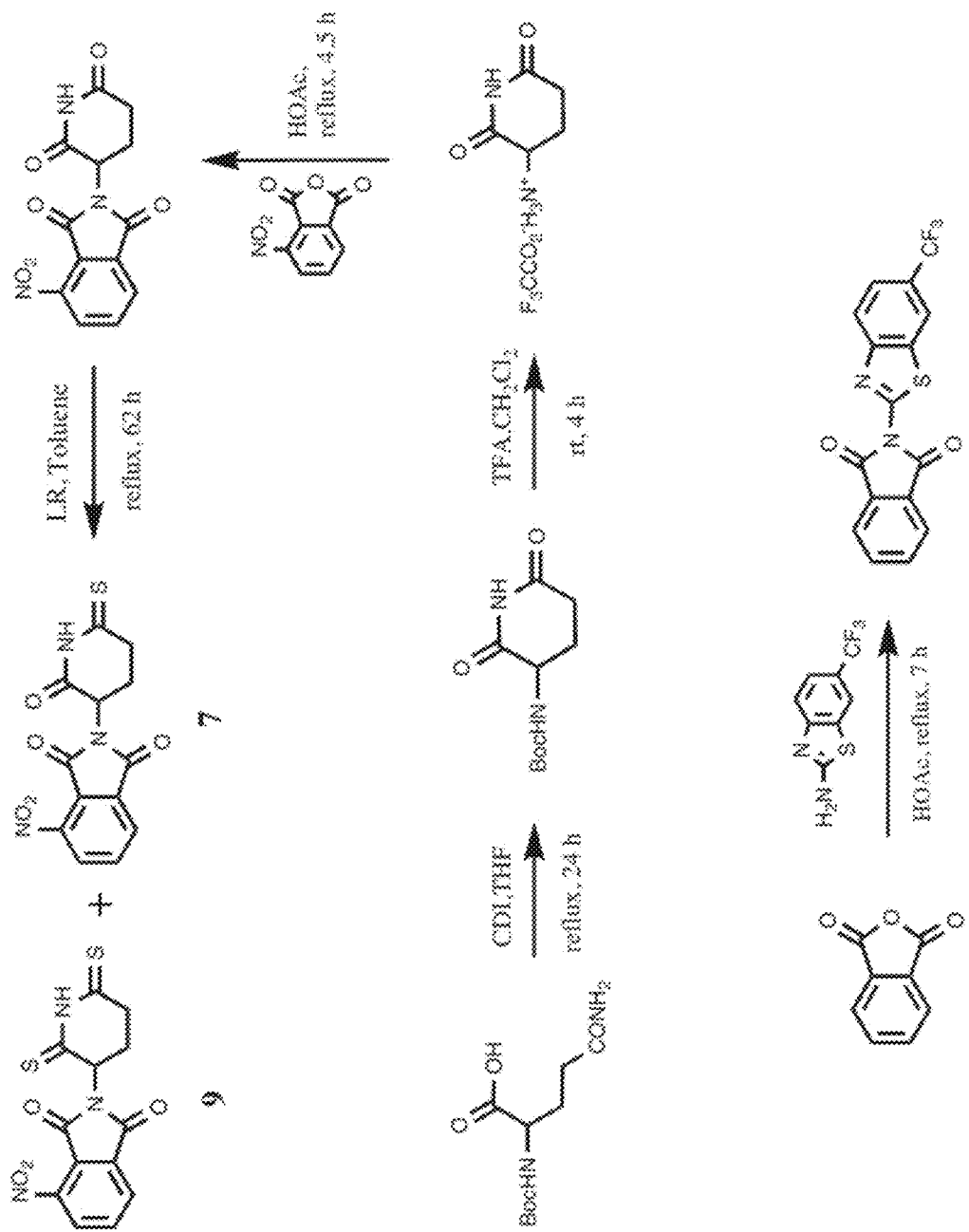
FIG. 1 shows exemplary synthetic schemes for making substituted phthalimides (thalidomide analogs).
Figure 2:
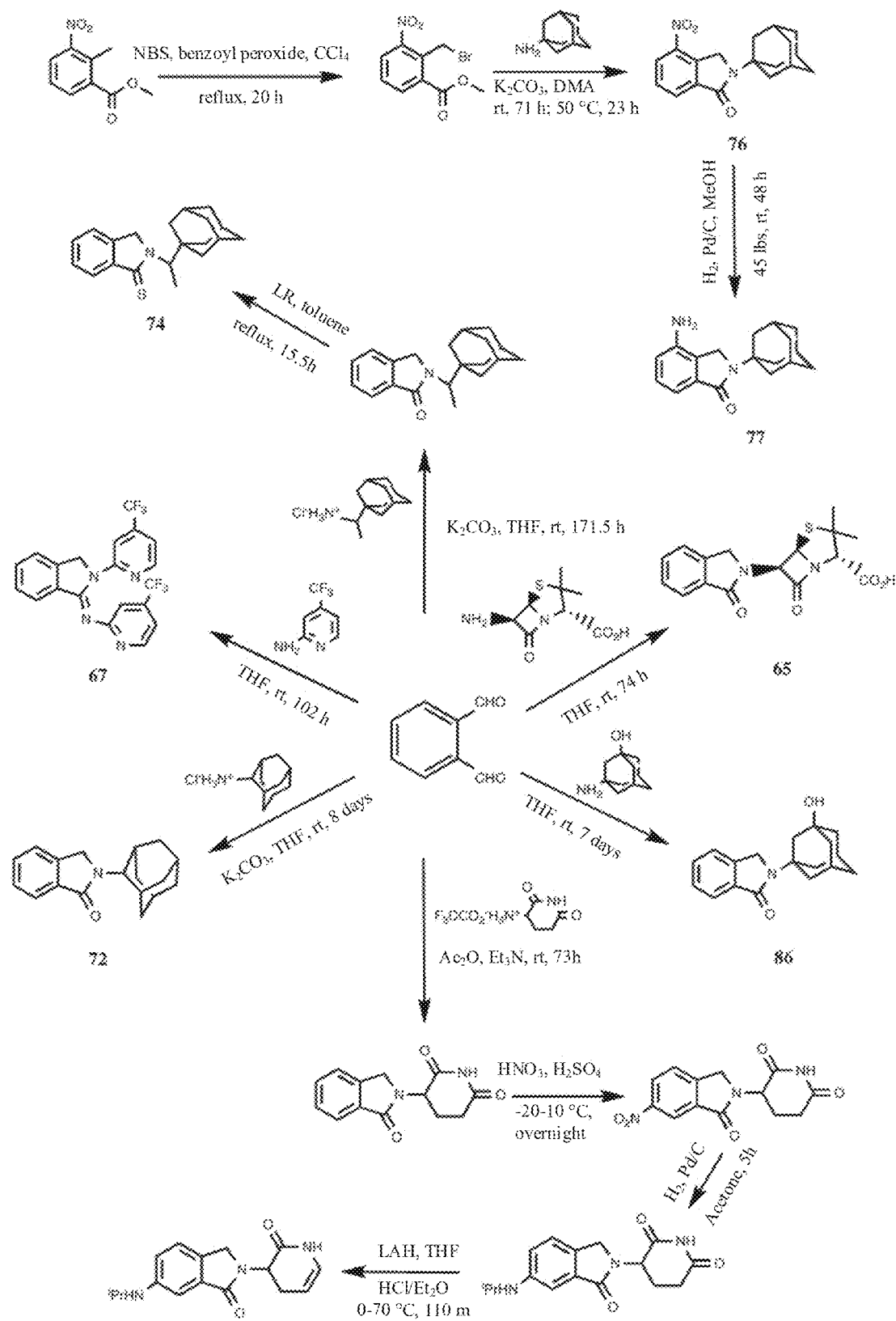
FIG. 2 shows additional exemplary synthetic schemes for making substituted phthalimidines.

Exemplary syntheses are provided. Exemplary synthetic schemes are shown in FIGS. 1 and 2.

2-(2-Oxo-6-thioxo-3-piperidinyl)-4-nitro-1H-isoindole-1,3(2H)-dione (7) and 2-(2,6-Dithioxo-3-piperidinyl)-4-nitro-1H-isoindole-1,3(2H)-dione (9)

A mixture of 4-nitrothalidomide (412.0 mg, 1.359 mmol) and Lawesson reagent (1.21 g, 2.992 mmol) in toluene (200 mL) was stirred for 62 hours under an atmosphere of nitrogen at reflux temperature. After removing solvent, the residues were separated with chromatography on silica gel (EA/PE=1/2) to afford product 7 (134.6 mg, 62.0%) and product 9 (105.6 mg, 46.3%).

Compound 7 (yellow solid): mp 233.5-236.3° C.; $^1$H NMR (DMSO-$d_6$) δ 12.66 (s, 1H, NH), 8.33 (d, J=8.2 Hz, 1H, C5-H), 8.22 (d, J=7.8 Hz, 1H, C7-H), 8.11 (t, J=8.2 Hz, 1H, C6-H), 5.32-5.27 (m, 1H, C3'-H), 3.24-3.12 (m, 2H, C4'-H) and 2.50-1.96 (m, 2H, C5'-H) ppm; $^{13}$C NMR (DMSO-$d_6$) δ 210.9, 167.2, 165.5, 162.8, 144.9, 137.3, 133.4, 129.3, 127.8, 123.0, 49.7, 41.1 and 23.8 ppm; MS (CI/CH$_4$), m/z 319 (M$^+$).

Compound 9 (red-brown solid): mp 200.5-202.0° C.; $^1$H NMR (DMSO-$d_6$) δ 13.82 (s, 1H, NH), 8.33 (d, J=7.8 Hz, 1H, C5-H), 8.23 (d, J=7.4 Hz, 1H, C7-H), 8.11 (t, J=7.8 Hz, 1H, C6-H), 5.37-5.32 (m, 1H, C3'-H), 3.35-2.80 (m, 2H, C4'-H) and 2.70-2.12 (m, 2H, C5'-H); $^{13}$C NMR (DMSO-$d_6$) δ 206.6, 201.2, 165.5, 162.9, 144.9, 137.3, 133.5, 129.3, 127.8, 123.0, 56.9, 41.8 and 23.7 ppm; MS (CI/CH$_4$), m/z 335 (M$^+$).

6-Isopropylamino-2-(3,4-dihydro-2-pyridone-3-yl) phthalimidine (46)

A mixture of 6-isopropylamino-2-(2,6-dioxo-3-piperidinyl)-phthalimidine hydrochloride (600 mg, 1.776 mmol) and lithium aluminum hydride (177.0 mg, 4.664 mmol) in tetrahydrofuran (120 mL) was reacted for 80 minutes under an atmosphere of nitrogen in an ice bath. Thereafter, hydrogen chloride in diethyl ether (1.0 M, 18 mL) was added at the same temperature and was reacted for another 10 minutes. Acetic anhydride (2.7 mL) was added to the reactive system at 0° C., which was then gradually raised to room temperature and thereafter heated to reflux for 20 minutes. After processing, the residues were isolated by chromatography on silica gel (CH$_2$Cl$_2$/MeOH=25/1) to afford product 46 (46.1 mg, 18.2%) as a gum: $^1$H NMR (DMSO-$d_6$) δ 9.40 (s, 1H, NH), 7.70-7.35 (m, 3H, Ar—H), 6.05-5.95 (m, 1H, C6'-H), 5.12-5.03 (m, 1H, C5'-H), 4.95-4.75 (m, 2H, NH and C3'-H), 4.52 and 4.50 (AB system, J=17.8 Hz, 2H, C3-H) and 2.85-1.88 (m, 2H, C4'-H), 1.57 (s, 1H, Me$_2$CH) and 1.01-0.83 (m. 6H, CH$_3$CCH$_3$) ppm; $^{13}$C NMR (DMSO-$d_6$) δ 168.7, 167.7, 142.3, 139.2, 134.2, 133.3, 126.0, 124.8, 109.5, 103.3, 50.8, 47.3, 45.3, 25.0, 23.7 and 21.1 ppm; MS (CI/CH$_4$), m/z 285 (M$^+$).

2-(6-Trifluoromethyl-benzothiazol-2-yl)-1H-isoindole-1,3(2H)-dione (59)

A mixture of phthalic anhydride (0.339 g, 2.289 mmol) and 2-amino-6-trifluoromethyl benzothiazole (0.5 g, 2.291 mmol) in acetic acid (20 mL) was refluxed for 7 hours under an atmosphere of nitrogen. After removing solvent, the residues were recrystallized with acetone to afford product 59 (431.0 mg, 54.1%) as white needle crystals: mp 279.0-281.5° C.; $^1$H NMR (DMSO-$d_6$) δ 8.70 (s, 1H, C7'-H). 8.23 (d, 1H, C4'-H), 8.12-8.09 (m, 2H, C5,6-H), 8.02-7.99 (m, 2H, C4,7-H) and 7.88 (d, 1H, C5'-H); $^{13}$C NMR (DMSO-$d_6$) δ 168.7, 160.0, 155.9, 140.1, 137.1, 135.4, 130.0, 129.5, 128.7, 127.6, 127.3 and 124.5 ppm; MS (CI/CH$_4$), m/z 348 (M$^+$).

(1)-(2S,5R,6R)-3,3-Dimethyl-7-oxo-6-(1-oxo-1,3-dihydro-1H-isoindol-2-yl)-4-thia-1-azabicyclo[3.2.0] heptane-2-carboxylic acid (65)

A mixture of phthaldialdehyde (1.34 g, 10.0 mmol) and (+)-6-aminopenicilanic acid (2.16 g, 10.0 mmol) in tetrahydrofuran (300 mL) was stirred for 74 hours under an atmosphere of nitrogen at room temperature. After removing solvent, the residues were recrystallized with acetone to afford product 65 (416.0 mg, 12.5%) as a yellowish solid: mp 197.5-199.5° C.; $^1$H NMR (DMSO-$d_6$) δ 7.80-7.50 (m, 4H, Ar—H), 5.93 (s, 1H, C6'-H), 5.68 (s, 1H, C5'-H), 4.91 and 4.68 (AB system, J=16.5 Hz, 2H, C3-H), 4.42 (s, 1H, C2'-H), 1.70 (s, 3H, CH$_3$) and 1.51 (s, 3H, CH$_3$) ppm; $^{13}$C NMR (DMSO-$d_6$) δ 176.1, 173.2, 172.0, 146.7, 136.6, 134.7, 132.6, 128.2, 127.5, 74.7, 71.4, 69.1, 65.1, 54.5, 35.0 and 31.1 ppm; MS (CI/CH$_4$), m/z 334 (M++2).

N-(4-Trifluoromethylpyridin-2-yl)-1-imino(4-trifluoromethylpyridin-2-yl)-isoindoline (67)

A mixture of phthaldialdehyde (41.4 mg, 0.308 mmol) and 4-trifluoromethyl-2-aminopyridine (50 mg, 0.308 mmol) in tetrahydrofuran (10 mL) was stirred for 102 hours under an atmosphere of nitrogen at room temperature. After removing solvent, the residues were separated with chromatography on silica gel (EA/Hex=1/3) to afford product 67 (31.0 mg, 47.7%) as a gum: $^1$H NMR (CDCl$_3$) δ 9.30-6.40 (m, 10H, Pht-H, Py-H) and 5.26 (s, 2H, C3-H) ppm; $^{13}$C NMR (CDCl$_3$) δ 162.4, 155.1, 153.3, 150.1, 148.5, 141.0, 140.6, 139.9, 139.6, 131.8, 130.3, 127.7, 125.8, 124.3, 123.8, 123.4, 114.1, 110.9 and 52.4 ppm; MS (CI/CH$_4$), m/z 422 (M$^+$).

2,3-Dihydro-2-(tricyclo[3.3.1.1$^{3,7}$]dec-2-yl)-1H-isoindol-1-one (72)

A mixture of phthaldialdehyde (134.1 mg, 1.0 mmol), 2-adamantylamine hydrochloride (187.7 mg, 1.0 mmol) and potassium carbonate (76 mg, 0.549 mmol) in tetrahydrofuran (70 mL) was stirred for 8 days under an atmosphere of nitrogen at room temperature. After removing solvent, the residues were purified with chromatography on silica gel MeOH/CH$_2$Cl$_2$=1/12) to afford product 72 (166.0 mg, 62.1%) as white needle crystals: mp 121.5-123.0° C.; $^1$H NMR (CDCl$_3$) δ 7.83 (d, J=7.7 Hz, 1H, C7-H), 7.54-7.41 (m, 3H, Ar—H), 4.67 (s, 2H, C3-H), 4.34 (s, 1H, C2'-H) and 2.49-1.71 (m, 14H, Ad-H) ppm; $^{13}$C NMR (CDCl$_3$) δ 169.3, 141.6, 133.0, 131.0, 127.8, 123.3, 122.4, 58.3, 50.3, 38.2, 37.8, 32.7, 31.7, 27.6 and 27.3 ppm; MS (CI/CH$_4$), m/z 267 (M$^+$).

2,3-Dihydro-2-[1-(1-tricyclo[3.3.1.1$^{3,7}$]dec-1-yl)ethyl]-1H-isoindol-1-thione (74)

A mixture of 2,3-dihydro-2-[1-(1-tricyclo[3.3.1.1$^{3,7}$]dec-1-yl)ethyl]-1H-isoindol-1-one (100 mg, 0.339 mmol) and Lawesson reagent (75.2 mg, 0.186 mmol) in toluene (18 mL) was stirred for 15.5 hours under an atmosphere of nitrogen at reflux temperature. After removing solvent, the residues were purified with chromatography on silica gel (EA/Hex=1/3) to afford product 74 (60.3 mg, 57.3%) as a yellow solid: mp 199.0-200.5° C.; $^1$H NMR (DMSO-d$_6$) δ 7.85 (d, J=7.6 Hz, 1H, C7-H), 7.61-7.47 (m, 3H, Ar—H), 5.06 (q, J=7.1 Hz, 1H, NCHMeAd), 4.86 (s, 2H, C3-H), 1.97-1.47 (m, 15H, Ad-H) and 1.21 (d, J=7.1 Hz, 3H, CH$_3$) ppm; $^{13}$C NMR (DMSO-d$_6$) δ 192.9, 141.1, 139.4, 131.7, 128.4, 125.5, 123.0, 59.7, 55.5, 39.3, 37.7, 36.8, 28.4 and 12.8 ppm; MS (CI/CH$_4$), m/z 309 (M-2); Anal. calcd for C$_{20}$H$_{25}$NS: C, 77.12; H, 8.09; N, 4.50. Found: C, 76.83; H, 8.03; N, 4.38.

2,3-Dihydro-4-nitro-2-(tricyclo[3.3.1.1$^{3,7}$]dec-1-yl)-1H-isoindol-1-one (76)

A mixture of methyl 2-methyl-3-nitrobenzoate (18.7 g, 95.8 mmol), N-bromosuccinimide (17.1 g, 96.1 mmol) and benzoyl peroxide (0.7 g, 2.9 mmol) in carbon tetrachloride (500 mL) was refluxed for 20 hours. The reaction mixture was cooled and concentrated. Thereafter, it was precipitated and washed with diethyl ether to afford methyl 2-bromomethyl-3-nitrobenzoate (22.3 g, 84.8%) as yellowish crystals: mp 68.0-70.0° C. (lit. 67.0-70.0° C.). A mixture of this compound (362.4 mg, 1.322 mmol), 1-adamantylamine (200 mg, 1.322 mmol) and potassium carbonate (186.4 mg, 1.349 mmol) in DMA (2 mL) was stirred for 71 hours under an atmosphere of nitrogen at room temperature, and then continuously reacted for 23 hours at 50° C. After removing solvent, the residues were purified with chromatography on silica gel (EA/Hex=1/3) to afford product 76 (224.8 mg, 54.4%) as a yellowish solid: mp 214.0-215.5° C.; $^1$H NMR (CDCl$_3$) δ 8.37 (d, J=7.6 Hz, 1H, C7-H), 8.12 (d, J=7.6 Hz, 1H, C5-H), 7.66 (t, J=7.6 Hz, 1H, C6-H), 4.93 (s, 2H, C3-H) and 2.43-1.73 (m, 15H, Ad-H) ppm; $^{13}$C NMR (CDCl$_3$) δ 166.1, 143.2, 138.0, 136.5, 129.6, 129.4, 126.2, 56.2, 48.6, 40.0, 36.2, and 29.6 ppm; MS (CI/CH$_4$), m/z 312 (M$^+$).

2,3-Dihydro-4-amino-2-(tricyclo[3.3.1.1$^{3,7}$]dec-1-yl)-1H-isoindol-1-one (77)

A mixture of compound 76 (100 mg, 0.320 mmol) and palladium on carbon (10 wt. %, 152.8 mg) in methanol (117 mL) was shaken for 48 hours under an atmosphere of hydrogen (45 lbs) at room temperature. After removing solvent, the residue was purified with chromatography on silica gel (MeOH/CH$_2$Cl2=1/25) to afford product 77 (88.8 mg, 98.2%) as a yellowish solid: mp 228.0-229.5° C.; $^1$H NMR (DMSO-d$_6$) δ 7.08 (t, J=7.6 Hz, 1H, C6-H), 6.75 (d, J=7.8 Hz, 1H, C7-H), 6.68 (d, J=7.7 Hz, 1H, C5-H), 5.31 (s, 2H, NH$_2$), 4.27 (s, 2H, C3-H) and 2.21-1.67 (m, 15H, Ad-H) ppm; $^{13}$C NMR (DMSO-d$_6$) δ 168.8, 143.7, 135.1, 128.9, 125.7, 115.9, 110.1, 54.8, 46.0, 38.3, 36.4 and 29.5 ppm; MS (CI/CH$_4$), m/z 283 (M++1).

2,3-Dihydro-2-(tricyclo[3.3.1.1$^{3,7}$]dec-1-hydroxy-3-yl)-1H-isoindol-1-one (86)

A mixture of phthaldialdehyde (134.1 mg, 1.0 mmol) and 3- amino-1-adamantanol (167.3 mg, 1.0 mmol) in tetrahydrofuran (45 mL) was stirred for 7 days under an atmosphere of nitrogen at room temperature. After removing solvent, the residue was purified with chromatography on silica gel (MeOH/EA/PE=1/3/9) to afford product 86 (115.0 mg, 40.6%) as white needle crystals: mp 218.5-219.5° C.; $^1$H NMR (CDCl$_3$) δ 7.81-7.36 (m, 4H, Ar—H), 4.47 (s, 2H, C3-H) and 2.40-1.55 (m, 15H, OH, Ad-H) ppm; $^{13}$C NMR (CDCl$_3$) δ 168.9, 140.8, 134.3, 131.0, 127.9, 123.3, 122.4, 69.2, 57.8, 47.7, 44.1, 38.7, 34.9 and 30.8 ppm; MS (CI/CH$_4$), m/z 284 (M++1).

Example 2

Figure 3:
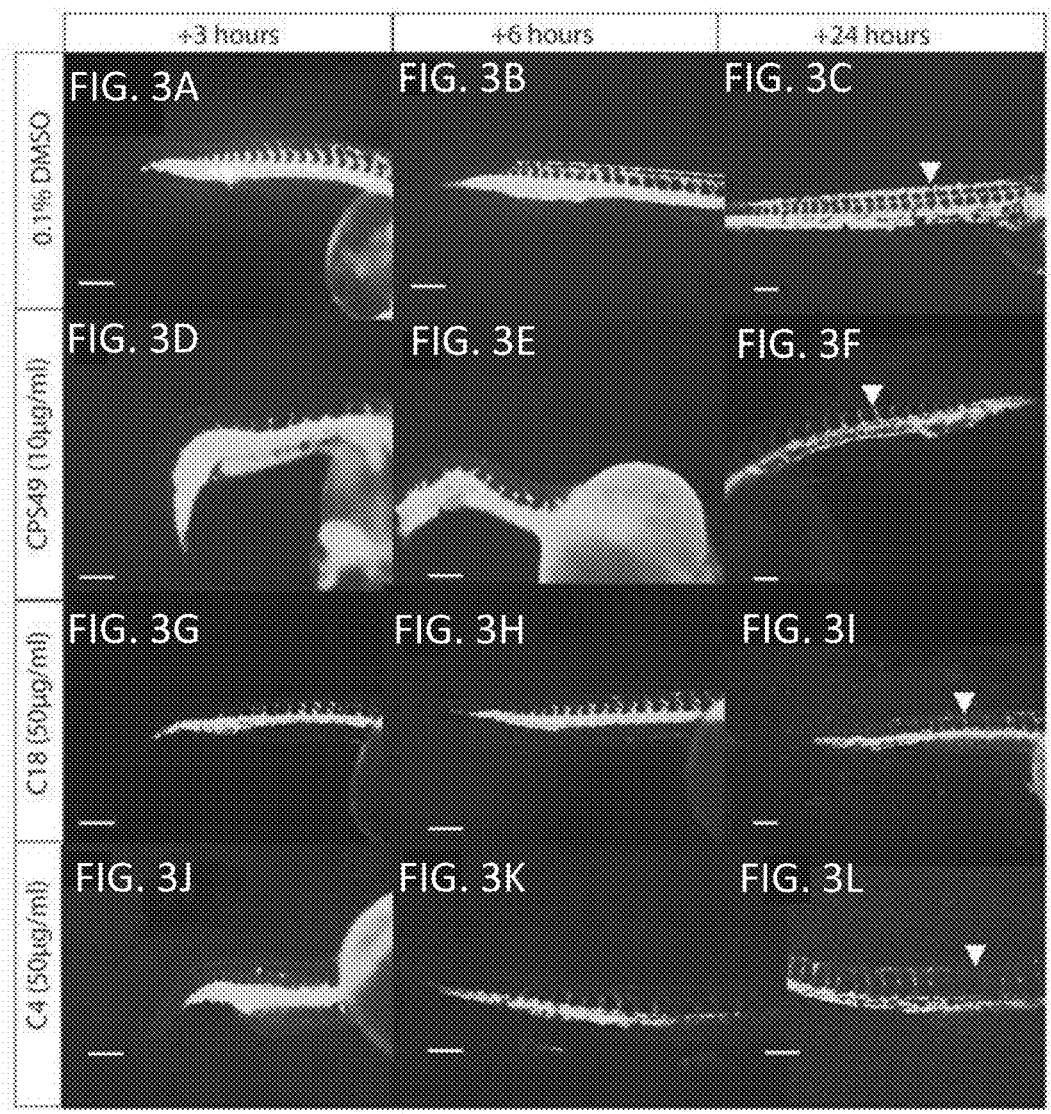
FIGS. 3A-3L are photomicrographs of fil1:EGFP zebrafish after incubation with vehicle or compounds for 3, 6, or 24 hours. The compounds were added at 24 hours post fertilization (hpf) and images were obtained at 48 hpf (i.e., 24 hours post drug administration). In comparison to control zebrafish (FIGS. 3A-3C) that show normal patterning of the intersegmental vessels (FIG. 3C, white arrow), treated and responsive zebrafish show a decrease in blood vessel length (FIG. 3F, white arrow) and loss of vascular connectivity or a decrease in the number of forming blood vessels (positive control CPS49, FIGS. 3D-3F). The examples shown are representative of treatment with compound 18 (50 μg/mL, FIGS. 3G-3I) and compound 4 (50 μg/mL, FIGS. 3J-3L).
Figure 4:
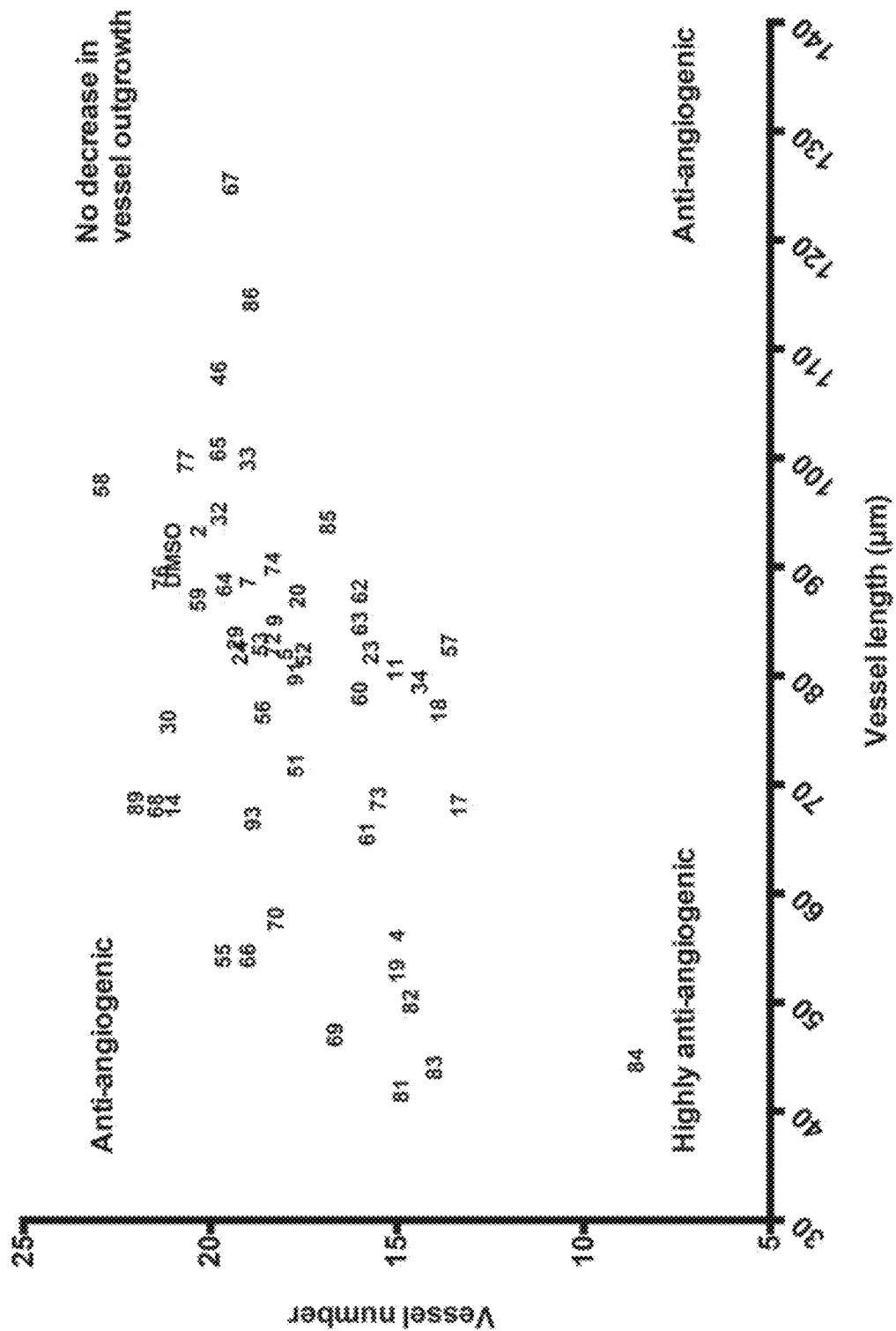
FIG. 4 is a graph of vessel number versus vessel length demonstrating the anti-angiogenic activity of each compound in fil1:EGFP zebrafish embryos.

Effect of Thalidomide Analogs on In Vivo Angiogenesis in Fli1:EGFP Zebrafish Embryos To determine if the thalidomide analogs had any effect on angiogenesis, fli1:EGFP embryos (Lawson and Weinstein, *Developmental Biology* 2002, 248:307-318) were exposed to either vehicle or a compound of interest, over a range of concentrations and over a range of time points starting at 24 hpf. Images were obtained at three time points over 24 hours after exposure to the compounds. The best concentration and time point were selected. CPS49, a compound that is chemically and structurally similar to thalidomide breakdown products, and is tetrafluorinated (which adds stability and bioactivity to the compound) and that causes severe limb defects in chicken embryos, was used as a positive control. The embryos were imaged at 48 hpf (FIGS. 3A3L) and analyzed for both vessel formation and the extent of growth of the vasculature. In comparison to control zebrafish that showed normal patterning of the intersegmental vessels, treated and responsive zebrafish showed a decrease in blood vessel length and loss of vascular connectivity or a decrease in the number of forming blood vessels. The information acquired was collated to define the overall impact upon angiogenesis and determine the relative anti-angiogenic activity of each compound (FIG. 4). In FIG. 4, the most highly anti-angiogenic compounds are in the lower left portion of the plot; the control (DMSO) lies in the midst of the scatter. Additionally the survival rates of the embryos were recorded as a percentage of the number of zebrafish alive following 24 hours of exposure to each compound. (Table 6). The potency of each compound varied. For example, compound 4 was highly anti-angiogenic at 1.5 μg/mL, whereas compound 51 showed activity at 200 μg/mL (Beedie et al., *Oncotarget* 2016, 7(22):33237). The results are based on the lowest concentration of each compound producing an effect; compounds not producing an effect are shown at the highest evaluated concentration (see Table 2 below).

Thirty-one compounds were anti-angiogenic as recorded by loss of ISVs or inhibition of ISV outgrowth in fli1:EGFP zebrafish. Of these compounds, 18 were found to exhibit no anti-inflammatory properties in the mpo:GFP inflammatory assay and thus were classified as having anti-angiogenic only properties in this in vivo assay (Table 2). The anti-angiogenic compounds were found to inhibit vessel outgrowth and/or the number of sprouting vessels at relatively low concentrations (1.5 µg/mL-200 µg/mL), similar to ranges used in other screening studies (Tweedie et al., *The Open Biochemistry Journal* 2011, 5:37; Mahony et al., 2013; Beedie et al., manuscript in press). However, some anti-angiogenic compounds were shown to induce death and defects within the treated embryos (see Example 3). The analogs with potent anti-angiogenic activity (for example, compound 4) also produced defects and high mortality rates in WT zebrafish and developing chicken embryo assays. This data complements other studies, which suggest the main cause of thalidomide induced birth defects may be primarily via a loss of correct patterning of the vasculature (Therapontos et al., PNAS 2009, 106:8573; Vargesson, *Birth Defects Research Part C: Embryo Today: Reviews* 2015, 105(2):140; Beedie et al., *Oncotarget* 2016, 7(22):33237).

TABLE 2

Compounds having only anti-angiogenic activity

| Cpd | Structure |
|---|---|
| 4 | 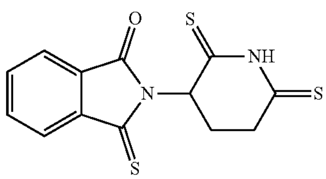 [SMILES: O=C1c2ccccc2C(=S)N1C1CCC(=S)NC1=S] |
| 11 | 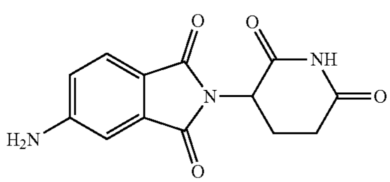 [SMILES: Nc1ccc2c(c1)C(=O)N(C1CCC(=O)NC1=O)C2=O] |
| 14 | 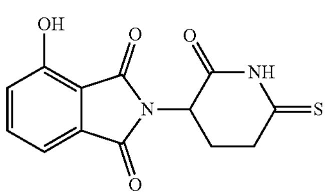 [SMILES: O=C1NC(=S)CCC1N1C(=O)c2cccc(O)c2C1=O] |
| 17 | 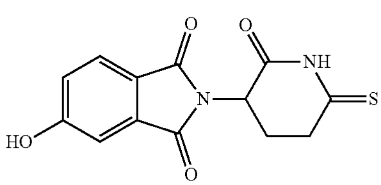 [SMILES: O=C1NC(=S)CCC1N1C(=O)c2ccc(O)cc2C1=O] |
| 19 | 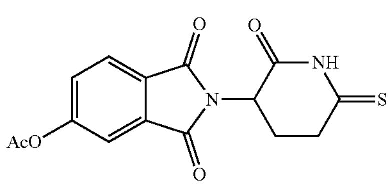 [SMILES: CC(=O)Oc1ccc2c(c1)C(=O)N(C1CCC(=S)NC1=O)C2=O] |

TABLE 2-continued

Compounds having only anti-angiogenic activity

| Cpd | Structure |
|---|---|
| 34 | 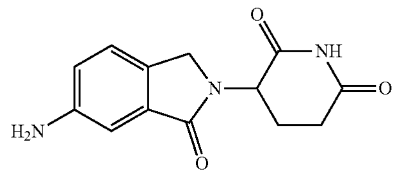 |
| 51 | 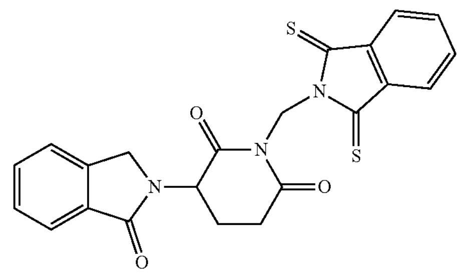 [SMILES: O=C1CCC(N2Cc3ccccc3C2=O)C(=O)N1CN1C(=S)c2ccccc2C1=S] |
| 55 | 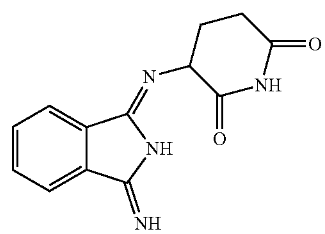 [SMILES: N=C1N/C(=N\C2CCC(=O)NC2=O)c2ccccc21] |
| 60 | 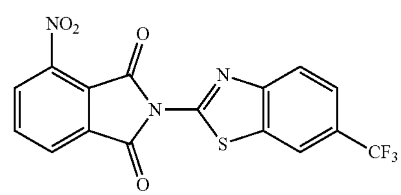 [SMILES: O=C1c2cccc([N+](=O)[O-])c2C(=O)N1c1nc2ccc(C(F)(F)F)cc2s1] |
| 69 | 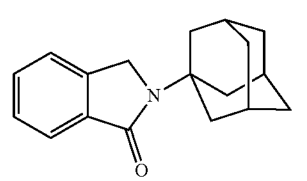 [SMILES: O=C1c2ccccc2CN1C12CC3CC(CC(C3)C1)C2] |
| 70 | 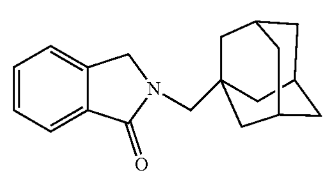 [SMILES: O=C1c2ccccc2CN1CC12CC3CC(CC(C3)C1)C2] |
| 73 | 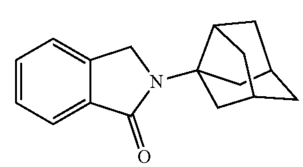 [SMILES: O=C1c2ccccc2CN1C12CC3CC(CC1C3)C2] |

TABLE 2-continued

Compounds having only anti-angiogenic activity

| Cpd | Structure |
|---|---|
| 81 | 4-NH₂, N-(1-adamantylethyl) isoindolin-1-one |
| 83 | 4-NH₂, N-(2-adamantyl) isoindolin-1-one |
| 84 | 4-NO₂, N-(1-adamantyl) isoindolin-1-one |
| 89 | 4-NO₂, N-(1-adamantylethyl) isoindoline-1-thione |
| 91 | 4-NH₂, N-(pinanyl) isoindolin-1-one |
| 93 | 4-NH₂, N-(pinanyl) isoindolin-1-one (diastereomer) |

Example 3

Figures 5A, 5B, 5C, 5D:
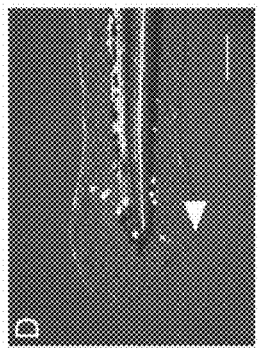
FIGS. 5A-5D are photomicrographs of zebrafish embryos transgenic for a fluorescently tagged neutrophil marker (Tg(mpo::GFP)) that were fin clipped at 72 hpf to induce an inflammatory response. Arrows indicate the edge of the cut; the scale bar is 100 μm.

Effect of Thalidomide Analogs on Neutrophil Migration in Response to Injury in Mpo:GFP Zebrafish To assess the immunomodulatory effects of the thalidomide analogs, the mpo:gfp transgenic zebrafish line (Renshaw et al., *Blood* 2006, 108:3976-3978) was utilized because it is an accepted model of inflammation, and can be used to test the effect of anti-inflammatory agents. These embryos express GFP-tagged myeloperoxidase, where green fluorescence marks the neutrophil cells involved in the inflammatory response process, for example following injury, from 72 hours post fertilization (Renshaw et al., 2006; Mahony et al., 2013; Beedie et al., *Oncotarget* 2016, 7(22):33237). At 72 hpf the dorsal third of the tail fin was removed and the embryos were immersed in the desired compound or vehicle (FIGS. 5A-5C). The embryos were examined for the effect on the inflammatory response quantified as an induction and migration of neutrophils to the wound site 24 hours later. Control embryos with tail fin cuts showed a high neutrophil response (FIG. 5A). In comparison to control embryos (FIG. 5A), compounds which did not exhibit anti-inflammatory properties (e.g., compound 51, 200 µg/mL) showed a similar number of neutrophils in the wound site (FIG. 5B). Compounds with anti-inflammatory properties (e.g., compound 20, 10 µg/mL; compound 58, 10 µg/mL) showed at least a 50% reduction of neutrophils to the wound site (FIGS. 5C, 5D).

Figure 6:
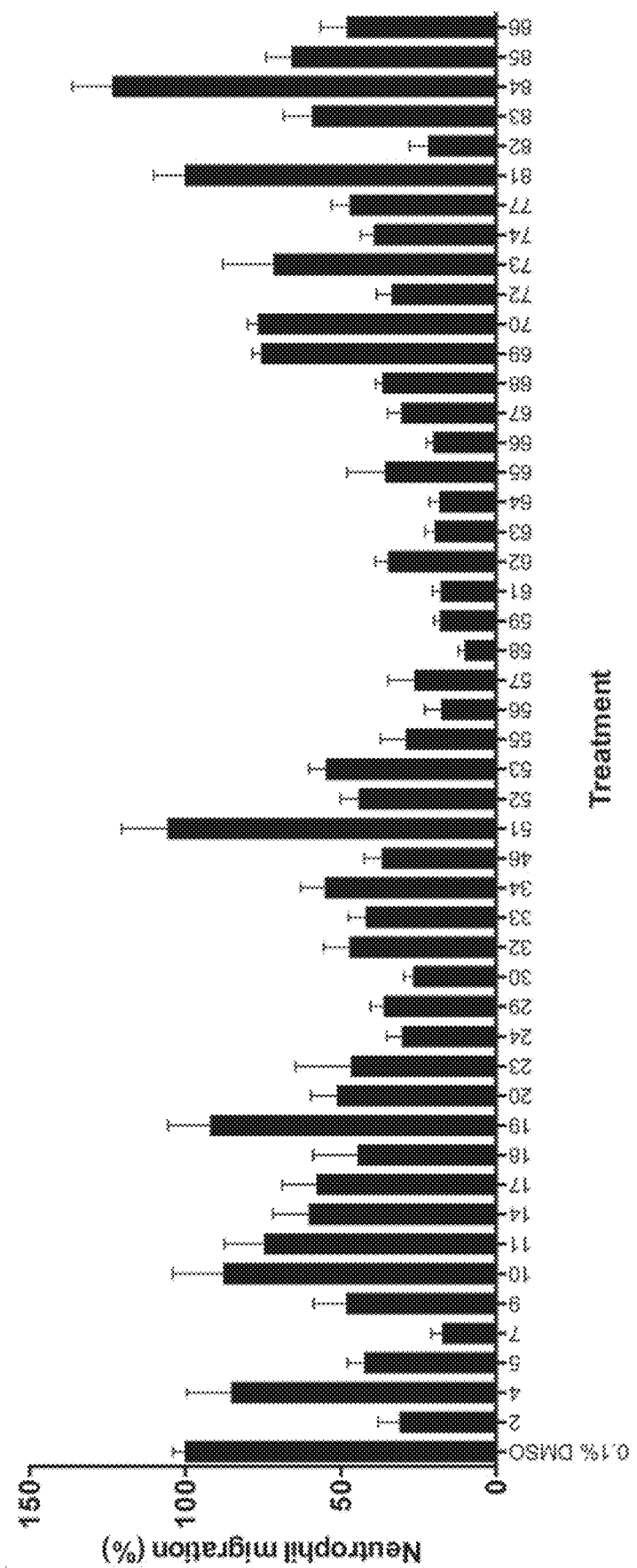
FIG. 6 is a graph quantifying the effects of thalidomide analogs on the inflammatory response in zebrafish embryos transgenic for a fluorescently tagged neutrophil marker (Tg(mpo::GFP)) that were fin clipped at 72 hpf to induce an inflammatory response. The scale bar represents 100 μm.

In total 21 compounds exhibited anti-inflammatory activity in this assay (FIG. 6), without anti-angiogenic effects (Table 3). Seven of the compounds were found to be teratogenic (see Example 4). Compound 58 was the most effective analog at inhibiting the inflammatory response (FIG. 6, Tables 3, 6). Compound 2 (2,3-dihydro-2-(2-oxo-6-thioxo-3-piperidinyl)-3-thioxo-1H-isoindol-1-one) also possessed significant anti-inflammatory action (Beedie et al., *Oncotarget* 2016, 7(22):33237).

TABLE 3

Compounds having only anti-inflammatory properties

| Cpd | Structure |
|---|---|
| 2 | phthalimide-N-(2-oxo-6-thioxopiperidin-3-yl), 3-thioxo |
| 5* | 4-NO₂ phthalimide-N-(2,6-dioxopiperidin-3-yl) |
| 7 | 4-NO₂ phthalimide-N-(2-oxo-6-thioxopiperidin-3-yl) |
| 9 | 4-NO₂ phthalimide-N-(2-thioxo-6-thioxopiperidin-3-yl) |
| 24* | 7-amino-benzoxazine-dione N-(2,6-dioxopiperidin-3-yl) |

TABLE 3-continued

Compounds having only anti-inflammatory properties

| Cpd | Structure |
|---|---|
| 29* | (structure) |
| 32* | (structure) |
| 33* | (structure) |
| 46 | (structure) |
| 53 | (structure) |
| 56 | (structure) |
| 58 | (structure) |
| 59 | (structure) |
| 64 | (structure) |
| 65 | (structure) |
| 67* | (structure) |
| 72 | (structure) |
| 74 | (structure) |
| 76* | (structure) |

TABLE 3-continued

Compounds having only anti-inflammatory properties

| Cpd | Structure |
|---|---|
| 77 | 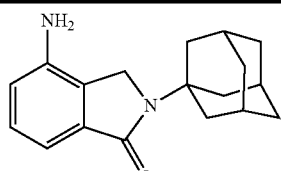 |
| 86 | 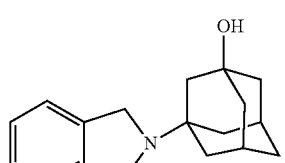 |

*Anti-inflammatory, but teratogenic in zebrafish and/or chicken embryo assay.

Thirteen compounds were anti-inflammatory and anti-angiogenic (Table 4). Given that tumors require a blood supply to survive, and that there are high levels of expression of cytokines in the tumor microenvironment (including Cyclooxygenase-2, TNF-α and interleukins), compounds targeting both blood vessel formation and mediators of the inflammatory response may be beneficial for anti-cancer therapy.

TABLE 4

Compounds with anti-angiogenic and anti-inflammatory activity

| Cpd | Structure |
|---|---|
| 18 | 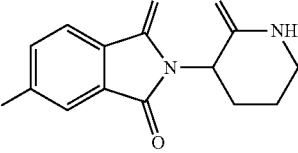 |
| 20 | 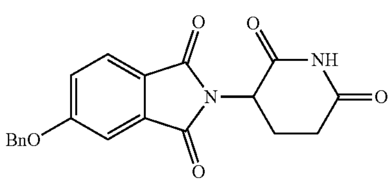 |
| 23 | 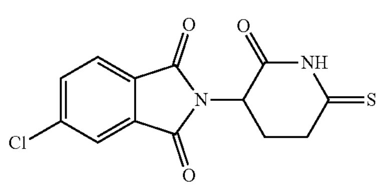 [SMILES: O=C1NC(=S)CCC1N1C(=O)c2ccc(Cl)cc2C1=O] |
| 30 | 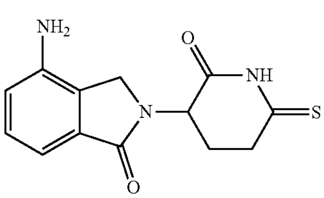 [SMILES: Nc1cccc2c1CN(C1CCC(=S)NC1=O)C2=O] |

TABLE 4-continued

Compounds with anti-angiogenic and anti-inflammatory activity

| Cpd | Structure |
|---|---|
| 52 | 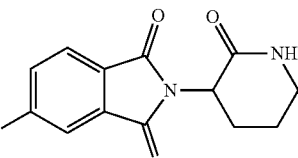 |
| 57 | 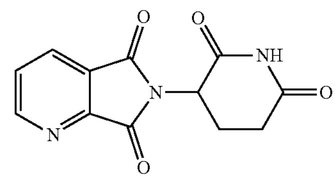 [SMILES: O=C1CCC(N2C(=O)c3cccnc3C2=O)C(=O)N1] |
| 61 | 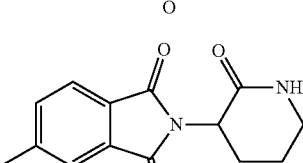 |
| 62 | 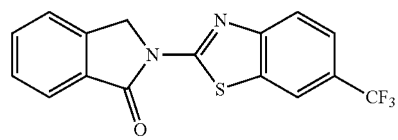 [SMILES: O=C1c2ccccc2CN1c1nc2ccc(C(F)(F)F)cc2s1] |
| 63 | 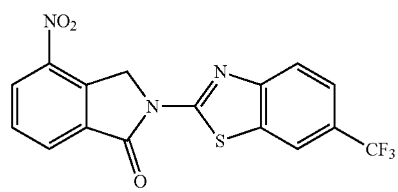 [SMILES: O=C1c2cccc([N+](=O)[O-])c2CN1c1nc2ccc(C(F)(F)F)cc2s1] |
| 66 | 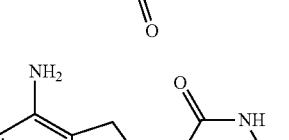 |
| 68 | 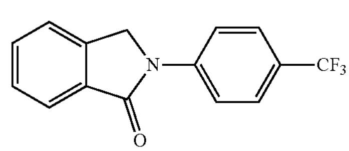 [SMILES: O=C1c2ccccc2CN1c1ccc(C(F)(F)F)cc1] |
| 82 | 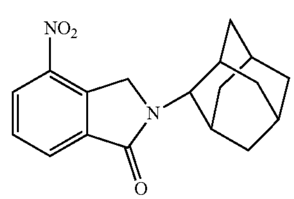 [SMILES: O=C1c2cccc([N+](=O)[O-])c2CN1C1C2CC3CC(C2)CC1C3] |

TABLE 4-continued

Compounds with anti-angiogenic and anti-inflammatory activity

| Cpd | Structure |
|---|---|
| 85 | 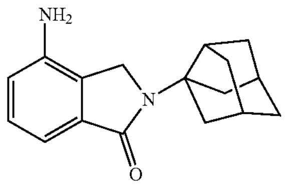 [SMILES: Nc1cccc2c1CN(C13CC4CC(CC1C4)C3)C2=O] |

Example 4

Teratogenicity in Embryonic Development

To determine the effects of the candidate compounds on embryonic development, two in vivo model systems (developing zebrafish and chicken embryos) were utilized. The results indicated that of the potential anti-inflammatory compounds, six had high mortality rates, and in surviving embryos treated with these compounds a teratogenic phenotype was produced.

When the compounds with anti-angiogenic activity were screened in these systems, all of the embryos exhibited high mortality rates. Malformations in the development of the zebrafish embryo were noted, including inhibition of eye, otic vesicle and fin development (FIGS. 7A-7F). In comparison to control wild type (WT) zebrafish (FIGS. 7A, 7B), an anti-angiogenic compound (compound 4) induced defects (e.g., microophthalmia and fin malformation) in the WT zebrafish (FIGS. 7C, 7D), a compound (compound 8) with no effect in the assays (FIGS. 7E, 7F) and an anti-inflammatory compound (compound 77) had no apparent effect on the development of the zebrafish embryo (FIGS. 7G, 7H). Embryos were screened at concentrations previously determined, in this study, to be anti-angiogenic or anti-inflammatory in the fli1:EGFP and mpo:GFP assays respectively.

Compounds of interest were screened in chicken embryos (FIGS. 7I-7P). FIG. 7I shows an embryo imaged in ovo with normal vasculature. Compound 23 caused constriction in the vasculature of the chorioallantoic membrane (white arrow) and necrosis (FIG. 7J). FIG. 7K shows a control embryo imaged ex ovo. FIG. 7M shows a normal eye. Teratogenicity in the chicken embryo included microophthalmia (FIG. 7L—compound 80), hemorrhaging throughout the body and head (FIG. 7L, FIG. 7N—compound 81), reduced body size (FIG. 7N), and limb and hand plate defects (FIG. 7P). FIG. 7O shows a control forelimb. Compounds exhibiting anti-angiogenic properties produced more defects than those possessing anti-inflammatory only properties. In particular, chicken embryos treated with these compounds often showed signs of hemorrhaging (e.g., compounds 80, 81) (FIGS. 7L, 7N) and constriction of the vasculature and necrosis in the surrounding chorioallantoic membrane (e.g., compound 23) (FIG. 7J). An embryo treated with compound 11 had missing digits in the hindlimb.

All of the anti-angiogenic compounds of Table 2 were shown to be teratogenic in the developing zebrafish and chick model systems. All of the compounds exhibiting both anti-angiogenic and anti-inflammatory properties (Table 4) also were shown to the teratogenic in the WT zebrafish and developing chick model systems.

Table 5 provides structures of compounds used in the foregoing examples. Table 6 provides concentrations and n numbers used in the foregoing examples that exhibited activity. Compounds exhibiting anti-angiogenic properties are shown at the lowest concentration producing a response. Compounds that did not produce a response in this assay are shown at the highest concentration tested, or the highest concentration where the survival rate was not affected. Compounds which significantly inhibited neutrophil migration to the wound site are shown at the lowest concentration with activity. Compounds that did not produce a response in this assay are shown at the highest concentration tested, or the highest concentration where the survival rate was not affected. Concentrations used in the WT zebrafish and chicken embryo assays to assess for teratogenesis, were equal to or higher than those utilized in the fli1:EGFP and mpo:GFP zebrafish assays

TABLE 5

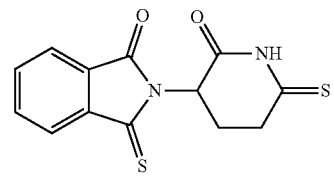 [SMILES: O=C1NC(=S)CCC1N1C(=O)c2ccccc2C1=S]

2: $C_{13}H_{10}N_2O_2S_2$ MW 290.36

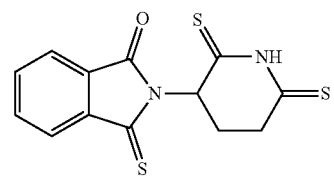

4: $C_{13}H_{10}N_2OS_3$ MW 306.43

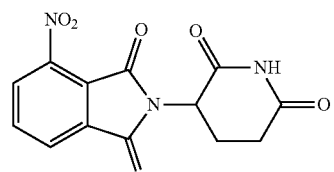

5: $C_{13}H_9N_3O_6$ MW 303.23

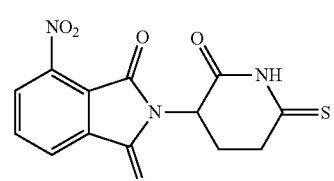

7: $C_{13}H_9N_3O_5S$ MW 319.29

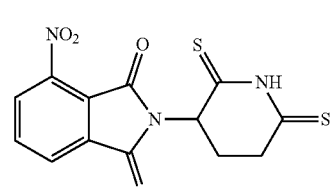

9: $C_{13}H_9N_3O_4S_2$ MW 335.36

TABLE 5-continued
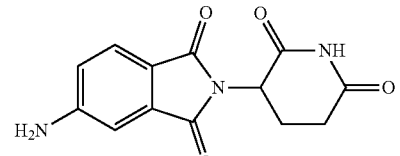
11: C$_{13}$H$_{11}$N$_3$O$_4$ MW 273.24
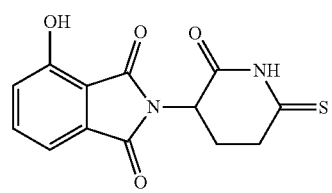 [SMILES: O=C1NC(=S)CCC1N1C(=O)c2cccc(O)c2C1=O]
14: C$_{13}$H$_{10}$N$_2$O$_4$S MW 290.29
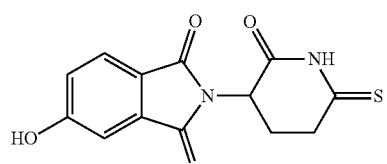
17: C$_{13}$H$_{10}$N$_2$O$_4$S MW 290.29
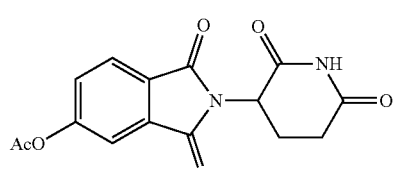
18: C$_{15}$H$_{12}$N$_2$O$_6$ MW 316.27
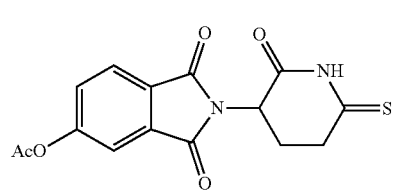 [SMILES: CC(=O)Oc1ccc2c(c1)C(=O)N(C1CCC(=S)NC1=O)C2=O]
19: C$_{15}$H$_{12}$N$_2$O$_5$S MW 332.33
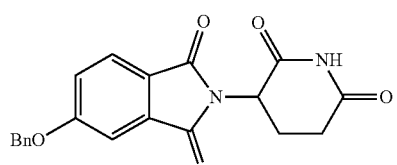
20: C$_{20}$H$_{16}$N$_2$O$_5$ MW 364.35
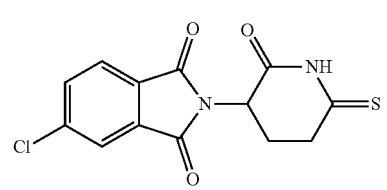 [SMILES: O=C1NC(=S)CCC1N1C(=O)c2ccc(Cl)cc2C1=O]
23: C$_{13}$H$_9$ClN$_2$O$_3$S MW 308.74
TABLE 5-continued
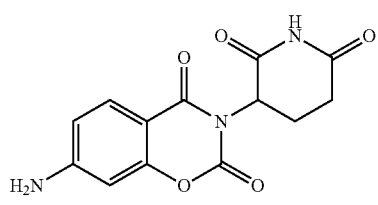 [SMILES: Nc1ccc2c(=O)n(C3CCC(=O)NC3=O)c(=O)oc2c1]
24: C$_{13}$H$_{11}$N$_3$O$_5$ MW 289.24
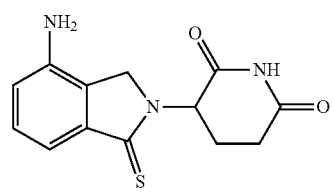 [SMILES: Nc1cccc2c1CN(C1CCC(=O)NC1=O)C2=S]
29: C$_{13}$H$_{13}$N$_3$O$_2$S MW 275.33
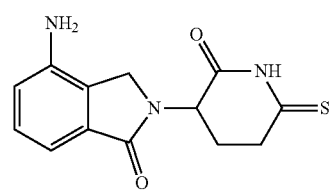
30: C$_{13}$H$_{13}$N$_3$O$_2$S MW 275.33
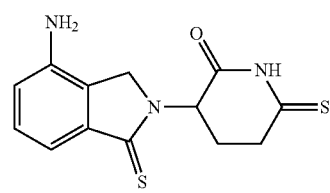 [SMILES: Nc1cccc2c1CN(C1CCC(=S)NC1=O)C2=S]
32: C$_{13}$H$_{13}$N$_3$OS$_2$ MW 291.39
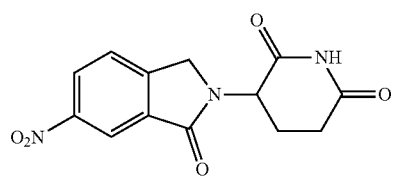
33: C$_{13}$H$_{11}$N$_3$O$_5$ MW 289.24
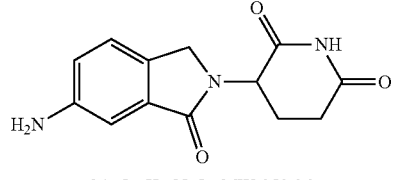 [SMILES: O=C1CCC(N2Cc3ccc([N+](=O)[O-])cc3C2=O)C(=O)N1]
34: C$_{13}$H$_{13}$N$_3$O$_3$ MW 259.26
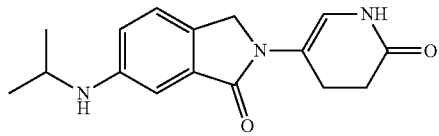 [SMILES: CC(C)Nc1ccc2c(c1)C(=O)N(C1=CNC(=O)CC1)C2]
45: C$_{16}$H$_{19}$N$_3$O$_2$ MW 285.34

TABLE 5-continued
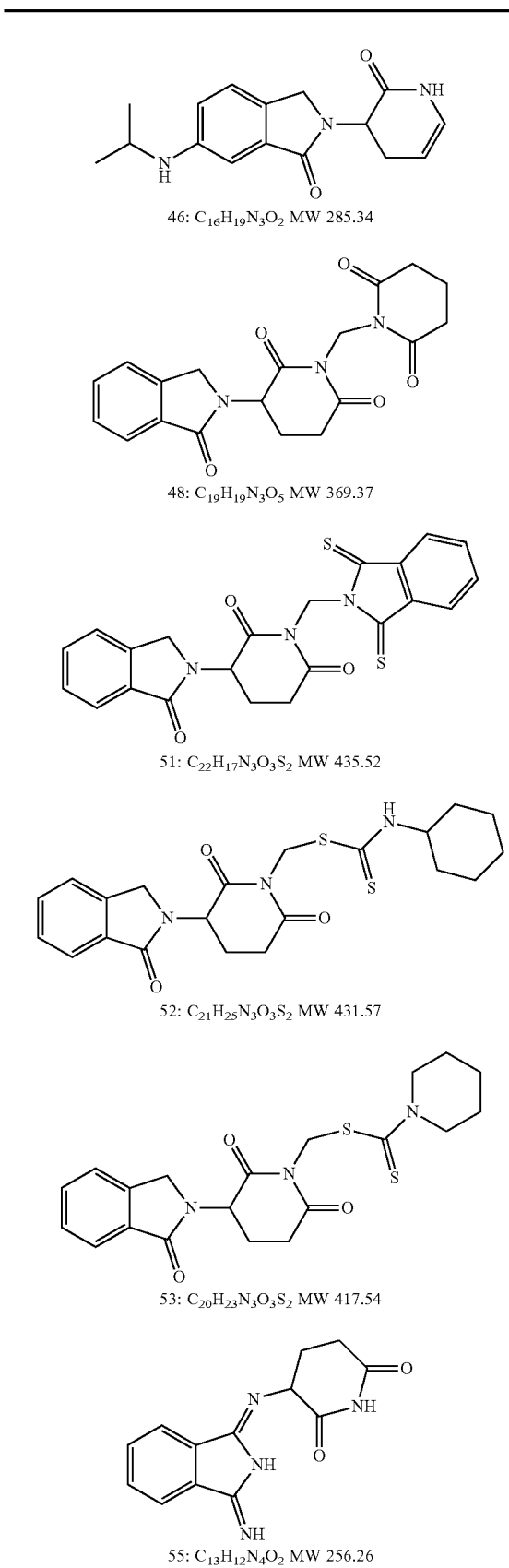
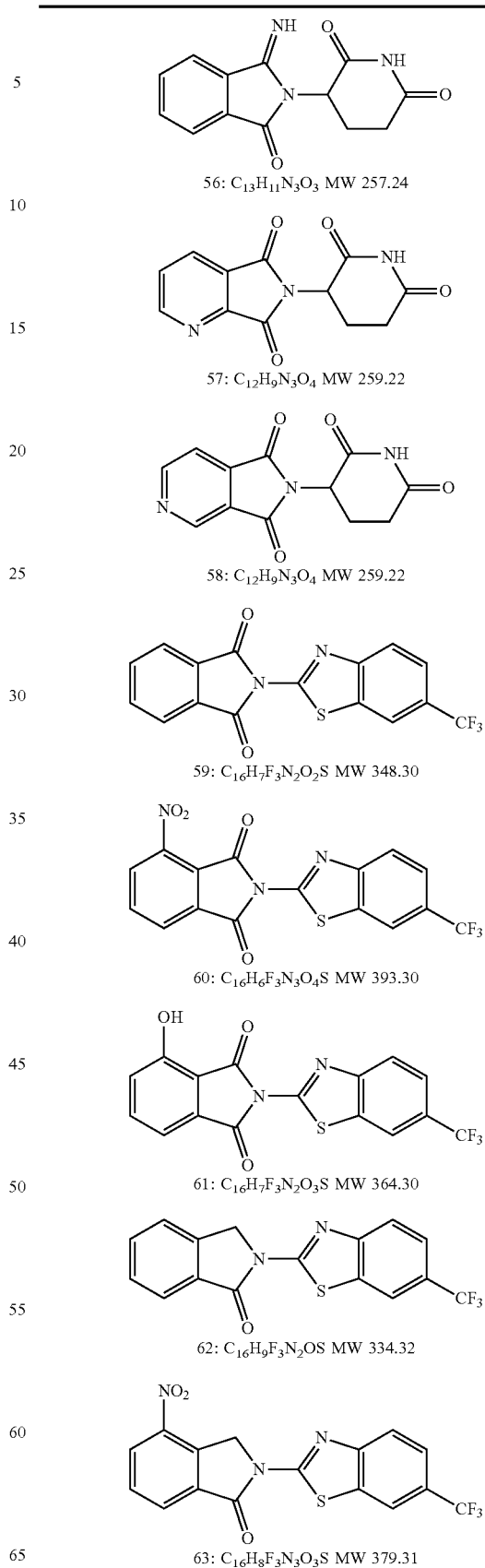

TABLE 5-continued

64: $C_{16}H_{14}N_2O_5S$ MW 346.36

65: $C_{16}H_{16}N_2O_4S$ MW 332.37

66: $C_{20}H_{12}F_6N_4$ MW 422.33

67: $C_{20}H_{12}F_6N_4$ MW 422.33

68: $C_{15}H_{10}F_3NO$ MW 277.24

69: $C_{18}H_{21}NO$ MW 267.37

70: $C_{19}H_{23}NO$ MW 281.39

TABLE 5-continued

71: $C_{20}H_{25}NO$ MW 295.42

72: $C_{18}H_{21}NO$ MW 267.37

73: $C_{17}H_{19}NO$ MW 253.34

74: $C_{20}H_{25}NS$ MW 311.48

76: $C_{18}H_{20}N_2O_3$ MW 312.36

77: $C_{18}H_{22}N_2O$ MW 282.38

81: $C_{20}H_{26}N_2O$ MW 310.43

82: $C_{18}H_{20}N_2O_3$ MW 312.36

TABLE 5-continued

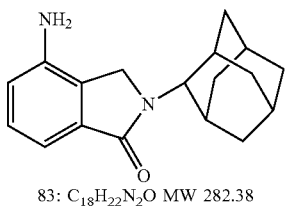

83: $C_{18}H_{22}N_2O$ MW 282.38

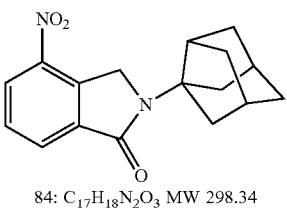

84: $C_{17}H_{18}N_2O_3$ MW 298.34

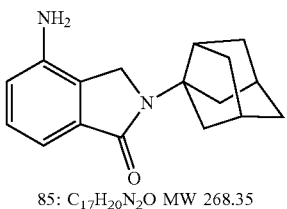

85: $C_{17}H_{20}N_2O$ MW 268.35

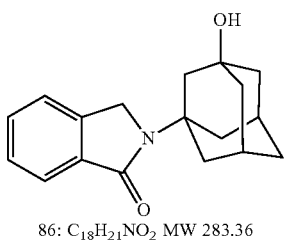

86: $C_{18}H_{21}NO_2$ MW 283.36

TABLE 5-continued

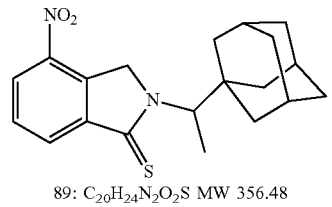

89: $C_{20}H_{24}N_2O_2S$ MW 356.48

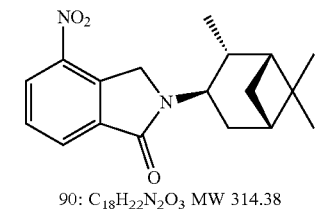

90: $C_{18}H_{22}N_2O_3$ MW 314.38

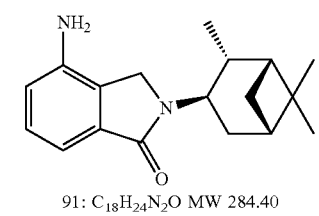

91: $C_{18}H_{24}N_2O$ MW 284.40

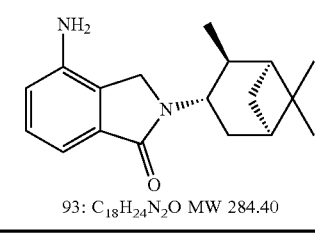

93: $C_{18}H_{24}N_2O$ MW 284.40

TABLE 6

The results shown are based on the lowest concentration of each compound producing an effect; compounds not producing an effect are shown at the highest evaluated concentration.

| | Assay | | | | | | | |
|---|---|---|---|---|---|---|---|---|
| | fli1:EGFP angiogenesis | | mpo:GFP inflammation | | WT Zebrafish | | Chicken | |
| Compound | (µg/mL) | n (survived/tested) | (µg/mL) | n (survived/tested) | (µg/mL) | n | (µg/mL) | n |
| 4 | 1.5 | 4/11 | 10 | 19/23 | 10 | 15 | 100 | 10 |
| 11 | 50 | 24/43 | 10 | 16/22 | 10 | 15 | 100 | 6 |
| 14 | 10 | 7/23 | 10 | 14/24 | 10 | 15 | 100 | 6 |
| 17 | 15 | 26/50 | 10 | 5/5 | 10 | 4 | 100 | 3 |
| 19 | 1 | 13/51 | 1 | 5/12 | 1 | 18 | 50 | 3 |
| 34 | 100 | 13/20 | 100 | 7/9 | 100 | 20 | 100 | 5 |
| 51 | 200 | 7/25 | 1 | 4/11 | | | 100 | 3 |
| 55 | 100 | 6/10 | 200 | 6/11 | | | 100 | 3 |
| 60 | 10 | 3/10 | 1 | 5/15 | | | 100 | 3 |
| 69 | 10 | 6/14 | 200 | 8/17 | | | 100 | 3 |
| 70 | 10 | 8/10 | 200 | 10/15 | | | 100 | 3 |
| 73 | 10 | 6/12 | 10 | 7/13 | | | 100 | 3 |
| 81 | 50 | 7/8 | 50 | 9/21 | 10 | 7 | 100 | 12 |
| 83 | 20 | 3/12 | 20 | 6/23 | 10 | 15 | 100 | 4 |
| 84 | 50 | 2/11 | 10 | 12/21 | 10 | 4 | 100 | 4 |
| 89 | 10 | 7/11 | | | | | 100 | 3 |
| 91 | 10 | 5/18 | | | | | 100 | 3 |
| 93 | 10 | 8/10 | | | | | 100 | 3 |
| 2 | 10 | 21/24 | 10 | 26/30 | 10 | 11 | 100 | 12 |
| 7 | 10 | 28/33 | 10 | 29/29 | 10 | 15 | 100 | 3 |
| 9 | 10 | 14/21 | 10 | 12/12 | 10 | 5 | 100 | 3 |

TABLE 6-continued

The results shown are based on the lowest concentration of each compound producing an effect; compounds not producing an effect are shown at the highest evaluated concentration.

| | Assay | | | | | | | |
|---|---|---|---|---|---|---|---|---|
| | fli1:EGFP angiogenesis | | mpo:GFP inflammation | | WT Zebrafish | | Chicken | |
| Compound | (μg/mL) | n (survived/tested) | (μg/mL) | n (survived/tested) | (μg/mL) | n | (μg/mL) | n |
| 46 | 10 | 14/30 | 10 | 24/50 | | | 100 | 3 |
| 53 | 10 | 9/14 | 10 | 13/19 | 100 | 7 | 100 | 3 |
| 56 | 10 | 9/19 | 10 | 7/8 | | | 50 | 8 |
| 58 | 10 | 33/33 | 5 | 7/16 | | | 100 | 3 |
| 59 | 10 | 21/32 | 100 | 6/11 | 100 | 5 | 50 | 6 |
| 64 | 10 | 8/15 | 10 | 8/15 | | | 100 | 3 |
| 65 | 200 | 13/13 | 200 | 10/20 | | | 100 | 3 |
| 72 | 200 | 9/20 | 10 | 6/15 | | | 100 | 3 |
| 74 | 10 | 9/15 | 200 | 6/14 | | | 100 | 3 |
| 77 | 10 | 43/62 | 200 | 5/21 | 100 | 39 | 100 | 3 |
| 86 | 200 | 4/12 | 100 | 14/19 | | | 100 | 3 |
| 5 | 7.5 | 8/14 | 10 | 28/28 | 15 | 15 | 100 | 3 |
| 24 | 50 | 13/25 | 50 | 6/6 | 50 | 5 | 100 | 3 |
| 29 | 10 | 6/17 | 5 | 2/10 | | | 50 | 11 |
| 32 | 100 | 21/25 | 10 | 6/15 | 50 | 15 | 100 | 3 |
| 33 | 100 | 15/21 | 10 | 4/15 | 50 | 15 | 100 | 5 |
| 67 | 10 | 13/22 | 200 | 6/15 | | | 100 | 3 |
| 76 | 10 | 28/32 | 100 | 5/11 | | | 100 | 3 |
| 18 | 50 | 24/43 | 50 | 14/14 | 50 | 15 | 100 | 6 |
| 20 | 10 | 51/79 | 10 | 8/14 | 10 | 18 | 50 | 6 |
| 23 | 10 | 23/30 | 10 | 13/35 | 10 | 15 | 100 | 3 |
| 30 | 10 | 4/8 | 10 | 10/10 | 10 | 27 | 100 | 3 |
| 52 | 100 | 6/7 | 100 | 7/21 | | | 100 | 3 |
| 57 | 8.5 | 8/12 | 17 | 8/15 | | | 100 | 3 |
| 61 | 100 | 3/15 | 1 | 9/20 | | | 100 | 3 |
| 62 | 10 | 18/20 | 10 | 6/20 | | | 100 | 3 |
| 63 | 200 | 6/23 | 100 | 12/20 | | | 50 | 3 |
| 66 | 100 | 15/15 | 100 | 6/15 | | | 100 | 3 |
| 68 | 10 | 22/34 | 100 | 5/15 | | | 50 | 4 |
| 82 | 5 | 18/27 | 5 | 8/22 | 5 | 8 | 100 | 8 |
| 85 | 10 | 7/20 | 100 | 11/20 | | | 100 | 3 |

Example 5

Cellular Proliferation, Nitrite, and TNF-α Protein Level Quantification

The CellTiter 96® AQueous One Solution Cell Proliferation Assay (Promega, Madison, Wis.) is routinely used as an assay of cell proliferation, and was used according to the manufacturer's recommendations. Changes in cellular health status are determined by use of indirect measures related to the formation of a colored tetrazolium dye product that can be measured spectrophotometrically at 490 nm λ. An elevation in absorbance is indicative of an increase in cell number and, hence, cellular proliferation. Optical densities (expressed as O.D.s) were measured after various incubations.

Nitrite levels in the culture media were measured by use of the Griess Reagent System (Promega, Madison, Wis.), following the manufacturer's protocol. The O.D. of unknown samples was read at 520 nm λ, compared to a sodium nitrite standard curve (1.5 μM to 100 μM) and nitrite measured media concentrations expressed as μM units. As the lowest nitrite concentration on the Griess Reagent System standard curve was 1.5 μM, this was chosen as the effective cutoff for defining measurable nitrite concentrations. TNF-α protein levels were measured by use of an ELISA specific for mouse TNF-α protein (BioLegend, San Diego, Calif.) and are expressed as a % change from their appropriate control or as pg/ml.

RAW 264.7 cells obtained from ATCC (Manassas, Va., USA) were grown in DMEM media supplemented with 10% FCS, penicillin 100 μg/ml and streptomycin 100 μg/ml, and maintained at 37° C. and 5% $CO_2$. Cells were seeded in 24 well plates and, 24 hours later, were utilized in studies. One hour prior to the initiation of any study, the seeding media was replaced with fresh media (1 mL), and the cells were allowed to equilibrate at 37° C. and 5% $C_O2$.

RAW 264.7 cells were challenged with LPS (Sigma, St Louis, Mo.: serotype 055:B5) from at a final concentration of 30 or 60 ng/mL. This concentration of LPS in RAW 264.7 cells induces a sub-maximal rise in both TNF-alpha and nitrite levels without a loss in cellular viability. This sub-maximal rise is useful for assessing whether the addition of an experimental drug can either lower or further raise levels of TNF-α and nitrite. Twenty four hours following the addition of LPS, conditioned media was harvested and analyzed for quantification of secreted TNF-α protein and nitrite levels. Fresh media was replaced into the wells and cell viability was then assessed.

Thalidomide and analogs were prepared in tissue culture grade DMSO (Sigma). RAW 264.7 cells were pretreated with thalidomide, analogues or vehicle one hour prior to a challenge with LPS. The effects of various concentrations of thalidomide analogues were assessed. All compounds were synthesized to a chemical purity of >99.5%, as assessed by chemical characterization by a combination of 1H NMR, 13C NMR and GC/MS analyses (Bruker AC-300 spectrometer, together with elemental analyses (Atlantic Microlab, Inc., Norcross, Ga.).

Data throughout are expressed as means±standard errors, where the n number is shown in parentheses. The n number refers to the number of wells in the tissue culture plates. Statistical comparisons were undertaken by use of either a Students t-test, or by One Way ANOVA with appropriate Bonferroni corrections for multiple comparisons, as required (GraphPad InStat Version 3.05). P values of <0.05 are considered to be of statistical significance, *, , * refer to P<0.05, P<0.01 and P<0.001 respectively. The results of representative compounds 7, 9, 59, 62, 64, 65, 68, 72, 74, 77, 81, 86, and 98 are shown graphically in FIGS. 8A and 8B. Additional results are shown in Tables 7-12; NS=not significant; a "+" sign=anti-inflammatory or increased cell numbers; a "−" sign=cell toxicity or pro-inflammatory.

TABLE 7

| Drug | 1 µM | | | 10 µM | | | 30 µM | | | 60 µM | | | 100 µM | | |
|---|---|---|---|---|---|---|---|---|---|---|---|---|---|---|---|
| # | TNF-α | Nitrite | Viability | TNF-α | Nitrite | Viability | TNF-α | Nitrite | Viability | TNF-α | Nitrite | Viability | TNF-α | Nitrite | Viability |
| 5 | NS | NS | NS | NS | NS | NS | NS | NS | NS | NS | NS | NS | NS | NS | NS |
| 6 | NS | NS | NS | NS | NS | NS | NS | − | NS | NS | NS | NS | NS | − | + |
| 7 | NS | NS | NS | NS | NS | NS | NS | + | NS | NS | + | NS | + | + | + |
| 8 | | | | | | | NS | NS | NS | NS | NS | NS | NS | NS | NS |
| 9 | | | | | | | NS | + | NS | NS | + | NS | NS | + | + |

TABLE 8

| | 3 µM | | 10 µM | | 30 µM | |
|---|---|---|---|---|---|---|
| Drug # | TNF-α | Viability | TNF-α | Viability | TNF-α | Viability |
| 28 | NS | − | NS | − | + | − |
| 29 | NS | − | NS | − | NS | − |
| 31 | NS | NS | + | NS | + | NS |
| 32 | + | NS | + | NS | + | NS |
| 35 | NS | NS | NS | NS | NS | NS |
| 36 | NS | NS | NS | NS | + | NS |
| 37 | NS | NS | NS | NS | + | NS |
| 38 | NS | NS | NS | NS | NS | NS |
| 39 | NS | NS | NS | NS | NS | NS |
| 40 | NS | NS | NS | NS | + | NS |
| 41 | + | NS | + | NS | + | NS |
| 43 | NS | NS | NS | NS | NS | NS |
| 44 | NS | NS | NS | NS | + | NS |
| 54 | NS | NS | + | NS | + | − |
| 106 | NS | + | NS | + | NS | + |

TABLE 9

| | 1 µM | | 10 µM | | 30 µM | |
|---|---|---|---|---|---|---|
| Drug # | TNF-α | Viability | TNF-α | Viability | TNF-α | Viability |
| 47 | + | NS | + | NS | + | NS |
| 48 | + | NS | + | NS | + | NS |
| 49 | + | NS | NS | NS | + | NS |
| 50 | NS | − | + | NS | NS | NS |
| 51 | + | NS | + | NS | + | − |
| 52 | + | NS | + | NS | + | NS |
| 53 | + | − | + | NS | NS | + |

TABLE 10

| | 1 µM | | | 10 µM | | | 30 µM | | |
|---|---|---|---|---|---|---|---|---|---|
| Drug # | TNF-α | Nitrite | Viability | TNF-α | Nitrite | Viability | TNF-α | Nitrite | Viability |
| 57 | NS | NS | NS | NS | + | NS | NS | + | NS |
| 58 | NS | + | NS | NS | + | NS | NS | + | NS |
| 59 | NS | + | NS | NS | NS | NS | + | + | NS |

TABLE 10-continued

|        | 1 µM  |         |           | 10 µM |         |           | 30 µM |         |           |
|--------|-------|---------|-----------|-------|---------|-----------|-------|---------|-----------|
| Drug # | TNF-α | Nitrite | Viability | TNF-α | Nitrite | Viability | TNF-α | Nitrite | Viability |
| 61 | NS | NS | NS | NS | + | NS | + | + | − |
| 62 | NS | NS | NS | NS | NS | NS | NS | + | NS |
| 63 | NS | − | NS | NS | − | NS | NS | − | − |
| 64 | NS | NS | NS | NS | NS | NS | NS | NS | NS |
| 65 | − | NS | NS | − | NS | NS | − | NS | NS |
| 66 | NS | NS | − | NS | NS | NS | + | + | − |
| 67 | NS | NS | NS | NS | NS | NS | NS | + | NS |
| 68 | NS | NS | NS | NS | NS | NS | NS | NS | NS |
| 69 | NS | NS | NS | NS | NS | NS | NS | NS | NS |
| 70 | NS | NS | NS | + | NS | NS | + | + | NS |
| 71 | NS | NS | NS | NS | NS | NS | + | + | − |
| 72 | + | NS | + | NS | NS | NS | + | + | − |
| 73 | NS | NS | NS | NS | + | NS | + | + | − |
| 74 | NS | NS | NS | NS | NS | NS | NS | + | NS |
| 75 | NS | NS | NS | + | NS | NS | + | NS | NS |
| 76 | NS | NS | NS | NS | + | NS | + | + | NS |
| 77 | NS | NS | NS | NS | NS | NS | NS | NS | NS |
| 78 | NS | NS | NS | + | NS | NS | + | + | − |
| 79 | NS | NS | NS | NS | NS | NS | NS | + | − |
| 80 | NS | NS | NS | + | + | − | + | + | NS |
| 81 | NS | NS | NS | NS | NS | NS | + | + | NS |
| 82 | NS | + | NS | + | + | − | + | + | − |
| 83 | NS | NS | NS | NS | + | NS | NS | + | NS |
| 84 | NS | NS | NS | NS | + | NS | NS | + | NS |
| 85 | NS | NS | NS | NS | NS | NS | NS | − | NS |
| 86 | NS | NS | NS | + | NS | NS | + | NS | NS |
| 87 | NS | NS | NS | NS | NS | NS | NS | NS | NS |
| 88 | NS | NS | NS | NS | NS | NS | NS | NS | NS |
| 89 | NS | NS | NS | NS | + | NS | NS | + | − |

TABLE 11

|        | 1 µM  |         |           | 10 µM |         |           | 30 µM |         |           |
|--------|-------|---------|-----------|-------|---------|-----------|-------|---------|-----------|
| Drug # | TNF-α | Nitrite | Viability | TNF-α | Nitrite | Viability | TNF-α | Nitrite | Viability |
| 90  | +   | + | NS | + | + | NS | + | + | NS |
| 91  | NS  | + | NS | + | + | + | + | + | + |
| 92  | NS  | + | NS | + | + | − | + | + | − |
| 93  | NS  | NS | NS | NS | NS | NS | NS | + | NS |
| 94  | NS  | + | NS | + | + | — | + | + | − |
| 95  | NS  | NS | NS | NS | NS | + | NS | + | + |
| 96  | NS  | + | − | + | + | − | + | + | NS |
| 97  | NS  | NS | NS | + | NS | NS | NS | + | NS |
| 98  | SIG | + | NS | + | + | NS | + | + | NS |
| 99  | NS  | + | NS | NS | + | − | + | + | − |
| 100 | NS  | NS | NS | NS | NS | NS | NS | NS | NS |
| 101 | NS  | + | − | NS | + | − | + | + | NS |
| 102 | NS  | NS | NS | NS | NS | NS | NS | NS | NS |
| 103 | NS  | + | NS | + | + | NS | SIG | NS | SIG |
| 104 | NS  | − | NS | NS | − | NS | NS | − | NS |
| 105 | NS  | NS | NS | NS | + | NS | + | + | − |

TABLE 12

|        | 10 µM |         |           | 30 µM |         |           | 60 µM |         |           |
|--------|-------|---------|-----------|-------|---------|-----------|-------|---------|-----------|
| Drug # | TNF-α | Nitrite | Viability | TNF-α | Nitrite | Viability | TNF-α | Nitrite | Viability |
| 111 | NS | NS | NS | NS | NS | NS | NS | − | NS |
| 112 | NS | NS | − | + | + | − | + | + | − |
| 113 | NS | NS | NS | + | + | − | + | + | − |
| 114 | + | + | − | + | + | − | + | + | − |
| 115 | + | + | − | + | + | − | + | + | − |
| 116 | NS | NS | − | NS | NS | − | NS | NS | NS |
| 117 | + | + | − | + | + | − | + | + | − |
| 118 | + | + | − | + | + | − | + | + | − |

TABLE 12-continued

| | 10 µM | | | 30 µM | | | 60 µM | | |
|---|---|---|---|---|---|---|---|---|---|
| Drug # | TNF-α | Nitrite | Viability | TNF-α | Nitrite | Viability | TNF-α | Nitrite | Viability |
| 119 | + | + | − | + | + | − | + | + | − |
| 120 | + | + | − | + | + | − | + | + | − |
| *121 | | | | NS | + | NS | + | + | NS |

*Drug 121 at 100 µM: TNF-α = +, Nitrite = +, Viability = NS

Example 6

Rat Aortic Ring Assay of Angiogenesis

Matrigel® matrix (BD Biosciences) was defrosted overnight on ice. The wells of a 24 well plate were coated with 300 µL of the gel using frozen pipette tips. The gel was left to set at room temperature. When required, six week old male Sprague Dawley rats were euthanized by $CO_2$ and decapitation. The blood was drained from the tissue and the descending aorta dissected. The aorta was cleaned in EBM media, the over lying fascia removed, and the tissue was sliced into 1-mm sections using a sterile scalpel and tweezers. The sections were rinsed in clean EBM then placed onto the coagulated gel. Another 300 µL of Matrigel® matrix was pipetted onto the ring and left to set for 30 minutes. EGM™-II endothelial growth medium (500 µL) was added to each well. The rings were incubated overnight at 37° C. The next day the media was removed and replaced with EBM containing compounds (50 µM) or media. TNP-470 ((Chloracetyl) carbamic acid (3R,4S,5S,6R)-5-methoxy-4-[(2R,3R)-2-methyl-3-(3-methyl-2-butenyl)oxiranyl]-1-oxaspiro[2.5]oct-6-yl ester) was used as a positive control. The rings were incubated in the compounds for 5 days. On day 5 the rings were imaged using an EVOS™ scope. The vessel outgrowth was quantified by binary conversion in Image J open-source image processing software and average outgrowth calculated (FIG. 9). Compound 86 reduced outgrowth the most in this assay (17.3% outgrowth).

Example 7

HUVEC Lattice Formation

ECMatrix™ gel solution and 10× diluent buffer (Millipore) were defrosted slowly overnight on ice. One part diluent was added to nine parts gel using frozen pipette tips. 100 µL of the ECMatrix™ solution was slowly added to the required wells in a 96 well plate and left to set for one hour. HUVEC cells (human umbilical vein endothelial cells) were harvested and counted. The cells were resuspended and plated at 100000 cells/well in 100 µL of RPMI medium with thalidomide analogs (1-30 uM) or DMSO. The plates were returned to the incubator and analysed after 18 hours of exposure. The extent of inhibition of lattice formation was assessed using ImageJ. Results are shown for 1 µM, 10 µM, and 30 µM concentrations of the thalidomide analogs (FIGS. 10A and 10B).

Example 8

Anti-Cancer Screening

As well as being immunomodulatory and anti-angiogenic, lenalidomide and pomalidomide are directly cytotoxic to cancer cells. To establish if the lead compounds exhibited similar abilities, Compounds 29 and 86 underwent screening in 59 cancer cell lines. Compounds 29 and 86 were screened at a concentration of $1\times10^{-5}$ M (FIGS. 11 and 12, respectively). Calculated values from 0-100 indicate growth inhibition relative to a no-drug control, and values less than 0 indicate lethality, relative to the number of cells at time zero. A value of 100 means no growth inhibition. A value of 40 means 60% growth inhibition. A value of 0 means no net growth over the course of the experiment. A value of −40 means 40% lethality. A value of −100 means all cells are dead. With the exception of leukemic cell lines, both compounds exhibited very little activity in this assay. The lack of anti-cancer activity for compounds 29 (FIG. 11) and 86 (FIG. 12) suggests they are targeting the vasculature directly, and are not simply cytotoxic to the cells.

Example 9

Anti-Angiogenic Activity in an Ex Vivo Model

The saphenous vein was cleaned of subcutaneous tissue and embedded in Matrigel® matrix as previously described. After 10 days of incubation, the transverse sections of the veins were imaged. The outgrowth between the vehicle and no treatment (media) control was equivalent (106.65%±20.14, n=2 and 103.35%±4.06, n=2 respectively; FIGS. 13A and 13B). Treatment with TNP-470 caused a vast reduction in vessel outgrowth (9.44%±1.65, n=3; FIGS. 13A and 13C (vein section plated on its side). When the thalidomide analogs 29 and 86 were tested, there was a clear distinction in the activities of the compounds. Compound 86 was able to inhibit outgrowth at all concentrations (FIGS. 13A and 13E (10 µM); n=3 per concentration). At 5 µM (155.12%±23.69, n=3) 10 µM (168.06%±14.87, n=2) and 50 µM (102.38%±16.78, n=3), there was no significant decrease in vessel outgrowth by compound 29 (FIGS. 13A and 13D (10 µM)). At high concentrations (100 µM) compound 29 had a limited anti-angiogenic effect (62.53%±13.69, n=3; FIG. 13A).

Example 10

Maximum Tolerated Dose and In Vivo Efficacy

Compounds 29 and 86 were selected for in vivo efficacy studies of human prostate cancer. Mice positive for the severe combined immune deficieny (SCID) spontaneous mutation $Prkdc^{scid}$ are deficient in functional T cells and B cells, have reduced levels of gamma globulins and lymphopenia (low white blood cell count). Due to their comprised immune system, SCID mice are amenable to xenogeneic grafts. Before starting the efficacy study, a maximum tolerated dose was established for each compound. Compound administration was by tail vein injection (IV) with a 27-gauge needle. A volume of 100 uL per 25 g of body weight was injected for each compound and dose. Compounds 29 and 86 were formulated in 12% DMSO and 88% TPGS (tocopherol polyethylene glycol succinate) in distilled sterile water. This formulation was well tolerated in vehicle control mice. The maximum tolerated dose was defined as the highest dose at which 100% of animals could tolerate treatment with mild or no toxicity for a minimum of one week of treatment. Initially, each compound was administered 3× per week to five mice per group, at 5 and 10 mg/kg. Each dose level was monitored for at least one week. At 20 mg/kg, the compounds were seen to precipitate in the solution. Animals were weighed daily during the treatment courses. At 5 mg/kg and 10 mg/kg, no animals died or needed to be euthanized due to drug-related toxicity and no significant weight loss was observed for any treatment group (FIG. 14). The selected dose for further experimentation was therefore 10 mg/kg.

When the tumors of SCID mice xenografted with PC3 cells were palpable, mice were dosed with 10 mg/kg of compound 29 or compound 86, or given the vehicle alone. From day 0 to day 24, the tumor sizes in vehicle-treated animals increased by 301.33% (FIG. 15, tumor size=401.33%±35.98%). No reduction in tumor burden was observed for either treatment group. However, there was a trend to separate between the vehicle treated and compound 86 treated mice (p=0.07), suggesting an inhibition of tumor growth rather than reduction of tumor burden.

Example 10

Models for Screening and/or Evaluation of Thalidomide Analogs for Treatment of Alzheimer's Disease, Traumatic Brain Injury, Ischemic Stroke, Multiple Sclerosis, and Systemic Inflammatory Disorders Evaluation of potential actions in Alzheimer's disease (AD) can be appraised in transgenic mouse models of AD that include APP+PS1 gene mutations that result in the excessive production of the AD toxic peptide amyloid-β (Aβ), as described within Tweedie et al. (*J Neuroinflamm* 9:106, 2012; Gabbita *J Neuroinflamm*. 9:99, 2012). For such mice in a time-dependent manner, Aβ is generated and aggregates in brain as amyloid plaques that can be appropriately quantified biochemically and/or stained for visualization by immunohistochemical techniques (see Tweedie et al., *J Neuroinflamm* 9:106, 2012). Elevations in phosphorylated-tau and reductions in synaptic markers (for example, SNAP25 and synaptophysin) are additionally evident, as are elevations in markers of neuroinflammation (for example, CD68-positive microglia) that associate with impairments in measures of cognitive performance (as for example measured by the Morris water maze). The daily administration over multiple weeks (for example, 6 weeks) of a well-tolerated compound that lowers TNF-α can result in mitigation of many of these aberrant changes, as compared to untreated mice and/or younger mice of the same background.

Evaluation of actions of anti-inflammatory agents and in particular those that lower TNF-α generation can be valuably appraised across a number of animal models of mild and moderate traumatic brain injury (TBI), which represent the majority of cases that present in humans. The weight drop model, one of the original animal models of TBI, involves dropping a free-falling weight guided by metal tubing to impact the temporal brain region of an anesthetized animal (for mice such a weight is often 30 or 50 g from approximately 80 cm (31.5 inches) height, which represents concussing an animal with approximately its own weight in much the same manner as the banging of heads in human contact sports or a fall in the elderly. Anesthesia for this weight drop model is best achieved by use of a short-acting gaseous anesthetic (for example, isoflurane) delivered immediately before the injury, contributing to this method's ease of preparation. This range of weight generates an injury that is free from gross neuroanatomical changes (Tweedie et al., *J Neurosci Res.* 85:805-15, 2007) and skull fracture complications that can occur with heavier weights. For this model, the anesthetized mouse is placed below the guide tube through which the weight is dropped, aligned so that it will strike the skull on the temporal side, between the corner of the eye and the ear (predefined on either the left or right side). The head rests on a supportive foam sponge positioned to allow antero-posterior motion without any rotational head movement at the moment of impact (Rachmany et al., *PLoS ONE*, 8:e79837, 2013; Baratz et al., *J Neuroinflamm* 12:45, 2015). The resulting pathology of the weight drop technique is neurodegeneration with diffuse neuronal cell death and neuroinflammation throughout cortical areas and hippocampus of the impacted side of the brain. This can be evaluated by biochemical assays of TNF-α or other proinflammatory cytokines, and by immunohistochemical analysis of markers of degeneration elevated. FluoroJade B or C staining) with and without neuronal marker (e.g., NeuN) quantification, and by quantification of astrocyte/microglia activation (e.g., elevated glial fibrillary acidic protein and/or Ibal antibody staining). Chief symptoms of mild TBI in humans as well as the weight drop rodent model of the disorder include cognitive impairments, particularly in measures of spatial and visual memory that can be quantified in rodents with behavioral tests (specifically by employing novel object recognition and Y-maze paradigms, respectively (Deselms et al., *J Neurosci Methods* 2016). The administration of an effective amount of a TNF-α lowering drug, optionally in conjunction with an anti-inflammatory drug, can mitigate behavioral impairments measured as early as within 7 days or after longer durations (i.e., 30 days) and can mitigate elevations in proinflammatory cytokine levels, neuronal apopotosis and markers of neuroinflammation, as utilizing paradigms used within Baratz et al., (*J Neuroinflamm* 12:45, 2015). In rodents, the experimental drug is administered by any suitable route, e.g., systemically, as a single dose or multiple doses within 12 hr of induction of brain injury. The timeframe for administering the experimental drug may be different in species other than rodents; for example, the timeframe may be substantially longer for administration to humans.

For moderate TBI, rodent models including controlled cortical impact (CCI) and fluid percussion injury (FPI) models can be used to evaluate efficacy of anti-inflammatory/TNF-α lowering agents, as detailed within Wang et al., (*J Neuroinflamm* 13(1):168, 2016) and Eakin et al., (PLoS One. 8(12):e82016, 2013). In these well-characterized animal models of brain injury, a mechanical injury force is directly applied to the surface of the brain, and thus a craniectomy is required before injury induction in either the anesthetized mouse or rat (Deselms et al., *J Neurosci Method* 2016). For CCI this is delivered by a rigid impactor using an instrument that is precisely adjustable over the parameters of time, velocity and depth (Wang et al., *J Neuroinflamm* 13(1):168, 2016), whereas for FPI a fluid-mediated pressure pulse is generated by a classical piece of equipment. This comprises a cylindrical reservoir that is filled with sterile isotonic saline, which on one end has a transducer connected via a tube and male Luer lock to a female Luer lock attached to the skull. Injury is initiated by the development of an acute fluid pulse against the intact dural surface, which is induced by the release of a pendulum (from a precalibrated height or angle associated with a desired injury severity) that strikes a piston at the other end of the reservoir (Eakin et al., (PLoS One. 8(12):e82016, 2013; Deselms et al., *J Neurosci Method* 2016). Both models can induce graded levels of brain injury and create axonal injuries and contusions, accompanied by impaired neurologic motor function and cognitive impairments. This is accompanied by immediate necrotic cell death and, more importantly, by a slower apoptotic cell death that is amenable to reversal within cortical and hippocampal regions (Yang et al., *Exp Neurol.* 269:56-66, 2015; Yang et al., *Neurobiol Dis* 2016). Appraisal of efficacious anti-inflammatory/TNF-α lowering agents is evaluated by their administration (e.g., systemically, whether by intravenous or another route) at a time up to 5 to 7 hr following injury in rodents. The timeframe may vary in other species; for example, the treatment window may be longer in humans. Evaluation of brain inflammation and neuronal loss is made by biochemical and immunohistochemical assays, as detailed in Wang et al., (*Neuroinflamm* 13(1):168, 2016), and behavioral measures include functional outcomes as revealed by (i) motor asymmetry measured by elevated body swing test, (ii) motor coordination and balance assessed by a beam walking test, (iii) a neurological severity scores (mNSS) to provide a composite evaluation of overall neurologic function, and (iv) analysis of sensory/motor function by quantifying the latency for animals to remove an adhesive sticker from their fore paw—contralateral to the side of brain injury (as detailed in Yang et al., *Exp Neurol.* 269:56-66, 2015; Yang et al., *Neurobiol Dis* 2016). Cognitive assessment likewise can be made that show impairments, as evaluated by Morris Water Maze (as detailed in Eakin et al., *PLoS One.* 8(12):e82016, 2013), which is amenable to rescue by an effective therapy.

A further model to evaluate efficacy and functional outcome of anti-inflammatory/TNF-α lowering agents following brain damage can be undertaken in the classical rodent model of focal ischemic stroke induced by middle cerebral artery occlusion/reperfusion (MCAO/R) performed via the intraluminal suture technique in an anesthetized mouse or rat with 1 hr of MCAO, as described by Yoon et al., (*J Neurosci Res.* 91(5):671-80, 2013). In this animal model of ischemic stroke, experimental therapeutics are evaluated after administration by any suitable route, such as by systemically, at times either prior to or following MCAO/R (for example up to 3 hr after injury). Immunohistochemical and biochemical analyses then undertaken at 24 to 72 hr to evaluate markers in neuroinflammation (for example, GFAP and Iba1 staining, and/or evaluation of TNF-α brain levels), area/volume of infarction (2,3,5-triphenyltetrazolium chloride (TTC) staining). Additionally, behavioral studies can reveal efficacious drug effects (for example by evaluation of a 5-point neurological deficit score (0, no deficit; 1, failure to extend left paw; 2, circling to the left; 3, falling to the left; 4, unable to the walk spontaneously) assessed in a blinded manner).

In a further example, efficacy of compounds can be evaluated in an animal model of multiple sclerosis involving experimental autoimmune encephalomyelitis (EAE), as described in Eitan et al, (Exp Neurol. 273:151-60, 2015). EAE is induced with MOG 35-55 peptide (Hooke Laboratories, Inc.; kit EK-2110), whereby on day 0, mice receive two subcutaneous injections of MOG 35-55 mixed with an adjuvant and 2 h later pertussis toxin is injected intraperitoneally. One day later (i.e., experimental day 1) a second pertussis toxin injection is administered, and then mice are evaluated daily over an extended time (for example, 23 days) with the provision of readily available soft food and water in the cages when severe motor impairment occurs. In addition to following weight, behavioral scoring can be time-dependently undertaken to evaluate efficacious experimental drug treatment effects, and classical biochemistry and immunohistochemistry can be undertaken (to measure, for example, cytokine levels, markers of neuroinflammation (GFAP, Iba1), myelination (as for example by myelin basic protein antibody levels). As an example of a behavioral assessment of value to define efficacious drug actions, a widely-employed six-point scale can be used as follows: 0) no evidence of motor impairment, tail is erect, and mouse spreads hind legs when picked up by the tail; 1) tail is limp when the mouse is picked up by the base of the tail; 2) limp tail, weakness in hind legs/wobbly gait, and legs closed when picked up by the tail; 3) limp tail with paralysis of one front and one hind limb; 4) limp tail, complete hind limb paralysis, and partial forelimb paralysis; and 5) mouse is found dead or must be euthanized due to severe paralysis. Additionally, motor evaluations can be made by use of a rotor rod, as detailed in Eitan et al., (Exp Neurol. 273:151-60, 2015).

Systemic disorders that have an inflammatory involvement additionally can be evaluated for efficacious drug actions, as for example in animal models of sarcopenia involving hind limb suspension to induce muscle wasting. To achieve muscle unloading by hindlimb suspension, mice can be anesthetized (i.e., 2.5% isoflurane) and their tails cleaned with rubbing alcohol and air dried, covered with a light coat of benzoin tincture, and dried with a hair dryer until tacky. Strips of elastoplast adhesive bandage can then be applied to the proximal two-thirds of all sides of the tail and looped through a swivel attachment mounted above the cage designed to allow the animal to move rotationally 360° with only the forelimbs able to come into contact with the cage floor. The animals are provided food and water ad libitum and monitored daily for signs of lethargy or illness. Evaluation of efficacy of experimental drugs is made following their administration daily, e.g., systemic administration, over an extended period of time with efficacy measures related to leg skeletal muscle weight, as well as biochemical, immunohistochemical and functional measures. As little as 5 days of muscle unloading can induce atrophy (Fix et al., *J Appl Physiol* 2016). Biochemical and immuno-histochemical analyses can be made of muscle structure (including Western blot analysis of key muscle proteins), as well as quantification of capillary networks and mitochondria number and function. In addition, functional evaluations (such as defined measures of gait) can be quantified. These evaluations can be made during muscle unloading and, in particular, during reloading of muscle to evaluate the normalization of muscle structure following its wasting. Notably, TNF-α is chronically elevated in sarcopenia, and its higher levels are strongly correlated with muscle loss, reduced strength and morbidity (Schaap et al., *J Gerontol-Series A Biol Sci & Med Sci* 64: 1183-9, 2009; Fan et al., *Mediators Inflamm.* 2016: 1438686, 2016). TNF-α induces skeletal muscle loss through increased myofibrillar protein degradation and cell apoptosis, and thus induces muscle atrophy and the inhibition of muscle regeneration following injury (Zhao et al., *Biochem Biophys Res Comm* 458:790-5, 2015). In vivo, myosin heavy chain protein synthesis rate correlates negatively with TNF-α expression in skeletal muscle, and TNF-α injection into mice induces ubiquitin-proteasome system activation and a decrease of skeletal muscle function (Sakuma K, et al., *Pflugers Arch* 467: 213-29, 2015) supporting the mechanism via which an effective and well-tolerated anti-inflammatory/TNF-α lowering agent could provide efficacy in sarcopenia and associated disorders involving progressive muscle loss.

Example 11

Treatment with Thalidomide Analogs

A subject having a condition that may be ameliorated with an embodiment of the disclosed analogs is identified and selected for treatment. The subject may have, for example, a disorder mediated by TNF-α activity, TNF-α protein levels, inflammation, and/or angiogenesis. The subject may be selected based on a clinical presentation and/or by performing tests to demonstrate presence of the disorder.

The subject is treated by administering a thalidomide analog, a pharmaceutically acceptable salt thereof, or a pharmaceutical composition thereof at an amount determined by a clinician to be therapeutically effective. The compound is administered by any suitable means including, but not limited to, orally, parenterally, rectally, nasally, buccally, vaginally, topically, optically, by inhalation spray, or via an implanted reservoir. In some embodiments, the administered thalidomide analog possesses anti-inflammatory properties. When treating a disorder that is not mediated by angiogenesis, the thalidomide analog may not possess anti-angiogenic properties. In certain embodiments, the administered thalidomide analog is non-teratogenic. Advantageously, the thalidomide analog also may be non-neurotoxic at the administered dose.

A therapeutically effective amount of a second agent may be co-administered with the compound. The compound and the second agent may be administered either separately or together in a single composition. The second agent may be administered by the same route or a different route. If administered concurrently, the compound and the second agent may be combined in a single pharmaceutical composition or may be administered concurrently as two pharmaceutical compositions. The second agent may be, for example, an angiogenesis inhibitor, an anti-cancer agent, or an anti-inflammatory agent.

Several representative embodiments are described in the numbered paragraphs below.

1. A thalidomide analog or pharmaceutically acceptable salt thereof, wherein the thalidomide analog is a compound according to general formula I or

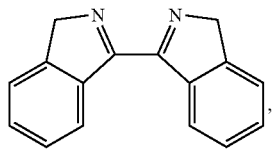

wherein general formula I is

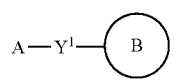

(I)

where $Y^1$ is a bond, —CH$_2$—, or —CH(CH$_3$)—; A is —NH$_3$X where X is an anion with a −1 charge, or A is general formula II

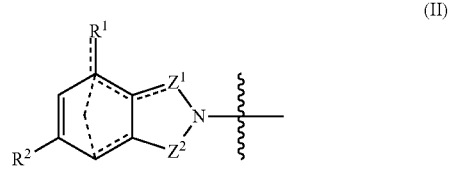

(II)

where bonds represented by "----" are optional bonds, and each bond represented by "=====" is a single or double bond as needed to satisfy valence requirements; $R^1$ is —H, —NO$_2$, —NH$_2$, —OC(O)CH$_3$, or —NO$_2$H; $R^2$ is —H, —NH$_2$, or —N(H)CH(CH$_3$)$_2$; $Z^1$ is CH$_2$, C=O, or CH; and $Z^2$ is CH$_2$, C=O, C=S,

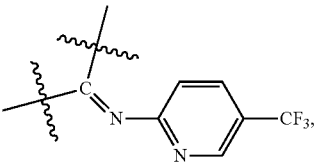 [SMILES: *C(*)=Nc1ccc(C(F)(F)F)cn1]

or

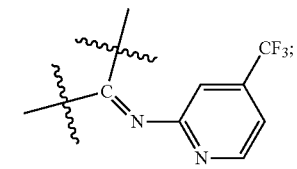 [SMILES: *C(*)=Nc1cc(C(F)(F)F)ccn1]

Ring B is:

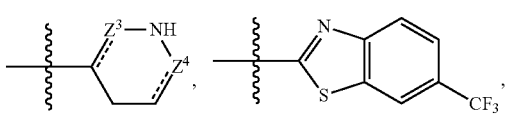

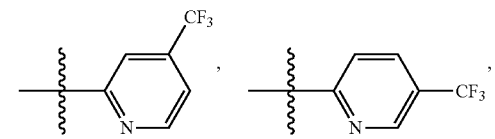

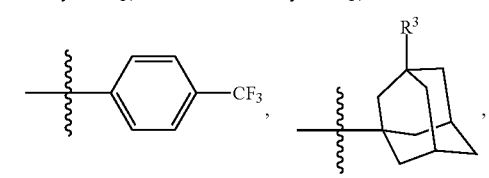

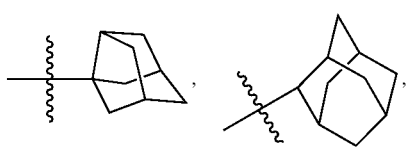

-continued

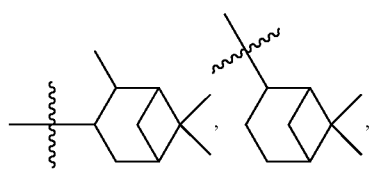

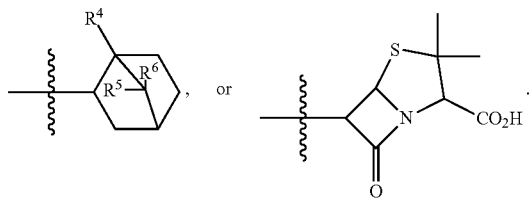

where each bond represented by "-----" is a single or double bond as needed to satisfy valence requirements; $Z^3$ is C=O, C=S, or CH; $Z^4$ is C=O, C=S, or CH, and at least one of $Z^3$ and $Z^4$ is C=O or C=S; $R^3$ is —H or —OH; $R^4$ is —H or —CH$_3$; and $R^5$ and $R^6$ are both —H or both —CH$_3$; wherein:

if ring B is

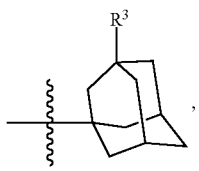

$R^1$ is —H, —NH$_2$ or —NO$_2$, $R^2$ and $R^3$ are —H, $Z^1$ is CH$_2$, and $Z^2$ is C=O, then $Y^1$ is not a bond;

if ring B is

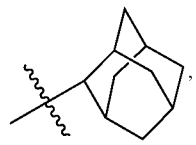 [SMILES: *C1C2CC3CC(C2)CC1C3]

$R^1$ and $R^2$ are H, $Z^1$ is CH$_2$ and $Z^2$ is C=O, then $Y^1$ is not a bond;

if ring B is

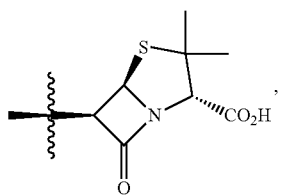 [SMILES: *[C@@H]1C(=O)N2[C@@H]1SC(C)(C)[C@@H]2C(=O)O]

and $R^1$ and $R^2$ are H, then one of $Z^1$ and $Z^2$ is other than C=O; and if ring B is

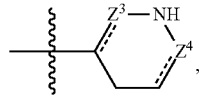

then (i) $R^1$ is not —NH$_2$; (ii) if $R^1$ is —NO$_2$ and $Y^1$ is a bond, then at least one of $Z^1$ and $Z^2$ is C=O and one of $Z^3$ and $Z^4$ is other than C=O or C=S, or if both $Z^1$ and $Z^2$ are C=O, then $Z^3$ is C=O or C=S and $Z^4$ is C=S; (iii) if $R^2$ is —NH$_2$ and $Y^1$ is a bond, then one of $Z^1$ and $Z^2$ is other than C=O, and one of $Z^3$ and $Z^4$ is other than C=O or C=S; (iv) if $R^2$ is —NO$_2$ and $Y^1$ is a bond, then one of $Z^3$ and $Z^4$ is other than C=O or C=S; (v) if $R^2$ is N(H)CH(CH$_3$)$_2$, $Y^1$ is a bond, $Z^1$ is CH$_2$ and $Z^2$ is C=O, then one of $Z^3$ and $Z^4$ is other than C=O; and (vi) if A is —NH$_3$X, X is CF$_3$CO$_2^-$, and $Y^1$ is a bond, then at least one of $Z^3$ and $Z^4$ is other than C=O.

2. A method for inhibiting TNF-α activity, angiogenesis, inflammation, or a combination thereof, comprising contacting a cell with an effective amount of a thalidomide analog according to paragraph 1, compound 64, compound 72, or compound 77, or a pharmaceutically acceptable salt thereof.

3. The method according to paragraph 2, wherein the thalidomide analog is non-teratogenic.

4. The method according to paragraph 2 or paragraph 3 wherein the thalidomide analog is compound 7, 9, 46, 59, 64, 65, 72, 74, 77, or 86.

5. The method according to paragraph 4, wherein the thalidomide analog is compound 7, 9, 46, 59, 65, 74, or 86.

6. The method according to any one of paragraphs 2-5, wherein contacting the cell with an effective amount of the thalidomide analog comprises administering to a subject a therapeutically effective amount of the thalidomide analog or pharmaceutically acceptable salt thereof or a therapeutically effective amount of a pharmaceutical composition comprising the thalidomide analog or pharmaceutically acceptable salt thereof.

7. The method according to paragraph 6, further comprising administering to the subject a second therapeutic agent.

8. The method according to paragraph 7, wherein the second therapeutic agent is an anti-cancer agent, an anti-angiogenic agent, or an anti-inflammatory agent.

9. A method for inhibiting inflammation in a subject, comprising administering to the subject a therapeutically effective amount of a thalidomide analog according to paragraph 1, wherein the thalidomide analog is non-teratogenic and possesses anti-inflammatory properties.

10. The method according to paragraph 9, wherein the thalidomide analog is compound 7, 9, 46, 59, 64, 65, 72, 74, 77, or 86.

11. The method according to paragraph 10, wherein the thalidomide analog is compound 7, 9, 46, 59, 65, 74, or 86.

12. The method according to any one of paragraphs 9-11, wherein the non-teratogenic compound is administered orally, parenterally, rectally, nasally, buccally, vaginally, topically, optically, by inhalation spray, or via an implanted reservoir.

13. The method according to any one of paragraphs 9-12, further comprising administering to the subject a second therapeutic agent.

14. The method of paragraph 13, wherein the second therapeutic agent is an anti-inflammatory agent.

15. A method for treating an inflammatory disorder in a subject, comprising administering to the subject a therapeutically effective amount of a thalidomide analog according to paragraph 1, wherein the thalidomide analog is non-teratogenic and possesses anti-inflammatory properties.

16. The method according to paragraph 15, wherein the thalidomide analog is compound 7, 9, 46, 59, 64, 65, 72, 74, 77, or 86.

17. The method according to paragraph 16, wherein the thalidomide analog is compound 7, 9, 46, 59, 65, 74, or 86.

18. The method according to any one of paragraphs 15-17, wherein the inflammatory disorder is a neurodegenerative disorder.

19. The method according to paragraph 18, wherein the neurodegenerative disorder is Alzheimer's disease, Parkinson's disease, head trauma, stroke, amyotrophic lateral sclerosis, human immunodeficiency virus dementia, Huntington's disease, multiple sclerosis, cerebral amyloid angiopathy, a tauopathy, or macular degeneration.

20. The method according to any one of paragraphs 15-19, further comprising administering to the subject a second therapeutic agent.

21. The method according to paragraph 20, wherein the second therapeutic agent is an anti-inflammatory agent.

22. A method for inhibiting TNF-α activity in a subject, comprising administering to the subject a therapeutically effective amount of a thalidomide analog according to paragraph 1, wherein the thalidomide analog is non-teratogenic.

23. The method according to paragraph 22, wherein the thalidomide analog is compound 7, 9, 46, 59, 64, 65, 72, 74, 77, or 86.

24. The method according to paragraph 23, wherein the thalidomide analog is compound 7, 9, 46, 59, 65, 74, or 86.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for inhibiting TNF-α activity, TNF-α synthesis, angiogenesis, inflammation, or a combination thereof, comprising contacting a cell with an effective amount of a thalidomide analog or a pharmaceutically acceptable salt thereof, the thalidomide analog selected from compound 7, compound 9, compound 44, compound 69, compound 72, compound 76, compound 77, or any combination thereof:

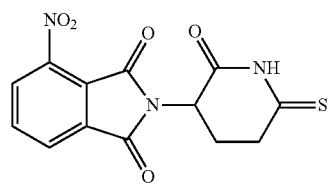

7

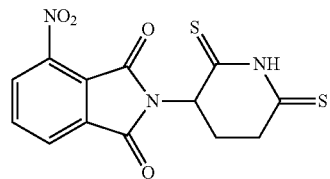

9

-continued

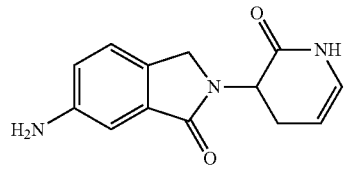

44

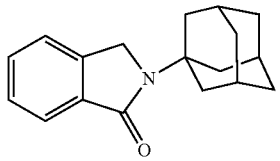

69

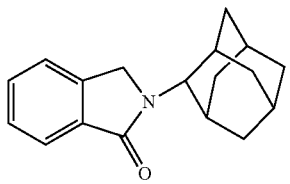

72

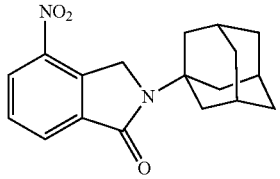

76

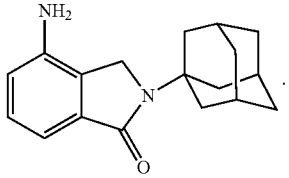

77

2. The method according to claim 1, wherein the thalidomide analog is non-teratogenic in a zebrafish embryo assay and/or a chicken embryo assay at a concentration within a range of 10-200 µg/mL.

3. The method according to claim 2, wherein the thalidomide analog is compound 7, compound 9, compound 72, compound 77, or a pharmaceutically acceptable salt thereof, or any combination thereof.

4. The method according to claim 1, wherein contacting the cell with an effective amount of the thalidomide analog comprises administering to a subject a therapeutically effective amount of the thalidomide analog or a pharmaceutically acceptable salt thereof or a therapeutically effective amount of a pharmaceutical composition comprising the thalidomide analog or a pharmaceutically acceptable salt thereof.

5. The method according to claim 4, wherein the thalidomide analog is non-teratogenic in a zebrafish embryo assay and/or a chicken embryo assay at a concentration within a range of 10-200 µg/mL.

6. The method according to claim 5, wherein the thalidomide analog is compound 7, compound 9, compound 72, compound 77, or a pharmaceutically acceptable salt thereof, or any combination thereof.

7. The method according to claim 4, wherein the subject has an inflammatory disorder or an autoimmune disorder.

8. The method according to claim 7, wherein the subject has sarcopenia, traumatic brain injury, spinal cord injury, Alzheimer's disease, Crohn's disease, rheumatoid arthritis, immune arthritis, degenerative arthritis, celiac disease, glomerulonephritis, lupus nephritis, prostatitis, inflammatory bowel disease, pelvic inflammatory disease, graft-versus-host disease, interstitial cystitis, autoimmune thyroiditis, Graves' disease; autoimmune pancreatitis, Sjogren's syndrome, myocarditis, autoimmune hepatitis, primary biliary cirrhosis, autoimmune angioedema, bullous pemphigoid, discoid lupus erythematosus, erythema nodosum leprosum, sarcoidosis, pemphigus vulgaris psoriasis, POEMS syndrome, polymyositis, human immune deficiency virus/acquired immune deficiency syndrome, vasculitis, stroke, Parkinson's disease, amyotrophic lateral sclerosis, human immunodeficiency virus dementia, Huntington's disease, multiple sclerosis, cerebral amyloid angiopathy, a tauopathy, peripheral neuropathy, macular degeneration, hearing loss, cochlear injury, epilepsy, a non-epileptic seizure disorder, or major depressive disorder.

9. The method according to claim 4, wherein the thalidomide analog possesses anti-inflammatory properties, and administering the therapeutically effective amount of the thalidomide analog or pharmaceutically acceptable salt thereof or the therapeutically effective amount of the pharmaceutical composition inhibits inflammation in the subject.

10. The method according to claim 9, wherein the thalidomide analog is compound 7, compound 9, compound 72, compound 76, compound 77, or a pharmaceutically acceptable salt thereof, or any combination thereof.

11. The method according to claim 9, wherein the subject has an inflammatory disorder, and administering the therapeutically effective amount of the thalidomide analog or pharmaceutically acceptable salt thereof or the therapeutically effective amount of the pharmaceutical composition to the subject treats the inflammatory disorder.

12. The method according to claim 11, wherein the inflammatory disorder is a neurodegenerative disorder or sarcopenia.

13. The method according to claim 12, wherein the neurodegenerative disorder is Alzheimer's disease, Parkinson's disease, neurodegeneration resulting from traumatic brain injury, neurodegeneration resulting from spinal cord injury, neurodegeneration resulting from stroke, amyotrophic lateral sclerosis, human immunodeficiency virus dementia, Huntington's disease, multiple sclerosis, cerebral amyloid angiopathy, a tauopathy, or macular degeneration.

14. The method according to claim 4, wherein the thalidomide analog possesses anti-angiogenic properties, and administering the therapeutically effective amount of the thalidomide analog or pharmaceutically acceptable salt thereof or the therapeutically effective amount of the pharmaceutical composition to the subject inhibits angiogenesis in the subject.

15. The method according to claim 14, wherein the thalidomide analog is compound 69.

16. The method according to claim 12, wherein inhibiting angiogenesis in the subject inhibits tumorigenesis, tumor metastasis, or angiogenesis-mediated retinopathy.

17. The method according to claim 16, wherein the tumor is a primary or metastatic solid tumor.

18. The method according to claim 4, wherein the thalidomide analog or pharmaceutically acceptable salt thereof or the pharmaceutical composition is administered orally, parenterally, rectally, nasally, buccally, vaginally, topically, optically, by inhalation spray, or via an implanted reservoir.

19. The method according to claim 4, further comprising administering to the subject a second therapeutic agent.

20. The method according to claim 19, wherein the second therapeutic agent is an anti-cancer agent, an anti-angiogenic agent, or an anti-inflammatory agent.

* * * * *